US009480735B2

(12) United States Patent
Mettens et al.

(10) Patent No.: US 9,480,735 B2
(45) Date of Patent: Nov. 1, 2016

(54) COMPOSITIONS AND METHODS

(71) Applicant: GlaxoSmithKline Biologicals S.A., Rixensart (BE)

(72) Inventors: Pascal Mettens, Rixensart (BE); James Brown, Collegeville, PA (US); Dennis Murphy, Collegeville, PA (US)

(73) Assignees: Glaxo Group Limited, Brentford, Middlesex (GB); GlaxoSmithKline Biologicals, SA, Rixensart (BE)

( * ) Notice: Subject to any disclaimer, the term of this patent is extended or adjusted under 35 U.S.C. 154(b) by 0 days.

(21) Appl. No.: 14/283,727

(22) Filed: May 21, 2014

(65) Prior Publication Data

US 2014/0314802 A1  Oct. 23, 2014

Related U.S. Application Data

(63) Continuation of application No. 13/929,232, filed on Jun. 27, 2013, now abandoned, which is a continuation of application No. 13/055,787, filed as application No. PCT/EP2009/059585 on Jul. 24, 2009, now abandoned.

(60) Provisional application No. 61/083,699, filed on Jul. 25, 2008.

(51) Int. Cl.
| | | |
|---|---|---|
| *A61K 39/00* | (2006.01) | |
| *A61K 39/02* | (2006.01) | |
| *A61K 39/04* | (2006.01) | |
| *C07K 14/35* | (2006.01) | |
| *C12N 9/88* | (2006.01) | |
| *C12N 9/90* | (2006.01) | |
| *A61K 38/00* | (2006.01) | |

(52) U.S. Cl.
CPC ............... *A61K 39/04* (2013.01); *C07K 14/35* (2013.01); *C12N 9/88* (2013.01); *C12N 9/90* (2013.01); *A61K 38/00* (2013.01); *A61K 2039/53* (2013.01); *A61K 2039/55555* (2013.01); *A61K 2039/55572* (2013.01); *A61K 2039/55577* (2013.01)

(58) Field of Classification Search
CPC ...... A61K 38/00; A61K 39/00; A61K 39/02; A61K 39/04; A61K 47/00; A61K 48/00; C07K 14/00; C07K 2/00; C07K 14/35; G01N 33/5695
USPC .................. 424/9.1, 9.2, 184.1, 185.1, 234.1, 424/248.1; 530/300, 350; 536/23.1, 23.7
See application file for complete search history.

(56) References Cited

U.S. PATENT DOCUMENTS

| | | |
|---|---|---|
| 5,750,110 A | 5/1998 | Prieels et al. |
| 2003/0236393 A1 | 12/2003 | Trucksis et al. |
| 2004/0086523 A1 | 5/2004 | Skeiky et al. |
| 2004/0197896 A1 | 10/2004 | Cole |

FOREIGN PATENT DOCUMENTS

| | | |
|---|---|---|
| EP | 0761231 A1 | 3/1997 |
| EP | 0671948 B1 | 8/1997 |
| WO | 94/00153 A1 | 1/1994 |
| WO | 98/53075 | 11/1998 |
| WO | 99/42076 A2 | 8/1999 |
| WO | 99/42118 A2 | 8/1999 |
| WO | 99/51748 A2 | 10/1999 |
| WO | 01/62893 | 8/2001 |
| WO | 03/070187 A2 | 8/2003 |
| WO | 2005/076010 | 8/2005 |
| WO | 2006/117240 A2 | 11/2006 |
| WO | 2008/007942 | 1/2008 |
| WO | 2008-107370 | 9/2008 |
| WO | 2010/010177 A1 | 1/2010 |
| WO | 2010/010178 A1 | 1/2010 |
| WO | 2010/010180 A1 | 1/2010 |
| WO | 2010/121618 A1 | 10/2010 |
| WO | 2010/132112 A2 | 11/2010 |
| WO | 2011/092253 A1 | 8/2011 |

OTHER PUBLICATIONS

Zwahlen, J. et al. Biochemistry, vol. 46, No. 4, pp. 954-964, Jan. 30, 2007.*
Orme, I.M., Vaccine, vol. 24, pp. 2-19, 2006.*
Girard, M.P., et al. Vaccine, vol. 23, pp. 572505731, 2005.*
Orme, I.M., et al., "Preclinical testing of new Vaccines for Tuberculosis: A comprehenive Review", Vaccine, Vo. 24, pp. 2-19, 2008.
Girard, M.P., et al., "A Review of Vaccine and Research and Development: Tuberculosis", Vaccing, vol. 23, pp. 5725-5731, 2005.
Al-Attiyah, et al., "In vitro Cellular Immune responses to complex and newly defined recombinant antigens of Mycobacterium Tuberculosis", Clinical and Experimental Immunology Blackwell Publishing Limited, vol. 138, No. 1, pp. 139-444, 2004.
Chaitra, et al., "Defining putative T cell epitopes from PE and PPE Families of Proteins of Mycobacterium Tuberculosis with Vaccine Potential", Vaccine, Elsevier, vol. 23., No. 10, pp. 1265-1272, 2005.
Chaitra, et al., "HLA-A 021 restricted cytoxic T-cell epitomes in three PE/PPE family proteins of Mycobacterium tuberculosis", Scandinavian Journal of Immunology, Wiley-Blackwell, vol. 67, No. 4, pp. 411-417, 2008.
Database uniProt [Online] Dec. 1, 2001"Subname: Full=PPE Rv 1753c; Flags: Fragment,:" XP002552251, retrieved from EBI accession No. UNIPROT: Q93M49, Database acession No. Q93M49 abstract.

(Continued)

*Primary Examiner* — Rodney P Swartz
(74) *Attorney, Agent, or Firm* — Eric J. Kron

(57) ABSTRACT

The present invention is directed to a polypeptide which comprises: (i) an Rv2386c protein sequence; (ii) a variant of an Rv2386c protein sequence; of (iii) an immunogenic fragment of an Rv2386c protein sequence. In other aspects the invention is directed to associated polynucleotides, fusion proteins and methods for the treatment or prevention of *tuberculosis*.

6 Claims, 9 Drawing Sheets

(56) References Cited

OTHER PUBLICATIONS

Database uniProt [Online] Jul. 10, 2007 "Full=PPE family protein," XP002552250 retrieved from EBI accession No. UNIPROT: A5U3B3, Database accession No. A5U3B3 abstract.

Database uniProt [Online] Mar. 20, 2008, "SubName: Full=PPE family protein," XP002552252, retrieved from EBI accession No. UNIPROT: A2VIN4, Database accession No. A2VIN4 abstract.

Database uniProt [Online] Feb. 6, 2007, "SubnName : Full=PPE family protein;" XP002552262, retrieved from EBI accession No. UNIPROT: A1KJH0, Database accession No. A1JKHO abstract.

Fortune, et al., "Mutually dependent secretion of proteins required for mycobaterial virulence", Proceedings of the National Academy of Sciences of the United States of Americal vol. 102, No. 30, pp. 10676-10681 an Database EMBL [Online] Jun. 28, 2005, "Integrating expression vector pALE2, complete sequence."XP002554336 retrieved from EBI accession No. EMBL:DQ08680.

Gey Van Pittius et al., "Evolution and Expansion of the Mycobacterium tuberculosis PE and PPE multigene families and their association with the duplication of the ESAT-6 (esx) gene cluster regions," BMC Evolutionaty Biology, Biomed Central Ltd., London, GB, vol. 6, No. 1, 95. (2006).

McLaughlin et al., "e105: A Mycobacterium ESX-1-Secreted Virulence Factor with Unique Requirements for Export", PLOS Pathogens, Public Library of Science, vol. 3, No. 8, pp. 1051-1061 (2007).

Mustafa et al., "Immunogencity of Mycobacterium Tuberculosis Antigens in Mycobacterium bovis BCG-vaccinated and M-bovis-infected cattle", Infection and Immunity, American Society for Microbiology, vol. 74, No. 8, pp. 4566-4572, (2006).

Raghavan, et al., "Secreted Transcription factor controls Mycobacterium Tuberculosis Virulence", Nature, Nature Publishing Group, vol. 454 No. 7205, p. 717 (2008).

Raviglione, et al., "Chapter 150: Tuberculosis + Titelseite + ISBN Seite" Harrison's Principles of International Medicine (16th edition), vol. 1, pp. 953-966, McGraw-Hill, Medical Publishing Division ISBN: 978-0-07-139140-5 (2005).

Reed, et al., "Tuberculosis Vaccine development; from mouse to man" Microbes and Infection, Elsevier, vol. 7, No. 5-6; pp. 922-931 (2005).

Romano, et al., "Immunogenicity and Protective Efficacy of Tuberculosis Subunit Vaccines Expressing PPE44 (Rv2770c)", Vaccine, Butterworth Scientific, Guildford, GB vol. 26, No. 48, pp. 6053-6063, Nov. 11, 2008.

Simeone, et al., "ESX/type VII secretion systems and their role in host-pathogen interaction", Current Opinion in Microiology, Current Biology Ltd., GB, Macmillian Publishers Limited, vol. 12, No. 1 pp. 4-10, 2009.

Skuce, et al., "Discrimination of Mycobacterium tuberculosis complex bacteria using novel VNTR-PCR targets", Microbiology, Springer Link, vol. 148, pt. 2, pp. 519-228, 2002.

Vipond, et al., "Selection of Novel TB vaccine candidates and their evaluation as DNA vaccines against aerosol callenge", Vaccine, Butterworth Scientific, Guildford, GB vol. 24, pp. 37-39, pp. 6340-6350; XP025151673. ISSN: 0264-410X [retrieved on Sep. 11, 2006] p. 6340-6350, Table 1: Vaccine candidate 9, 2006.

Database UniProt [Online] Jul. 5, 2004, "Isochorismate eynthase/ isochorismate-pyruvate lyase mbtl; EC No. 5.4.4.2" XP002553766 retrieved from EBI accession No. UNIPROT:Q7D785 Database accession No. Q7D785 abstract & Cole et al., "Deciphering the biology of Mycobacterium Tuberculosis from the complete genome sequence", Nature, Nature publishing Group, London, UK, vol. 393, pp. 537-544, 1998.

Kaufmann, et al., "Tuberculosis vaccine development: strenghth lies in tenacity", Cell Press, Trends in Immunology, Jul. 2012, vol. 33, No. 7, pp. 373-379.

McShane, et al., "A Review of Preclinical Animal models Utilised for TB Vaccine Evaluation in the context of Recent Human Efficacy Data", Tubeculosis, 2014, vol. 94, pp. 105-110.

Romano, et al., "DNA Vaccines Against Mycobacterial Diseases", Expert Rev. Vaccines, 2009, vol. 8, No. 9, pp. 1237-1250.

Young, et al, "Infectious Disease: Tuberculosis, Animal Models of Tuberculosis", Eur J. Immunolo, 2009, vol. 29, pp. 1991-2058.

Cole S et al, "Deciphering the biology of *Mycobacterium tuberculosis* from the complete genome sequence." Nature; 1998; pp. 537-544; vol. 393.

GenBank Accession No. BX842579.1, Oct. 23, 2008.

Harrison et al, "Crystallization and preliminary X-ray crystallographic analysis of Mbtl, a protein essential for siderophore biosynthesis in *Mycobacterium tuberculosis*." Acta Crystallographica Section F; 2005; pp. 121-124; vol. 61.

Harrison et al., "The Structure of mbtl from *Mycobacterium tuberculosis*, the First Enzyme in the Biosynthesis of the Siderophore Mycobactin, Reveals It To Be a Salicylate Synthase." J. Bacteriol.; 2006 pp. 6081-6091; vol. 188.

Gold et al., "The *Mycobacterium tuberculosis* IdeR is a dual functional regulator that controls transcription of genes involved in iron acquisition, iron storage and survival in macrophages." Molecular Microbiology; 2001; pp. 851-865; vol. 42.

Derrick S et al., "Vaccine-induced anti-tuberculosis protective immunity in mice correlates with the magnitude and duality of multifunctional CD4 T cells." Vaccine; 2011; pp. 2902-2909; vol. 29.

Reece S., "Skin Test Performed with Highly Purified Mycobacterium tuberculosis Recombinant Protein Triggers Tuberculin Shock in Infected Guinea Pigs." Infection and Immunity: 2005; 3301-3306; vol. 73(6).

Murphy et al., "Identification of gene targets against dormant phase *Mycobacterium tuberculosis* infections." BMC Infectious Diseases; 2007; pp. 1-16; vol. 7 (84).

Shi et al., "A review of murine models of latent tuberculosis infection." Scandinavian Journal of Infectious Diseases; 2011; pp. 848-856; vol. 43.

Taylor, "Pulmonary Necrosis Resulting from DNA Vaccination against tuberculosis." Infection and Immunity; 2003; pp. 2192-2198; vol. 71(4).

Turner J et al., "Effective Preexposure Tuberculosis Vaccines Fail to Protect When They Are Given in an Immunotherapeutic Mode." Infection and Immunity; 2000; pp. 1706-1709; vol. 68(3).

Martin, "Tuberculosis vaccines: past, present and future." Current Opinion in Pulmonary medicine; 2006 pp. 186-191; vol. 12(3).

* cited by examiner

COMPOSITIONS AND METHODS

CROSS REFERENCE TO RELATED APPLICATIONS

This application is a continuation of U.S. Ser. No. 13/929,232, now abandoned, which is a continuation of U.S. Ser. No. 13/055,787, now abandoned, which is the US National Stage of International Application No. PCT/EP2009/059585, filed 24 Jul. 2009, which claims benefit of the filing date of U.S. Provisional Application No. 61/083,699, filed 25 Jul. 2008, which is incorporated herein by reference in its entirety.

FIELD OF THE INVENTION

The present invention relates to polypeptides and polynucleotides for use in the treatment or prevention of *tuberculosis*, in particular for use in the treatment or prevention of latent *tuberculosis* and in the prevention or delay of reactivation of *tuberculosis* (and also to related methods). The present invention further relates to pharmaceutical and immunogenic compositions comprising said polypeptides and polynucleotides, and to methods for the diagnosis of *tuberculosis* (in particular latent *tuberculosis*).

BACKGROUND OF THE INVENTION

*Tuberculosis* (TB) is a chronic infectious disease caused by infection with *Mycobacterium tuberculosis* and other *Mycobacterium* species. It is a major disease in developing countries, as well as an increasing problem in developed areas of the world. More than 2 billion people are believed to be infected with TB bacilli, with about 9.2 million new cases of TB and 1.7 million deaths each year. 10% of those infected with TB bacilli will develop active TB, each person with active TB infecting an average of 10 to 15 others per year. While annual incidence rates have peaked globally, the number of deaths and cases is still rising due to population growth (World Health Organisation *Tuberculosis Facts* 2008).

*Mycobacterium tuberculosis* infects individuals through the respiratory route. Alveolar macrophages engulf the bacterium, but it is able to survive and proliferate by inhibiting phagosome fusion with acidic lysosomes. A complex immune response involving CD4+ and CD8+ T cells ensues, ultimately resulting in the formation of a granuloma. Central to the success of *Mycobacterium tuberculosis* as a pathogen is the fact that the isolated, but not eradicated, bacterium may persist for long periods, leaving an individual vulnerable to the later development of active TB.

Fewer than 5% of infected individuals develop active TB in the first years after infection. The granuloma can persist for decades and is believed to contain live *Mycobacterium tuberculosis* in a state of dormancy, deprived of oxygen and nutrients. However, recently it has been suggested that the majority of the bacteria in the dormancy state are located in non-macrophage cell types spread throughout the body (Locht et al, *Expert Opin. Biol. Ther.* 2007 7(11):1665-1677). The development of active TB occurs when the balance between the host's natural immunity and the pathogen changes, for example as a result of an immunosuppressive event (Anderson P *Trends in Microbiology* 2007 15(1):7-13; Ehlers S *Infection* 2009 37(2):87-95).

A dynamic hypothesis describing the balance between latent TB and active TB has also been proposed (Cardana P-J *Inflammation & Allergy—Drug Targets* 2006 6:27-39; Cardana P-J *Infection* 2009 37(2):80-86).

Although an infection may be asymptomatic for a considerable period of time, the active disease is most commonly manifested as an acute inflammation of the lungs, resulting in tiredness, weight loss, fever and a persistent cough. If untreated, serious complications and death typically result.

*Tuberculosis* can generally be controlled using extended antibiotic therapy, although such treatment is not sufficient to prevent the spread of the disease. Infected individuals may be asymptomatic, but contagious, for some time. In addition, although compliance with the treatment regimen is critical, patient behaviour is difficult to monitor. Some patients do not complete the course of treatment, which can lead to ineffective treatment and the development of drug resistance.

Multidrug-resistant TB (MDR-TB) is a form which fails to respond to first line medications. 5% of all TB cases are MDR-TB, with an estimated 490,000 new MDR-TB cases occurring each year. Extensively drug-resistant TB (XDR-TB) occurs when resistance to second line medications develops on top of MDR-TB. It is estimated that 40,000 new cases of the virtually untreatable XDR-TB arise annually (World Health Organisation *Tuberculosis Facts* 2008).

Even if a full course of antibiotic treatment is completed, infection with *M. tuberculosis* may not be eradicated from the infected individual and may remain as a latent infection that can be reactivated.

In order to control the spread of *tuberculosis*, effective vaccination and accurate early diagnosis of the disease are of utmost importance.

Diagnosis of latent TB infection is commonly achieved using the tuberculin skin test, which involves intradermal exposure to tuberculin protein-purified derivative (PPD). Antigen-specific T cell responses result in measurable induration at the injection site by 48-72 hours after injection, which indicates exposure to mycobacterial antigens. Sensitivity and specificity have, however, been a problem with this test, and individuals vaccinated with BCG cannot always be easily distinguished from infected individuals (this is particularly important in light of the fact that BCG does not protect against latent infection). In general, individuals who have received BCG but are not infected by *M. tuberculosis* show a PPD reaction below 10 mm in diameter whereas people who have a PPD reaction above 10 mm in diameter are considered to have been infected by *M. tuberculosis*. However, this rule is not applicable to individuals with immunosuppression due to HIV infection, which may result in a PPD reaction below 10 mm in diameter); or in endemic countries, where people infected by non-*tuberculosis* mycobacteria can show a PPD reaction above 10 mm in diameter.

Progress over recent years has seen the development of in vitro T cell based assays, based on interferon-gamma release and using antigens which are more specific to *M. tuberculosis* than PPD, namely ESAT-6 and CFP-10. These high specificity tests appear to be at least as sensitive as the tuberculin skin test and also demonstrate less cross-reactivity due to BCG vaccination. See Pai M et al *Expert Rev. Mol. Diagn.* 2006 6(3):413-422 for a recent review of latent TB diagnosis. However, since ESAT-6/CFP-10 are early stage antigens, assays based on ESAT-6/CFP-10 may only perform optimally in recently infected people. Consequently, the identification of new antigens specifically associated with latent *tuberculosis* may aid the development of more sensitive assays that could detect longer-term latent infections.

There remains a need for effective strategies for the treatment and prevention of *tuberculosis*, in particular the treatment and prevention of latent TB and the prevention of reactivation of TB.

BRIEF SUMMARY OF THE INVENTION

The present invention relates generally to the identification of Rv2386c as a TB antigen (in particular an antigen associated with latent TB) and to related methods and uses in the prevention and treatment of TB, especially the prevention and treatment of latent TB and the prevention or delay of TB reactivation.

The present invention provides an isolated polypeptide which comprises:
(i) an Rv2386c protein sequence;
(ii) a variant of an Rv2386c protein sequence; or
(iii) an immunogenic fragment of an Rv2386c protein sequence.

The present invention also provides a polypeptide which comprises:
(i) an Rv2386c protein sequence;
(ii) a variant of an Rv2386c protein sequence; or
(iii) an immunogenic fragment of an Rv2386c protein sequence;
for use as a medicament.

A further aspect of the invention relates to a method for the treatment or prevention of TB comprising the administration of a safe and effective amount of a polypeptide comprising:
(i) an Rv2386c protein sequence;
(ii) a variant of an Rv2386c protein sequence; or
(iii) an immunogenic fragment of an Rv2386c protein sequence;
to a subject in need thereof, wherein said polypeptide induces an immune response, in particular an immune response against *Mycobacterium tuberculosis*.

The use of a polypeptide comprising:
(i) an Rv2386c protein sequence;
(ii) a variant of an Rv2386c protein sequence; or
(iii) an immunogenic fragment of an Rv2386c protein sequence;
in the manufacture of a medicament for the treatment or prevention of TB, represents another aspect of the invention.

The present invention provides an isolated polynucleotide comprising a nucleic acid sequence encoding a polypeptide which comprises:
(i) an Rv2386c protein sequence;
(ii) a variant of an Rv2386c protein sequence; or
(iii) an immunogenic fragment of an Rv2386c protein sequence.

Also provided is a polynucleotide comprising a nucleic acid sequence encoding a polypeptide which comprises:
(i) an Rv2386c protein sequence;
(ii) a variant of an Rv2386c protein sequence; or
(iii) an immunogenic fragment of an Rv2386c protein sequence;
for use as a medicament.

A further aspect of the invention relates to a method for the treatment or prevention of TB comprising the administration of a safe and effective amount of a polynucleotide comprising a nucleic acid sequence encoding a polypeptide comprising:
(i) an Rv2386c protein sequence;
(ii) a variant of an Rv2386c protein sequence; or
(iii) an immunogenic fragment of an Rv2386c protein sequence;
to a subject in need thereof, wherein said polynucleotide induces an immune response, in particular an immune response against *Mycobacterium tuberculosis*.

Use of a polynucleotide comprising a nucleic acid sequence encoding a polypeptide comprising:
(i) an Rv2386c protein sequence;
(ii) a variant of an Rv2386c protein sequence; or
(iii) an immunogenic fragment of an Rv2386c protein sequence;
in the manufacture of a medicament for the treatment or prevention of TB, represents another aspect of the invention.

Additionally, there is provided a pharmaceutical composition comprising:
(a) a polypeptide which comprises:
(i) an Rv2386c protein sequence;
(ii) a variant of an Rv2386c protein sequence; or
(iii) an immunogenic fragment of an Rv2386c protein sequence; or
(b) a polynucleotide comprising a nucleic acid sequence encoding the polypeptide of (a);
and
(c) a pharmaceutically acceptable carrier or excipient.

Further, there is provided an immunogenic composition comprising:
(a) a polypeptide which comprises:
(i) an Rv2386c protein sequence;
(ii) a variant of an Rv2386c protein sequence; or
(iii) an immunogenic fragment of an Rv2386c protein sequence; or
(b) a polynucleotide comprising a nucleic acid sequence encoding the polypeptide of (a);
and
(c) a non-specific immune response enhancer.

Suitably the pharmaceutical and immunogenic composition comprise a combination of an Rv2386c and a second heterologous *tuberculosis* antigen component.

Also provided is an expression vector comprising a nucleic acid sequence encoding a polypeptide which comprises:
(i) an Rv2386c protein sequence;
(ii) a variant of an Rv2386c protein sequence; or
(iii) an immunogenic fragment of an Rv2386c protein sequence.

Host cells, transformed with said expression vector, form a further aspect of the invention. Additionally provided is a host cell which recombinantly expresses a polypeptide which comprises:
(i) an Rv2386c protein sequence;
(ii) a variant of an Rv2386c protein sequence; or
(iii) an immunogenic fragment of an Rv2386c protein sequence.

Further, there is provided a method for the production of a polypeptide comprising:
(i) an Rv2386c protein sequence;
(ii) a variant of an Rv2386c protein sequence; or
(iii) an immunogenic fragment of an Rv2386c protein sequence;
said method comprising the step of recombinantly expressing said polypeptide within a host cell.

Additionally provided is an antibody or fragment thereof which specifically binds to a polypeptide comprising:
(i) an Rv2386c protein sequence;
(ii) a variant of an Rv2386c protein sequence; or (iii) an immunogenic fragment of an Rv2386c protein sequence.

The use of said antibodies in diagnosis is also provided (such as methods for the diagnosis of *tuberculosis* comprising determining the presence of an antibody or fragment thereof which specifically binds to the polypeptides of the invention in a biological sample from a test subject).

Also provided are diagnostic kits comprising:
(a) a polypeptide of the present invention;
(b) apparatus sufficient to contact said polypeptide with a sample (e.g. whole blood or more suitably PBMC) from an individual; and
(c) means to quantify the T cell response of the sample.

Another aspect of the invention relates to a diagnostic kit comprising:
(a) a polypeptide of the present invention; and
(b) apparatus sufficient to contact said polypeptide with the dermal cells of a patient.

In one embodiment the subject receiving a polypeptide, polynucleotide or composition of the invention may have active *tuberculosis* (e.g. active infection by *M. tuberculosis*). In a second embodiment the subject may have latent *tuberculosis* (e.g. dormant infection by *M. tuberculosis*). In a third embodiment the subject may be free from *tuberculosis* (e.g. free from infection by *M. tuberculosis*).

A subject receiving a polypeptide, polynucleotide or composition of the invention may have previously been vaccinated for *tuberculosis* (e.g. vaccinated against infection by *M. tuberculosis*), such as having been vaccinated with *Bacillus* Calmette-Guerin (BCG). Alternatively, a subject receiving a polypeptide, polynucleotide or composition of the invention may not have previously been vaccinated for *tuberculosis* (e.g. not vaccinated against infection by *M. tuberculosis*), such as not having been vaccinated with *Bacillus* Calmette-Guerin (BCG).

DESCRIPTION OF THE LISTED SEQUENCES

Figure 1:
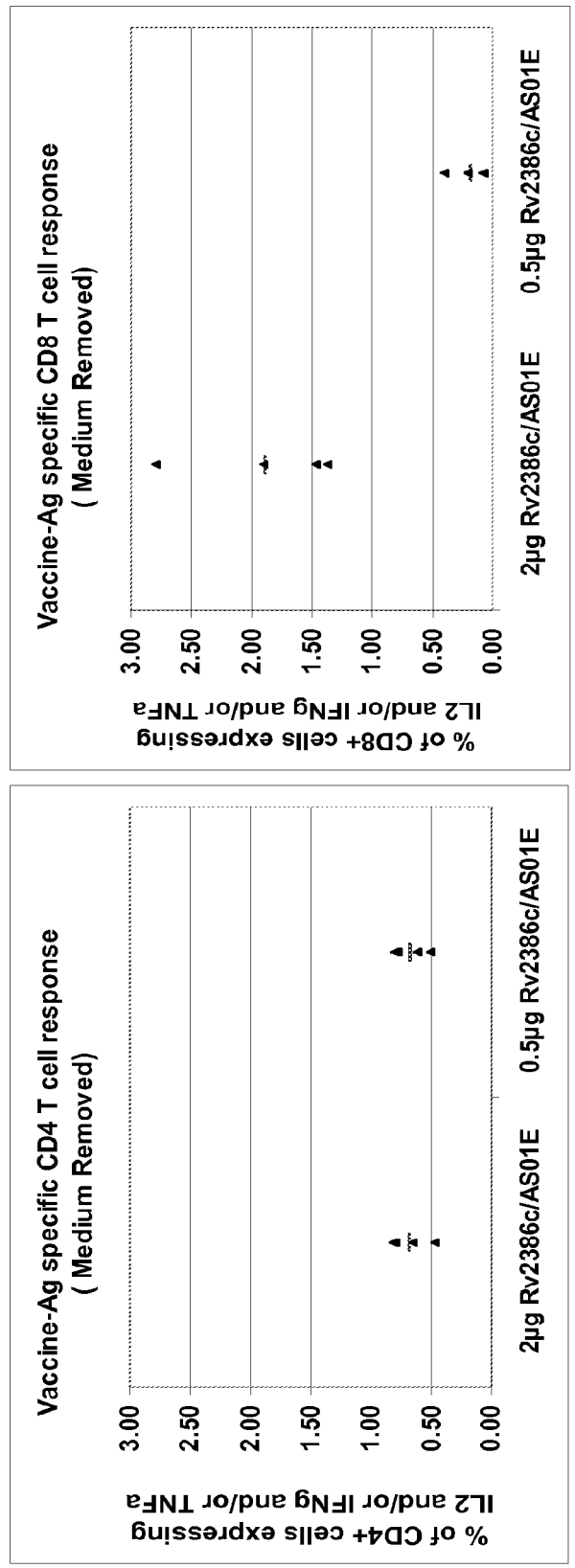
FIG. 1: Percentage of CD4 and CD8 cells from immunised CB6F1 mice expressing IFN-gamma and/or IL-2 and/or TNF-alpha cytokines at day 21 (i.e. 7 days post second immunisation).

SEQ ID No: 1: polypeptide sequence of Rv2386c from *M. tuberculosis* H37Rv strain.
SEQ ID No: 2: polynucleotide sequence of Rv2386c from *M. tuberculosis* H37Rv strain.
SEQ ID No: 3: polypeptide sequence of Rv2386c from *M. tuberculosis* CDC1551 strain.
SEQ ID No: 4: polypeptide sequence of Rv2386c from *M. tuberculosis* F11 strain.
SEQ ID No: 5: polypeptide sequence of Rv2386c from *M. tuberculosis* Haarlem A strain.
SEQ ID No: 6: polypeptide sequence of Rv2386c from *M. tuberculosis* C strain.
SEQ ID No: 7: polypeptide sequence of Rv2386c from BCG.
SEQ ID No: 8: polypeptide sequence of Mtb8.4.
SEQ ID No: 9: polypeptide sequence of Mtb9.8.
SEQ ID No: 10: polypeptide sequence of Mtb9.9.
SEQ ID No: 11: polypeptide sequence of Ra12.
SEQ ID No: 12: polypeptide sequence of Ra35.
SEQ ID No: 13: polypeptide sequence of TbH9.
SEQ ID No: 14: polypeptide sequence of Mtb40.
SEQ ID No: 15: polypeptide sequence of Mtb41.
SEQ ID No: 16: polypeptide sequence of ESAT-6.
SEQ ID No: 17: polypeptide sequence of Ag85A.
SEQ ID No: 18: polypeptide sequence of Ag85B.
SEQ ID No: 19: polypeptide sequence of alpha-crystallin.
SEQ ID No: 20: polypeptide sequence of MPT64.
SEQ ID No: 21: polypeptide sequence of Mtb32A.
SEQ ID No: 22: polypeptide sequence of Ser/Ala mutated mature Mtb32A.
SEQ ID No: 23: polypeptide sequence of TB10.4.
SEQ ID No: 24: polypeptide sequence of Mtb72f.
SEQ ID No: 25: polypeptide sequence of M72.
SEQ ID No: 26: polypeptide sequence of Mtb71f.
SEQ ID No: 27: polypeptide sequence of M92 fusion.
SEQ ID No: 28: polypeptide sequence of M103 fusion.
SEQ ID No: 29: polypeptide sequence of M114 fusion.
SEQ ID No: 30: putative human CD4 cell epitope 1.
SEQ ID No: 31: putative human CD4 cell epitope 2.
SEQ ID No: 32: putative human CD4 cell epitope 3.
SEQ ID No: 33: putative human CD4 cell epitope 4.
SEQ ID No: 34: putative human CD4 cell epitope 5.
SEQ ID No: 35: putative human CD4 cell epitope 6.
SEQ ID No: 36: putative human CD4 cell epitope 7.
SEQ ID No: 37: putative human CD4 cell epitope 8.
SEQ ID No: 38: putative human CD4 cell epitope 9.
SEQ ID No: 39: putative human CD4 cell epitope 10.
SEQ ID No: 40: putative human CD4 cell epitope 11.
SEQ ID No: 41: putative human CD4 cell epitope 12.
SEQ ID No: 42: putative human CD4 cell epitope 13.
SEQ ID No: 43: putative human CD4 cell epitope 14.
SEQ ID No: 44: putative human CD4 cell epitope 15.
SEQ ID No: 45: putative human CD4 cell epitope 16.
SEQ ID No: 46: putative human CD4 cell epitope 17.
SEQ ID No: 47: putative human CD4 cell epitope 18.
SEQ ID No: 48: putative human CD4 cell epitope 19.
SEQ ID No: 49: putative human CD4 cell epitope 20.
SEQ ID No: 50: putative human CD4 cell epitope 21.
SEQ ID No: 51: putative human CD4 cell epitope 22.
SEQ ID No: 52: putative human CD4 cell epitope 23.
SEQ ID No: 53: putative human CD8 cell epitope 1.

SEQ ID No: 54: putative human CD8 cell epitope 2.
SEQ ID No: 55: putative human CD8 cell epitope 3.
SEQ ID No: 56: putative human CD8 cell epitope 4.
SEQ ID No: 57: putative human CD8 cell epitope 5.
SEQ ID No: 58: putative human CD8 cell epitope 6.
SEQ ID No: 59: putative human CD8 cell epitope 7.
SEQ ID No: 60: putative human CD8 cell epitope 8.
SEQ ID No: 61: putative human CD8 cell epitope 9.
SEQ ID No: 62: putative human CD8 cell epitope 10.
SEQ ID No: 63: putative human CD8 cell epitope 11.
SEQ ID No: 64: putative human CD8 cell epitope 12.
SEQ ID No: 65: putative human CD8 cell epitope 13.
SEQ ID No: 66: putative human CD8 cell epitope 14.
SEQ ID No: 67: putative human CD8 cell epitope 15.
SEQ ID No: 68: putative human CD8 cell epitope 16.
SEQ ID No: 69: putative human CD8 cell epitope 17.
SEQ ID No: 70: putative human CD8 cell epitope 18.
SEQ ID No: 71: putative human CD8 cell epitope 19.
SEQ ID No: 72: putative human CD8 cell epitope 20.
SEQ ID No: 73: putative human CD8 cell epitope 21.
SEQ ID No: 74: putative human CD8 cell epitope 22.
SEQ ID No: 75: putative human CD8 cell epitope 23.
SEQ ID No: 76: putative human CD8 cell epitope 24.
SEQ ID No: 77: putative human CD8 cell epitope 25.
SEQ ID No: 78: putative human CD8 cell epitope 26.
SEQ ID No: 79: putative human CD8 cell epitope 27
SEQ ID No: 80: putative human CD8 cell epitope 28.
SEQ ID No: 81: putative human CD8 cell epitope 29.
SEQ ID No: 82: putative human CD8 cell epitope 30.
SEQ ID No: 83: putative human CD8 cell epitope 31.
SEQ ID No: 84: putative human CD8 cell epitope 32.
SEQ ID No: 85: putative human CD8 cell epitope 33.
SEQ ID No: 86: putative human CD8 cell epitope 34.
SEQ ID No: 87: putative human CD8 cell epitope 35.
SEQ ID No: 88: putative human CD8 cell epitope 36.
SEQ ID No: 89: putative human CD8 cell epitope 37.
SEQ ID No: 90: putative human CD8 cell epitope 38.
SEQ ID No: 91: putative human CD8 cell epitope 39.
SEQ ID No: 92: putative human CD8 cell epitope 40.
SEQ ID No: 93: putative human CD8 cell epitope 41.
SEQ ID No: 94: putative human CD8 cell epitope 42.
SEQ ID No: 95: putative human CD8 cell epitope 43.
SEQ ID No: 96: putative human CD8 cell epitope 44.
SEQ ID No: 97: putative human CD8 cell epitope 45.
SEQ ID No: 98: putative human CD8 cell epitope 46.
SEQ ID No: 99: putative human CD8 cell epitope 47.
SEQ ID No: 100: putative human CD8 cell epitope 48.
SEQ ID No: 101: putative human CD8 cell epitope 49.
SEQ ID No: 102: putative human CD8 cell epitope 50.
SEQ ID No: 103: putative human CD8 cell epitope 51.
SEQ ID No: 104: putative human CD8 cell epitope 52.
SEQ ID No: 105: putative human CD8 cell epitope 53.
SEQ ID No: 106: putative human CD8 cell epitope 54.
SEQ ID No: 107: putative human CD8 cell epitope 55.
SEQ ID No: 108: putative human CD8 cell epitope 56.
SEQ ID No: 109: putative human CD8 cell epitope 57.
SEQ ID No: 110: putative human CD8 cell epitope 58.
SEQ ID No: 111: putative human CD8 cell epitope 59.
SEQ ID No: 112: putative human CD8 cell epitope 60.
SEQ ID No: 113: putative human CD8 cell epitope 61.
SEQ ID No: 114: putative human CD8 cell epitope 62.
SEQ ID No: 115: putative human CD8 cell epitope 63.
SEQ ID No: 116: putative human CD8 cell epitope 64.
SEQ ID No: 117: putative human CD8 cell epitope 65.
SEQ ID No: 118: putative human CD8 cell epitope 66.
SEQ ID No: 119: putative human CD8 cell epitope 67.
SEQ ID No: 120: putative human CD8 cell epitope 68.
SEQ ID No: 121: putative human CD8 cell epitope 69.
SEQ ID No: 122: putative human CD8 cell epitope 70.
SEQ ID No: 123: putative human CD8 cell epitope 71.
SEQ ID No: 124: putative human CD8 cell epitope 72.
SEQ ID No: 125: putative human CD8 cell epitope 73.
SEQ ID No: 126: putative human CD8 cell epitope 74.
SEQ ID No: 127: putative human CD8 cell epitope 75.
SEQ ID No: 128: putative human CD8 cell epitope 76.
SEQ ID No: 129: putative human CD8 cell epitope 77.
SEQ ID No: 130: putative human CD8 cell epitope 78.
SEQ ID No: 131: putative human CD8 cell epitope 79.
SEQ ID No: 132: putative human CD8 cell epitope 80.
SEQ ID No: 133: putative human CD8 cell epitope 81.
SEQ ID No: 134: putative human CD8 cell epitope 82.
SEQ ID No: 135: putative human CD8 cell epitope 83.
SEQ ID No: 136: putative human CD8 cell epitope 84.
SEQ ID No: 137: putative human CD8 cell epitope 85.
SEQ ID No: 138: putative human CD8 cell epitope 86.
SEQ ID No: 139: putative human CD8 cell epitope 87.
SEQ ID No: 140: putative human CD8 cell epitope 88.
SEQ ID No: 141: putative human CD8 cell epitope 89.
SEQ ID No: 142: putative human CD8 cell epitope 90.
SEQ ID No: 143: putative human CD8 cell epitope 91.
SEQ ID No: 144: putative human CD8 cell epitope 92.
SEQ ID No: 145: putative human CD8 cell epitope 93.
SEQ ID No: 146: putative human CD8 cell epitope 94.
SEQ ID No: 147: putative human CD8 cell epitope 95.
SEQ ID No: 148: putative human CD8 cell epitope 96.
SEQ ID No: 149: putative human CD8 cell epitope 97.
SEQ ID No: 150: putative human CD8 cell epitope 98.
SEQ ID No: 151: putative human CD8 cell epitope 99.
SEQ ID No: 152: putative human CD8 cell epitope 100.
SEQ ID No: 153: putative human CD8 cell epitope 101.
SEQ ID No: 154: putative human CD8 cell epitope 102.
SEQ ID No: 155: polypeptide sequence of Rv1753c from *M. tuberculosis* H37Rv strain.
SEQ ID No: 156: polypeptide sequence of Rv2707c from *M. tuberculosis* H37Rv strain.

DETAILED DESCRIPTION

Currently, vaccination with live bacteria is the most efficient method for inducing protective immunity. The most common *Mycobacterium* employed for this purpose is *Bacillus* Calmette-Guerin (BCG), an avirulent strain of *M. bovis* which was developed over 60 years ago. However, the safety and efficacy of BCG is a source of controversy—while protecting against severe disease manifestation in children, BCG does not prevent the establishment of latent TB or reactivation of pulmonary disease in adult life. Additionally, some countries, such as the United States, do not vaccinate the general public with this agent.

Almost all new generation TB vaccines which are currently in clinical development have been designed as pre-exposure vaccines. These include subunit vaccines, which have been particularly effective in boosting immunity induced by prior BCG vaccination, and advanced live mycobacterial vaccines which aim to replace BCG with more efficient and/or safer strains. Although these vaccines aim to improve resistance to infection, they are likely to be less effective as post-exposure or therapeutic vaccines in latent TB cases (Lin M Y et al Endocrine, Metabolic & Immune Disorders—Drug Targets 2008 8:15-29).

Several of the proteins which are strongly expressed during the early stages of *Mycobacterium* infection have been shown to provide strong protective efficacy in animal vaccination models. However, vaccination with antigens which are highly expressed during the early stages of infection may not provide an optimal immune response for dealing with later stages of infection. Adequate control during the later stages of infection may require T cells which are specific for the particular antigens which are expressed at that time.

Post-exposure vaccines which directly target the dormant persistent bacteria may aid in protecting against TB reactivation, thereby enhancing TB control, or even enabling clearance of the infection. A vaccine targeting latent TB could therefore significantly and economically reduce global TB infection rates.

Subunit vaccines based on late stage antigens could also be utilised in combination with early stage antigens to provide a multiphase vaccine. Alternatively, late stage antigens could be used to complement and improve BCG vaccination (either by boosting the BCG response or through the development of advanced recombinant BCG strains).

Rv2386c, also known as Mbtl, catalyses the initial transformation in mycobactin biosynthesis by converting chorismate to salicylate (Zwahlen et al. *Biochemistry* 2007 46:954-964). Rv2386 has previously been identified as being associated with expression under stress conditions although did not result in protection when administered as a DNA vaccine in a guinea pig model (Vipond et al. *Vaccine* 2006 24:6340-6350).

Recently, a range of *M. tuberculosis* vaccine candidates have been proposed based on a bioinformatics analysis of the whole genome *M. tuberculosis* genome (Zvi et al. *BMC Medical Genetics* 2008 1:18) and on the testing of differentially expressed proteins in actively and latently infected individuals (Schuck S D et al. *PLoS ONE* 2009 4(5):e5590).

While macrophages have been shown to act as the principal effectors of *Mycobacterium* immunity, T cells are the predominant inducers of such immunity. The essential role of T cells in protection against *tuberculosis* is illustrated by the increased rates of TB reactivation in human immunodeficiency virus infected individuals, due to the associated depletion of CD4+ T cells. Furthermore, adoptive transfer of CD4+ T cells taken at the height of the primary immune response to *M. tuberculosis* has been shown to confer protection against *M. tuberculosis* in T cell deficient mice (Orme et al *J. Exp. Med.* 1983 158:74-83).

*Mycobacterium*-reactive CD4+ T cells have been shown to be potent producers of γ-interferon (IFN-γ), which, in turn, has been shown to trigger the anti-mycobacterial effects of macrophages in mice (Flynn et al. *J. Exp. Med.* 1993 178:2249-2254). While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan & Kaufmann, *Tuberculosis: Pathogenesis, Protection and Control* (Bloom ed., 1994), *Tuberculosis* (2nd ed., Rom and Garay, eds., 2003), and *Harrison's Principles of Internal Medicine*, Chapter 150, pp. 953-966 (16th ed., Braunwald, et al., eds., 2005).

The present invention relates generally to the identification of Rv2386c as a TB antigen (in particular an antigen associated with latent TB) and to related methods and uses in the prevention and treatment of TB, especially the prevention and treatment of latent TB and the prevention or delay of TB reactivation.

The invention therefore provides an Rv2386c protein, variant thereof or immunogenic fragment thereof, or a polynucleotide encoding said protein, variant or fragment, for use in the treatment or prevention of TB. Suitably, the use may be specifically in the prevention and treatment of latent TB (especially the treatment of latent TB). Alternatively, the use may be in the prevention or delay of TB reactivation (especially the delay of TB reactivation, for example by a period of months, years or even indefinitely).

The term "*Mycobacterium* species of the *tuberculosis* complex" includes those species traditionally considered as causing the disease *tuberculosis*, as well as *Mycobacterium* environmental and opportunistic species that cause *tuberculosis* and lung disease in immune compromised patients, such as patients with AIDS, e.g., *M. tuberculosis, M. bovis*, or *M. africanum*, BCG, *M. avium, M. intracellulare, M. celatum, M. genavense, M. haemophilum, M. kansasii, M. simiae, M. vaccae, M. fortuitum*, and *M. scrofulaceum* (see, e.g., *Harrison's Principles of Internal Medicine*, Chapter 150, pp. 953-966 (16th ed., Braunwald, et al., eds., 2005). The present invention is particularly directed to infection with *M. tuberculosis.*

The term "active infection" refers to an infection (e.g. infection by *M. tuberculosis*) with manifested disease symptoms and/or lesions (suitably with manifested disease symptoms).

The terms "inactive infection", "dormant infection" or "latent infection" refer to an infection (e.g. infection by *M. tuberculosis*) without manifested disease symptoms and/or lesions (suitably without manifested disease symptoms).

The term "primary *tuberculosis*" refers to clinical illness (manifestation of disease symptoms) directly following infection (e.g. infection by *M. tuberculosis*). See, *Harrison's Principles of Internal Medicine*, Chapter 150, pp. 953-966 (16th ed., Braunwald, et al., eds., 2005).

The terms "secondary *tuberculosis*" or "postprimary *tuberculosis*" refer to the reactivation of a dormant, inactive or latent infection (e.g. infection by *M. tuberculosis*). See, *Harrison's Principles of Internal Medicine*, Chapter 150, pp. 953-966 (16th ed., Braunwald, et al., eds., 2005).

The term "*tuberculosis* reactivation" refers to the later manifestation of disease symptoms in an individual that tests positive for infection (e.g. in a tuberculin skin test, suitably in an in vitro T cell based assay) test but does not have apparent disease symptoms. The positive diagnostic test indicates that the individual is infected, however, the individual may or may not have previously manifested active disease symptoms that had been treated sufficiently to bring the *tuberculosis* into an inactive or latent state. It will be recognised that methods for the prevention, delay or treatment of *tuberculosis* reactivation can be initiated in an individual manifesting active symptoms of disease.

The term "drug resistant" *tuberculosis* refers to an infection (e.g. infection by *M. tuberculosis*) wherein the infecting strain is not held static or killed (i.e. is resistant to) one or more of so-called "front-line" chemotherapeutic agents effective in treating *tuberculosis* (e.g., isoniazid, rifampin, ethambutol, streptomycin and pyrazinamide).

The term "multi-drug resistant" *tuberculosis* refers to an infection (e.g. infection by *M. tuberculosis*) wherein the infecting strain is resistant to two or more of "front-line" chemotherapeutic agents effective in treating *tuberculosis.*

A "chemotherapeutic agent" refers to a pharmacological agent known and used in the art to treat *tuberculosis* (e.g. infection by *M. tuberculosis*). Exemplified pharmacological agents used to treat *tuberculosis* include, but are not limited to amikacin, aminosalicylic acid, capreomycin, cycloserine, ethambutol, ethionamide, isoniazid, kanamycin, pyrazinamide, rifamycins (i.e., rifampin, rifapentine and rifabutin), streptomycin, ofloxacin, ciprofloxacin, clarithromycin, azithromycin and fluoroquinolones. "First-line" or "Frontline" chemotherapeutic agents used to treat *tuberculosis* that is not drug resistant include isoniazid, rifampin, ethambutol, streptomycin and pyrazinamide. "Second-line" chemotherapeutic agents used to treat *tuberculosis* that has demonstrated drug resistance to one or more "first-line" drugs include ofloxacin, ciprofloxacin, ethionamide, aminosalicylic acid, cycloserine, amikacin, kanamycin and capreomycin. Such pharmacological agents are reviewed in Chapter 48 of *Goodman and Gilman's The Pharmacological Basis of Therapeutics*, Hardman and Limbird eds., 2001.

The terms "polypeptide", "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer. Suitably a polypeptide according to the present invention will consist only of naturally occurring amino acid residues, especially those amino acids encoded by the genetic code.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogues refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Suitably an amino acid is a naturally occurring amino acid or an amino acid analogue, especially a naturally occurring amino acid and in particular those amino acids encoded by the genetic code.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Suitably the term "nucleic acid" refers to naturally occurring deoxyribonucleotides or ribonucleotides and polymers thereof.

Unless otherwise indicated, a particular nucleic acid sequence also implicitly encompasses conservatively modified variants thereof (e.g., degenerate codon substitutions) and complementary sequences, as well as the sequence explicitly indicated (suitably it refers to the sequence explicitly indicated). Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

By the term 'Rv2386c protein sequence' as used herein is meant the polypeptide sequence provided in SEQ ID No: 1 or a homologue thereof from a *Mycobacterium* species of the *tuberculosis* complex, e.g., a species such as *M. tuberculosis*, *M. bovis*, or *M. africanum*, or a *Mycobacterium* species that is environmental or opportunistic and that causes opportunistic infections such as lung infections in immune compromised hosts (e.g., patients with AIDS), e.g., BCG, *M. avium*, *M. intracellulare*, *M. celatum*, *M. genavense*, *M. haemophilum*, *M. kansasii*, *M. simiae*, *M. vaccae*, *M. fortuitum*, and *M. scrofulaceum* (see, e.g., *Harrison's Principles of Internal Medicine*, Chapter 150, pp. 953-966, 16th ed., Braunwald, et al., eds., 2005).

To ensure a high efficacy rate among vaccinated hosts, the components of a vaccine should be well conserved among the stains of clinical significance. Suitably, the Rv2386c protein is derived from *M. tuberculosis* H37Rv (i.e. the polypeptide sequence provided in SEQ ID No: 1) or a homologue thereof from another *M. tuberculosis* strain (such as CDC1551, F11, Haarlem A and C strains). Strains of *M. tuberculosis* which are associated with drug resistance (e.g. MDR or especially XDR) are a particularly valuable basis for the Rv2386c protein sequence. Strains of interest include:

CDC1551—transmissible and virulent strain

Haarlem family (such as Haarlem A)—Drug resistant strains found in crowded human populations. Members of the Haarlem family of *M. tuberculosis* strains have been found in many parts of the world. The first representative of the family was discovered in Haarlem, The Netherlands.

KZN4207—Drug sensitive isolate from patients in KwaZulu-Natal, South Africa

KZN1435—Multiple drug resistant (MDR) isolate from patients in KwaZulu-Natal, South Africa KZN605—Extensively drug resistant (XDR) isolate from patients in KwaZulu-Natal, South Africa C—Highly transmitted in New York City. In one study this strain was found to be more common among injection drug users and resistant to reactive nitrogen intermediates (Friedman et al. *J. Infect. Dis.* 1997 176(2):478-84)

94_M4241A—Isolated in San Francisco in 1994 from a patient born in China. This strain was previously analysed by genomic deletion analysis (Gagneux et al., *PNAS* 2006 103(8):2869-2873).

02_1987—Isolated in San Francisco in 2002 from a patient born in South Korea. This strain was previously analyzed by genomic deletion analysis (Gagneux et al., *PNAS* 2006 103(8):2869-2873).

T92—Isolated in San Francisco in 1999 from a patient born in The Philippines. This strain was published in Hirsh et al. *PNAS* 2004 101:4871-4876).

T85—Isolated in San Francisco in 1998 from a patient born in China. This strain was published in Hirsh et al. *PNAS* 2004 101:4871-4876).

EAS054—Isolated in San Francisco in 1993 from a patient born in India. This strain was previously analyzed by genomic deletion analysis (Gagneux et al., *PNAS* 2006 103(8):2869-2873).

Gagneux et al., *PNAS* 2006 103(8):2869-2873 and Herbert et al. Infect. Immun. 2007 75(12):5798-5805 provide valuable background on the range of *M. tuberculosis* strains which are known to exist.

Figure 2:
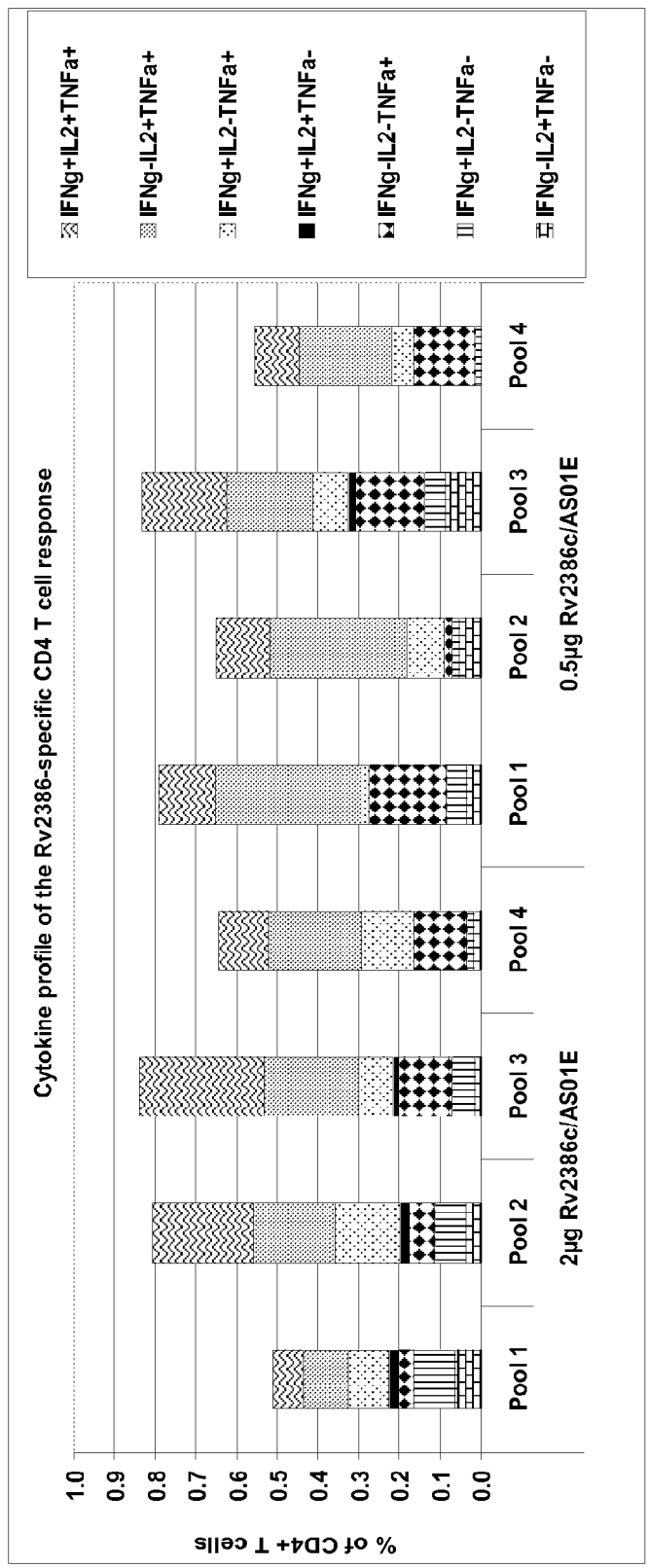
FIG. 2: Cytokine profile at day 21 (i.e. 7 days post second immunisation) of the antigen specific CD4 response in immunised CB6F1 mice.

Most suitably, the Rv2386c protein is selected from the polypeptide sequences provided in SEQ ID Nos: 1 and 3-7, in particular SEQ ID Nos: 1 and 3-6, such as SEQ ID No: 1.

Polynucleotides of particular interest are those comprising (such as consisting of) a sequence encoding:

(i) an Rv2386c protein sequence;

(ii) a variant of an Rv2386c protein sequence; or (iii) an immunogenic fragment of an Rv2386c protein sequence.

Polynucleotides will suitably comprise (such as consisting of) a variant of SEQ ID NO: 2 or fragment of SEQ ID NO: 2 which encodes an immunogenic fragment of an Rv2386c protein.

Combinations

The Rv2386c related polypeptides of the present invention can further comprise other components designed to enhance their immunogenicity or to improve these antigens in other respects. For example, improved isolation of the polypeptide antigens may be facilitated through the addition of a stretch of histidine residues (commonly known as a his-tag) towards one end of the antigen.

The term "his-tag" refers to a string of histidine residues, typically six residues, that are inserted within the reference sequence. To minimise disruption of the activity associated with the reference sequence, a his-tag is typically inserted at the N-terminus, usually immediately after the initiating methionine residue, or else at the C-terminus. They are usually heterologous to the native sequence but are incorporated since they facilitate isolation by improving the protein binding to immobilised metal affinity chromatography resins (IMAC). Generally speaking the presence or absence of a his-tag is not of significance from the point of view of eliciting a desirable immune response against the reference protein. However, to avoid the risk of an adverse reaction against the his-tag itself, it is considered best to minimise the length of the his-tag e.g. to four or fewer residues, in particular two residues (or to exclude the use of a his-tag entirely).

To improve the magnitude and/or breadth of the elicited immune response the compositions, polypeptides and nucleic acids of the invention can comprise multiple copies of the inventive antigen and/or additional heterologous polypeptides (or polynucleotides encoding them) from *Mycobacterium* species (in particular *M. tuberculosis*).

One skilled in the art will recognise that when a number of components are utilised in combination, the precise presentation can be varied. For example, a Rv2386c component and an additional copy of the inventive antigen or an additional heterologous antigen component could be presented:

(1) as two individual polypeptide components;

(2) as a fusion protein comprising both polypeptide components;

(3) as one polypeptide and one polynucleotide component;

(4) as two individual polynucleotide components;

(5) as a single polynucleotide encoding two individual polypeptide components; or (6) as a single polynucleotide encoding a fusion protein comprising both polypeptide components.

This flexibility applies equally to situations where three or more components are used in combination. However, for convenience, it is often desirable that when a number of components are present they are contained within a single fusion protein or a polynucleotide encoding a single fusion protein. In one embodiment of the invention all antigen components are provided as polypeptides (e.g. within a single fusion protein). In an alternative embodiment of the invention all antigen components are provided as polynucleotides (e.g. a single polynucleotide, such as one encoding a single fusion protein).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Fusion polypeptide" or "fusion protein" refers to a protein having at least two heterologous polypeptides (e.g. at least two *Mycobacterium* sp. polypeptides) covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, immunogenic fragments, and interspecies homologs of the antigens that make up the fusion protein. *Mycobacterium tuberculosis* antigens are described in Cole et al., *Nature* 393:537 (1998), which discloses the entire *Mycobacterium tuberculosis* genome. Antigens from other *Mycobacterium* species that correspond to *M. tuberculosis* antigens can be identified, e.g., using sequence comparison algorithms, as described herein, or other methods known to those of skill in the art, e.g., hybridisation assays and antibody binding assays.

The term "fused" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

Exemplary *M. tuberculosis* antigens which may be combined with Rv2386c include one or more of (e.g. 1 to 5, such as 1 to 3, in particular 1) the following (such as one or more of (i) to (xii)):

(i) Mtb8.4 (also known as DPV and Rv1174c), the polypeptide sequence of which is described in SEQ ID No: 102 of WO97/09428 (cDNA in SEQ ID No: 101) and in Coler et al *Journal of Immunology* 1998 161:2356-2364. Of particular interest is the mature Mtb8.4 sequence which is absent the leading signal peptide (i.e. amino acid residues 15-96 from SEQ ID No: 102 of WO97/09428). The full-length polypeptide sequence of Mtb8.4 is shown in SEQ ID No: 8;

(ii) Mtb9.8 (also known as MSL and Rv0287), the polypeptide sequence of which is described in SEQ ID No: 109 of WO98/53075 (fragments of MSL are disclosed in SEQ ID Nos: 110-124 of WO98/53075, SEQ ID Nos: 119 and 120 being of particular interest) and also in Coler et al *Vaccine* 2009 27:223-233 (in particular the reactive fragments shown in FIG. 2 therein). The full-length polypeptide sequence for Mtb9.8 is shown in SEQ ID No: 9;

(iii) Mtb9.9 (also known as Mtb9.9A, MTI, MTI-A and Rv1793) the polypeptide sequence of which is described in SEQ ID No: 19 of WO98/53075 and in Alderson et al *Journal of Experimental Medicine* 2000 7:551-559 (fragments of MTI are disclosed in SEQ ID Nos: 17 and 51-66 of WO98/53075, SEQ ID Nos: 17, 51, 52, 53, 56 and 62-65 being of particular interest). A number of polypeptide variants of MTI are described in SEQ ID Nos: 21, 23, 25, 27, 29 and 31 of WO98/53075 and in Alderson et al *Journal of Experimental Medicine* 2000 7:551-559. The full-length polypeptide sequence for Mtb9.9 is shown in SEQ ID No: 10;

(iv) Ra12 (also known as Mtb32A C-terminal antigen) the polypeptide sequence of which is described in SEQ ID No: 10 of WO01/98460 and in Skeiky et al *Journal of Immunology* 2004 172:7618-7682. The full-length polypeptide sequence for Ra12 is shown in SEQ ID No: 11;

(v) Ra35 (also known as Mtb32A N-terminal antigen) the polypeptide sequence of which is described in SEQ ID No: 8 of WO01/98460 and in Skeiky et al *Journal of Immunology* 2004 172:7618-7682. The full-length polypeptide sequence for Ra35 is shown in SEQ ID No: 12;

(vi) TbH9 (also known as Mtb39, Mtb39A, TbH9FL and Rv1196) the polypeptide sequence of which is described in SEQ ID No: 107 of WO97/09428, and also in Dillon et al *Infection and Immunity* 1999 67(6):2941-2950 and Skeiky et al *Journal of Immunology* 2004 172:7618-7682. The full-length polypeptide sequence for TbH9 is shown in SEQ ID No: 13;

(vii) Mtb40 (also known as HTCC1 and Rv3616c) the polypeptide sequence of which is described in SEQ ID No: 138 of WO98/53075 (cDNA in SEQ ID No: 137). The full-length polypeptide sequence for Mtb40 is shown in SEQ ID No: 14;

(viii) Mtb41 (also known as MTCC2 and Rv0915c) the polypeptide sequence of which is described in SEQ ID No: 142 of WO98/53075 (cDNA in SEQ ID No: 140) and in Skeiky et al *Journal of Immunology* 2000 165:7140-7149. The full-length polypeptide sequence for Mtb41 is shown in SEQ ID No: 15;

(ix) ESAT-6 (also known as esxA and Rv3875) the polypeptide sequence of which is described in SEQ ID No: 103 of WO97/09428 (cDNA in SEQ ID No: 104) and in Sorensen et al *Infection and Immunity* 1995 63(5):1710-1717. The full-length polypeptide sequence for ESAT-6 is shown in SEQ ID No: 16;

(x) Ag85 complex antigens (e.g. Ag85A, also known as fbpA and Rv3804c; or Ag85B, also known as fbpB and Rv1886c) which are discussed, for example, in Content et al *Infection and Immunity* 1991 59:3205-3212 and in Huygen et al *Nature Medicine* 1996 2(8):893-898. The full-length polypeptide sequence for Ag85A is shown in SEQ ID No: 17 (the mature protein of residues 43-338, i.e. lacking the signal peptide, being of particular interest). The full-length polypeptide sequence for Ag85B is shown in SEQ ID No: 18 (the mature protein of residues 41-325, i.e. lacking the signal peptide, being of particular interest);

(xi) Alpha-crystallin (also known as hspX and Rv2031c) which is described in Verbon et al *Journal of Bacteriology* 1992 174:1352-1359 and Friscia et al *Clinical and Experimental Immunology* 1995 102:53-57 (of particular interest are the fragments corresponding to residues 71-91, 21-40, 91-110 and 111-130). The full-length polypeptide sequence for alpha-crystallin is shown in SEQ ID No: 19;

(xii) Mpt64 (also known as Rv1980c) which is described in Roche et al *Scandinavian Journal of Immunology* 1996 43:662-670. The full-length polypeptide sequence for MPT64 is shown in SEQ ID No: 20 (the mature protein of residues 24-228, i.e. lacking the signal peptide, being of particular interest):

(xiii) Mtb32A, the polypeptide sequence of which is described in SEQ ID No: 2 (full-length) and residues 8-330 of SEQ ID No: 4 (mature) of WO01/98460, especially variants having at least one of the catalytic triad mutated (e.g. the catalytic serine residue, which may for example be mutated to alanine). The full-length polypeptide sequence for Mtb32A is shown in SEQ ID No: 21. The mature form of Mtb32A having a Ser/Ala mutation is shown in SEQ ID No: 22;

(xiv) TB10.4, the full-length polypeptide sequence for TB10.4 is shown in SEQ ID No: 23;

(xv) Rv1753c, the full-length polypeptide sequence for Rv1753c from *Mycobacterium tuberculosis* H37Rv is shown in SEQ ID No: 155; and/or (xvi) Rv2707c, the full-length polypeptide sequence for Rv2707c from *Mycobacterium tuberculosis* H37Rv is shown in SEQ ID No: 156.

or combinations thereof, such as (for example combinations such as (a) to (g)):

(a) a combination of Ra12, TbH9 and Ra35 components, for example in the form of a fusion protein, such as Mtb72f. The polypeptide sequence of Mtb72f is described in SEQ ID No: 6 of WO2006/117240 (cDNA in SEQ ID No: 5) and in Skeiky et al *Journal of Immunology* 2004 172:7618-7682 (where it incorporates an optional His-tag to aid purification, when utilised in the present invention suitably Mtb72f is absent the optional histidine residues). The polypeptide sequence for Mtb72f is shown in SEQ ID No: 24;

(b) a combination of Ra12, TbH9 and Ser/Ala mutated Ra35 (i.e. where the catalytic serine residue has been replaced with alanine) components, for example in the form of a fusion protein, such as M72. The polypeptide sequence of M72 is described in SEQ ID No: 4 of WO2006/117240 (cDNA in SEQ ID No: 3) where it incorporates an optional double histidine to aid manufacture, when utilised in the present invention M72 may also incorporate a double histidine though suitably M72 is absent the optional double histidine (i.e. residues 4-725 from SEQ ID No: 4 of WO2006/117240 are of particular interest). The polypeptide sequence for M72 is shown in SEQ ID No: 25;

(c) a combination of Mtb8.4, Mtb9.8, Mtb9.9 and Mtb41 components, for example in the form of a fusion protein, such as Mtb71f. The polypeptide sequence of Mtb71f is described in SEQ ID No: 16 of WO99/051748 (cDNA in SEQ ID No: 15), where it incorporates an optional His-tag to aid purification, when utilised in the present invention suitably Mtb71f corresponds to amino acid residues 9-710 of SEQ ID No:

16 from WO99/051748. The polypeptide sequence for Mtb71f is shown in SEQ ID No: 26;

(d) a combination of Mtb72f or M72 (suitably without optional histidine residues to aid expression) with Mtb9.8 and Mtb9.9, for example in a fusion protein. The polypeptide sequence for an M72-Mtb9.9-Mtb9.8 fusion is shown in SEQ ID No: 27 (M92 fusion), when used in the present invention, the M72-Mtb9.9-Mtb9.8 fusion may optionally incorporate a double histidine following the initiating methionine residue to aid manufacture;

(e) a combination of Mtb72f or M72 (suitably without optional histidine residues to aid expression) with Ag85B, for example in a fusion protein, such Mtb103f. The polypeptide sequence of Mtb103f is described in SEQ ID No: 18 of WO03/070187 (cDNA in SEQ ID No: 10), where it incorporates an optional His-tag to aid purification, when utilised in the present invention suitably Mtb103f corresponds to amino acid residues 8-1016 of SEQ ID No: 18 from WO03/070187. Also of particular interest is M103, i.e. Mtb103f incorporating a Ser/Ala mutation in the Ra35 component, when utilised in the present invention suitably M103 corresponds to amino acid residues 8-1016 of SEQ ID No: 18 from WO03/070187 wherein the Ser residue at position 710 has been replaced with Ala. The polypeptide sequence for M103 is shown in SEQ ID No: 28, when used in the present invention, the M72-Mtb9.9-Mtb9.8 fusion may optionally incorporate a double histidine following the initiating methionine residue to aid manufacture;

(f) a combination of Mtb72f or M72 (suitably without optional histidine residues to aid expression) with Mtb41, for example in a fusion protein, such Mtb114f. The polypeptide sequence of Mtb114f is described in SEQ ID No: 16 of WO03/070187 (cDNA in SEQ ID No: 9), where it incorporates an optional His-tag to aid purification, when utilised in the present invention suitably Mtb114f corresponds to amino acid residues 8-1154 of SEQ ID No: 16 from WO03/070187. Also of particular interest is M114, i.e. Mtb114f incorporating a Ser/Ala mutation in the Ra35 component, when utilised in the present invention suitably M114 corresponds to amino acid residues 8-1154 of SEQ ID No: 16 from WO03/070187 wherein the Ser residue at position 710 has been replaced with Ala. The polypeptide sequence for M114 is shown in SEQ ID No: 29, when used in the present invention, the M72-Mtb9.9-Mtb9.8 fusion may optionally incorporate a double histidine following the initiating methionine residue to aid manufacture;

(g) a combination of Ag85B and ESAT-6 components, such as in a fusion described in Doherty et al *Journal of Infectious Diseases* 2004 190:2146-2153; and/or (h) a combination of Ag85B and TB10.4 components, such as in a fusion described in Dietrich et al *Journal of Immunology* 2005 174(10):6332-6339 190:2146-2153.

Combinations of an Rv2386c component and an Mtb40 component are of particular interest. Obviously such combinations could optionally contain other additional antigen components (e.g. an M72 component).

Another combination of interest comprises an Rv2386c component and an M72 component.

A further combination of interest comprises an Rv2386c component and an Rv1753c component.

Other combinations of interest include those comprising an Rv2386c component and an Rv2707c component.

An additional combination of interest comprises an Rv2386c component and an alpha-crystallin component.

The skilled person will recognise that combinations need not rely upon the specific sequences described in above in (i)-(xvi) and (a)-(h), and that conservatively modified variants (e.g. having at least 70% identity, such as at least 80% identity, in particular at least 90% identity and especially at least 95% identity) or immunogenic fragments (e.g. at least 20% of the full length antigen, such as at least 50% of the antigen, in particular at least 70% and especially at least 80%) of the described sequences can be used to achieve the same practical effect.

Each of the above individual antigen sequences is also disclosed in Cole et al Nature 1998 393:537-544 and Camus Microbiology 2002 148:2967-2973. The genome of *M. tuberculosis* H37Rv is publicly available, for example at the Welcome Trust Sanger Institute website (available on the worldwide web at sanger.ac.uk/Projects/*M_tuberculosis*/) and elsewhere.

Many of the above antigens are also disclosed in U.S. patent application Ser. Nos. 08/523,435, 08/523,436, 08/658,800, 08/659,683, 08/818,111, 08/818,112, 08/942,341, 08/942,578, 08/858,998, 08/859,381, 09/056,556, 09/072,596, 09/072,967, 09/073,009, 09/073,010, 09/223,040, 09/287,849 and in PCT patent applications PCT/US98/10407, PCT/US98/10514, PCT/US99/03265, PCT/US99/03268, PCT/US99/07717, WO97/09428 and WO97/09429, WO98/16645, WO98/16646, each of which is herein incorporated by reference.

The compositions, polypeptides, and nucleic acids of the invention can also comprise additional polypeptides from other sources. For example, the compositions and fusion proteins of the invention can include polypeptides or nucleic acids encoding polypeptides, wherein the polypeptide enhances expression of the antigen, e.g., NS1, an influenza virus protein (see, e.g. WO99/40188 and WO93/04175). The nucleic acids of the invention can be engineered based on codon preference in a species of choice, e.g., humans (in the case of in vivo expression) or a particular bacterium (in the case of polypeptide production).

The Rv2386c component may also be administered with one or more chemotherapeutic agents effective against *tuberculosis* (e.g. *M. tuberculosis* infection). Examples of such chemotherapeutic agents include, but are not limited to, amikacin, aminosalicylic acid, capreomycin, cycloserine, ethambutol, ethionamide, isoniazid, kanamycin, pyrazinamide, rifamycins (i.e., rifampin, rifapentine and rifabutin), streptomycin, ofloxacin, ciprofloxacin, clarithromycin, azithromycin and fluoroquinolones. Such chemotherapy is determined by the judgment of the treating physician using preferred drug combinations. "First-line" chemotherapeutic agents used to treat *tuberculosis* (e.g. *M. tuberculosis* infection) that is not drug resistant include isoniazid, rifampin, ethambutol, streptomycin and pyrazinamide. "Second-line" chemotherapeutic agents used to treat *tuberculosis* (e.g. *M. tuberculosis* infection) that has demonstrated drug resistance to one or more "first-line" drugs include ofloxacin, ciprofloxacin, ethionamide, aminosalicylic acid, cycloserine, amikacin, kanamycin and capreomycin.

Conventional chemotherapeutic agents are generally administered over a relatively long period (ca. 9 months). Combination of conventional chemotherapeutic agents with the administration of a Rv2386c component according to the present invention may enable the chemotherapeutic treatment period to be reduced (e.g. to 8 months, 7 months, 6 months, 5 months, 4 months, 3 months or less) without a decrease in efficacy.

Of particular interest is the use of an Rv2386c component in conjunction with *Bacillus* Calmette-Guerin (BCG). For example, in the form of a modified BCG which recombinantly expresses Rv2386c (or a variant or fragment thereof as described herein). Alternatively, the Rv2386c component may be used to enhance the response of a subject to BCG vaccination, either by co-administration or by boosting a previous BCG vaccination. When used to enhance the response of a subject to BCG vaccination, the Rv2386c component may obviously be provided in the form of a polypeptide or a polynucleotide (optionally in conjunction with additional antigenic components as described above).

The skilled person will recognise that combinations of components need not be administered together and may be applied: separately or in combination; at the same time, sequentially or within a short period; though the same or through different routes. Nevertheless, for convenience it is generally desirable (where administration regimes are compatible) to administer a combination of components as a single composition.

The polypeptides, polynucleotides and compositions of the present invention will usually be administered to humans, but are effective in other mammals including domestic mammals (e.g., dogs, cats, rabbits, rats, mice, guinea pigs, hamsters, chinchillas) and agricultural mammals (e.g., cows, pigs, sheep, goats, horses).

Immunogenic Fragments

T cell epitopes are short contiguous stretches of amino acids which are recognised by T cells (e.g. CD4+ or CD8+ T cells). Identification of T cell epitopes may be achieved through epitope mapping experiments which are well known to the person skilled in the art (see, for example, Paul, *Fundamental Immunology*, 3rd ed., 243-247 (1993); Beißbarth et al *Bioinformatics* 2005 21(Suppl. 1):i29-i37).

Alternatively, epitopes may be predicted using the approaches discussed in the Examples.

As a result of the crucial involvement of the T cell response in *tuberculosis*, it is readily apparent that fragments of the full length Rv2386c polypeptide which contain at least one T cell epitope will be immunogenic and may contribute to immunoprotection. Such fragments are referred to herein as immunogenic fragments.

Immunogenic fragments according to the present invention will typically comprise at least 9 contiguous amino acids from the full length polypeptide sequence (e.g. at least 10), such as at least 12 contiguous amino acids (e.g. at least 15 or at least 20 contiguous amino acids), in particular at least 50 contiguous amino acids, such as at least 100 contiguous amino acids (for example at least 200 contiguous amino acids). Suitably the immunogenic fragments will be at least 20%, such as at least 50%, at least 70% or at least 80% of the length of the full length polypeptide sequence.

It will be understood that in a diverse out-bred population, such as humans, different HLA types mean that specific epitopes may not be recognised by all members of the population. Consequently, to maximise the level of recognition and scale of immune response to a polypeptide, it is generally desirable that an immunogenic fragment contains a plurality of the epitopes from the full length sequence (suitably all epitopes).

Particular fragments of the Rv2386c protein which may be of use include those containing at least one CD4+ epitope, suitably at least two CD4+ epitopes and especially all CD4+ epitopes (such as those epitopes described in the Examples and in SEQ ID Nos: 30-52, particularly those associated with a plurality of HLA alleles, e.g. those associated with 2, 3, 4, 5 or more alleles).

Other fragments of the Rv2386c protein which may be of use include those containing at least one CD8 epitope, suitably at least two CD8 epitopes and especially all CD8 epitopes (such as those epitopes described in the Examples and in SEQ ID Nos: 53-154, particularly those associated with a plurality of HLA alleles, e.g. those associated with 2, 3, 4, 5 or more alleles).

Where an individual fragment of the full length polypeptide is used, such a fragment is considered to be immunogenic where it elicits a response which is at least 20%, suitably at least 50% and especially at least 75% (such as at least 90%) of the activity of the reference sequence in an in vitro restimulation assay of PBMC or whole blood with specific antigens (e.g. restimulation for a period of between several hours to up to two weeks, such as up to one day, 1 day to 1 week or 1 to 2 weeks) that measures the activation of the cells via lymphoproliferation, production of cytokines in the supernatant of culture (measured by ELISA, CBA etc) or characterisation of T and B cell responses by intra and extracellular staining (e.g. using antibodies specific to immune markers, such as CD3, CD4, CD8, IL2, TNFα, IFNγ, CD40L, CD69 etc) followed by analysis with a flowcytometer. Suitably, a fragment is considered to be immunogenic where it elicits a response which is at least 20%, suitably at least 50% and especially at least 75% (such as at least 90%) of the activity of the reference sequence in a T cell proliferation and/or IFN-gamma production assay.

In some circumstances a plurality of fragments of the full length polypeptide (which may or may not be overlapping and may or may not cover the entirety of the full length sequence) may be used to obtain an equivalent biological response to the full length sequence itself. For example, at least two immunogenic fragments (such as three, four or five) as described above, which in combination provide at least 50%, suitably at least 75% and especially at least 90% activity of the reference sequence in an in vitro restimulation assay of PBMC or whole blood (e.g. a T cell proliferation and/or IFN-gamma production assay).

Variants

"Variants" or "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences.

Due to the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations lead to "silent" or "degenerate" variants, which are one species of conservatively modified variations. Every nucleic acid sequence herein which encodes a polypeptide also describes every possible silent variation of the nucleic acid. One of skill will recognise that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

A polynucleotide of the invention may contain a number of silent variations (for example, 1-50, such as 1-25, in particular 1-5, and especially 1 codon(s) may be altered) when compared to the reference sequence. A polynucleotide of the invention may contain a number of non-silent conservative variations (for example, 1-50, such as 1-25, in particular 1-5, and especially 1 codon(s) may be altered) when compared to the reference sequence. Non-silent variations are those which result in a change in the encoded amino acid sequence (either though the substitution, deletion or addition of amino acid residues). Those skilled in the art will recognise that a particular polynucleotide sequence may contain both silent and non-silent conservative variations.

In respect of variants of a protein sequence, the skilled person will recognise that individual substitutions, deletions or additions to polypeptide, which alters, adds or deletes a single amino acid or a small percentage of amino acids is a "conservatively modified variant" where the alteration(s) results in the substitution of an amino acid with a functionally similar amino acid or the substitution/deletion/addition of residues which do not substantially impact the biological function of the variant.

Conservative substitution tables providing functionally similar amino acids are well known in the art. Such conservatively modified variants are in addition to and do not exclude polymorphic variants, interspecies homologs, and alleles of the invention.

A polypeptide of the invention may contain a number of conservative substitutions (for example, 1-50, such as 1-25, in particular 1-10, and especially 1 amino acid residue(s) may be altered) when compared to the reference sequence. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Suitably such substitutions do not occur in the region of an epitope, and do not therefore have a significant impact on the immunogenic properties of the antigen.

Protein variants may also include those wherein additional amino acids are inserted compared to the reference sequence, for example, such insertions may occur at 1-10 locations (such as 1-5 locations, suitably 1 or 2 locations, in particular 1 location) and may, for example, involve the addition of 50 or fewer amino acids at each location (such as 20 or fewer, in particular 10 or fewer, especially 5 or fewer). Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Protein variants include those wherein amino acids have been deleted compared to the reference sequence, for example, such deletions may occur at 1-10 locations (such as 1-5 locations, suitably 1 or 2 locations, in particular 1 location) and may, for example, involve the deletion of 50 or fewer amino acids at each location (such as 20 or fewer, in particular 10 or fewer, especially 5 or fewer). Suitably such deletions do not occur in the region of an epitope, and do not therefore have a significant impact on the immunogenic properties of the antigen.

The skilled person will recognise that a particular protein variant may comprise substitutions, deletions and additions (or any combination thereof).

Methods of determining the epitope regions of an antigen are described and exemplified in the Examples.

Variants preferably exhibit at least about 70% identity, more preferably at least about 80% identity and most preferably at least about 90% identity (such as at least about 95%, at least about 98% or at least about 99%) to the associated reference sequence.

The terms "identical" or percent "identity," in the context of two or more nucleic acids or polypeptide sequences, refer to two or more sequences or sub-sequences that are the same or have a specified percentage of amino acid residues or nucleotides that are the same (i.e., 70% identity, optionally 75%, 80%, 85%, 90%, 95%, 98% or 99% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75-100 amino acids or nucleotides in length. Suitably, the comparison is performed over a window corresponding to the entire length of the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, references to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The present invention also extends to polynucleotides comprising a first nucleotide sequence which selectively hybridises under moderately stringent conditions (such as under highly stringent conditions) to the complement of a second nucleotide sequence which encodes a polypeptide comprising:
 (i) an Rv2386c protein sequence;
 (ii) a variant of an Rv2386c protein sequence; or
 (iii) an immunogenic fragment of an Rv2386c protein sequence.

The phrase "highly stringent hybridisation conditions" refers to conditions under which a probe will hybridise to its target subsequence, typically in a complex mixture of nucleic acid, but to no other sequences. Highly stringent conditions are sequence-dependent and will be different in different circumstances. Longer sequences hybridise specifically at higher temperatures. An extensive guide to the hybridisation of nucleic acids is found in Tijssen, *Techniques in Biochemistry and Molecular Biology—Hybridization with Nucleic Probes*, "Overview of principles of hybridisation and the strategy of nucleic acid assays" (1993). Generally, highly stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridise to the target sequence at equilibrium (as the target sequences are present in excess, at $T_m$, 50% of the probes are occupied at equilibrium). Highly stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Highly stringent conditions may also be achieved with the addition of destabilising agents such as formamide. For selective or specific hybridisation, a positive signal is at least two times background, optionally 10 times background hybridisation.

Exemplary highly stringent hybridisation conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridise to each other under highly stringent conditions are still functionally equivalent if the polypeptides which they encode are substantially identical. This occurs, for example, when a copy of a nucleic acid is created using the maximum codon degeneracy permitted by the genetic code. In such cases, the nucleic acids typically hybridise under moderately stringent hybridisation conditions.

Exemplary "moderately stringent hybridisation conditions" include a hybridisation in a buffer of 40% formamide, 1 M NaCl, 1% SDS at 37° C., and a wash in 1×SSC at 45° C. A positive hybridisation is at least twice background. Those of ordinary skill will readily recognise that alternative hybridisation and wash conditions can be utilised to provide conditions of similar stringency.

The phrase "selectively (or specifically) hybridises to" refers to the binding, duplexing, or hybridising of a molecule only to a particular nucleotide sequence under stringent hybridisation conditions when that sequence is present in a complex mixture (e.g., total cellular or library DNA or RNA).

In any event, variants of a polypeptide sequence will have essentially the same activity as the reference sequence (in the case of polynucleotides, variant polynucleotide sequences will encode a polypeptide which has essentially the same activity as the reference sequence). By essentially the same activity is meant at least 50%, suitably at least 75% and especially at least 90% activity of the reference sequence in an in vitro restimulation assay of PBMC or whole blood with specific antigens (e.g. restimulation for a period of between several hours to up to two weeks, such as up to one day, 1 day to 1 week or 1 to 2 weeks) that measures the activation of the cells via lymphoproliferation, production of cytokines in the supernatant of culture (measured by ELISA, CBA etc) or characterisation of T and B cell responses by intra and extracellular staining (e.g. using antibodies specific to immune markers, such as CD3, CD4, CD8, IL2, TNFa, IFNg, CD40L, CD69 etc) followed by analysis with a flowcytometer. Suitably, by essentially the same activity is meant at least 50%, suitably at least 75% and especially at least 90% activity of the reference sequence in a T cell proliferation and/or IFN-gamma production assay.

Polynucleotide Compositions

As used herein, the term "polynucleotide" refers to a molecule that has been isolated free of total genomic DNA of a particular species. Therefore, a polynucleotide encoding a polypeptide refers to a polynucleotide segment that contains one or more coding sequences yet is substantially isolated away from, or purified free from, total genomic DNA of the species from which the polynucleotide is obtained.

As will be understood by those skilled in the art, the polynucleotides of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the polynucleotide does not contain large portions of unrelated coding DNA, such as large chromosomal fragments or other functional genes or polypeptide coding regions. An isolated nucleic acid is separated from other open reading frames that flank the gene and encode proteins other than the gene. Of course, this refers to the DNA segment as originally isolated, and does not exclude genes or coding regions later added to the segment by the hand of man.

As will be recognised by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Mycobacterium* antigen or a portion thereof) or may comprise a variant, or a biological or functional equivalent of such a sequence. Polynucleotide variants may contain one or more substitutions, additions, deletions and/or insertions, as further described below, preferably such that the immunogenicity of the encoded polypeptide is not diminished, relative to the reference protein. The effect on the immunogenicity of the encoded polypeptide may generally be assessed as described herein.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 30, 40, 50, 75, 100, 150, 200, 300, 400, 500 or 1000 or more contiguous nucleotides of the reference sequence disclosed herein as well as all intermediate lengths there between. It will be readily understood that "intermediate lengths", in this context, means any length between the quoted values, such as 30, 31, 32, etc.; 50, 51, 52, 53, etc.; 100, 101, 102, 103, etc.; 150, 151, 152, 153, etc.; including all integers through 200-500; 500-1,000, and the like.

Moreover, it will be appreciated by those of ordinary skill in the art that, as a result of the degeneracy of the genetic code, there are many nucleotide sequences that encode a polypeptide as described herein. Some of these polynucleotides bear relatively low identity to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridisation, amplification and/or database sequence comparison).

Polynucleotide Identification and Characterisation

Polynucleotides may be identified, prepared and/or manipulated using any of a variety of well established techniques. For example, a polynucleotide may be identified, as described in more detail below, by screening a microarray of cDNAs. Such screens may be performed, for example, using a Synteni microarray (Palo Alto, Calif.) according to the manufacturer's instructions (and essentially as described by Schena et al., *Proc. Natl. Acad. Sci. USA* 93:10614-10619 (1996) and Heller et al., *Proc. Natl. Acad. Sci. USA* 94:2150-2155 (1997)). Alternatively, polynucleotides may be amplified from cDNA prepared from cells expressing the proteins described herein, such as *M. tuberculosis* cells. Such polynucleotides may be amplified via polymerase chain reaction (PCR). For this approach, sequence-specific primers may be designed based on the sequences provided herein, and may be purchased or synthesised.

An amplified portion of a polynucleotide may be used to isolate a full length gene from a suitable library (e.g., a *M. tuberculosis* cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridisation techniques, a partial sequence may be labeled (e.g., by nick-translation or end-labeling with $^{32}$P) using well known techniques. A bacterial or bacteriophage library is then generally screened by hybridising filters containing denatured bacterial colonies (or lawns containing phage plaques) with the labeled probe (see Sambrook et al., *Molecular Cloning: A Laboratory Manual* (2000)). Hybridising colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then be assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186 (1988)), which uses restriction enzymes to generate a fragment in the known region of the gene. The fragment is then circularised by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridises to a polyA region or vector sequence, to identify sequences that are 5' and 3' of a known sequence. Additional techniques include capture PCR (Lagerstrom et al., *PCR Methods Applic.* 1:111-19 (1991)) and walking PCR (Parker et al., *Nucl. Acids. Res.* 19:3055-60 (1991)). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

Polynucleotide sequences or fragments thereof which encode polypeptides, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

Natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognised by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesised, in whole or in part, using chemical methods well known in the art (see Caruthers, M. H. et al., *Nucl. Acids Res. Symp. Ser.* pp. 215-223 (1980), Horn et al., *Nucl. Acids Res. Symp. Ser.* pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., *Science* 269:202-204 (1995)) and automated synthesis may be achieved, for example, using the ABI 431A Peptide Synthesiser (Perkin Elmer, Palo Alto, Calif.).

A newly synthesised peptide may be substantially purified by preparative high performance liquid chromatography (e.g., Creighton, Proteins, Structures and Molecular Principles (1983)) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (2000), and Ausubel et al., *Current Protocols in Molecular Biology* (updated annually).

A variety of expression vector/host systems may be utilised to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503-5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. Other vectors containing constitutive or inducible promoters include GAP, PGK, GAL and ADH. For reviews, see Ausubel et al. (supra) and Grant et al., *Methods Enzymol.* 153:516-544 (1987) and Romas et al. *Yeast* 8 423-88 (1992).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in *McGraw Hill Yearbook of Science and Technology* pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells. Methods and protocols for working with adenovirus vectors are reviewed in Wold, *Adenovirus Methods and Protocols,* 1998. Additional references regarding use of adenovirus vectors can be found in *Adenovirus: A Medical Dictionary, Bibliography, and Annotated Research Guide to Internet References,* 2004.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-32 (1977)) and adenine phosphoribosyltransferase (Lowy et al., *Cell* 22:817-23 (1990)) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilise indole in place of tryptophan, or hisD, which allows cells to utilise histinol in place of histidine (Hartman & Mulligan, Proc. Natl. Acad. Sci. U.S.A. 85:8047-51 (1988)). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridisations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilising monoclonal antibodies reactive to two non-interfering epitopes on a given polypeptide may be preferred for some applications, but a competitive binding assay may also be employed. These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labelled hybridisation or PCR probes for detecting sequences related to polynucleotides include oligolabeling, nick translation, end-labelling or PCR amplification using a labelled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilised immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilised metal ion affinity chromatography) as described in Porath et al., *Prot. Exp. Purif.* 3:263-281 (1992) while the enterokinase cleavage site provides a means for purifying the desired polypeptide from the fusion protein. A discussion of vectors which contain fusion proteins is provided in Kroll et al., *DNA Cell Biol.* 12:441-453 (1993).

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesised.

The expression vector comprises a genetically engineered form of an adenovirus. Knowledge of the genetic organisation of adenovirus, a 36 kb, linear, double-stranded DNA virus, allows substitution of large pieces of adenoviral DNA with foreign sequences up to 7 kb (Grunhaus & Horwitz, *Semin. Virol.*, 3:237-252, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titre, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, *Radiother. Oncol.*, 19(3):197-218, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., *J. Gen. Virol.*, 36:59-74, 1977). Since the E3 region is dispensable from the adenovirus genome (Jones & Shenk, *Cell*, 13:181-188, 1978), the current adenovirus vectors, with the help of 293 cells, carry foreign DNA in either the E1, the D3 or both regions (Graham & Prevec, *Methods in Molecular Biology*, 7:109-128, 1991). In nature, adenovirus can package approximately 105% of the wild-type genome (Ghosh-Choudhury et al., *Biochemical and Biophysical Research Communications*, 147(3):964-973, 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, Science, 260:926-932, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Racher et al. (Racher et al., *Biotechnol. Prog.*, 11(5):575-583, 1995) have disclosed improved methods for culturing 293 cells and propagating adenovirus. In one format, natural cell aggregates are grown by inoculating individual cells into 1 liter siliconised spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (Karlsson et al., *The EMBO Journal*, 5(9):2377-2385, 1986) or in the E4 region where a helper cell line or helper virus complements the E4 defect.

Adenovirus is easy to grow and manipulate and exhibits broad host range in vitro and in vivo. This group of viruses can be obtained in high titres, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., *Am. Rev. Respir. Dis.* 88:394-403, 1963; Top et al., *J. Infect. Dis.*, 124(2):148-160, 1971), demonstrating their safety and therapeutic potential as in vivo gene transfer vectors.

Adenovirus vectors have been used in eukaryotic gene expression (Levrero et al., *Gene*, 101(2):195-202, 1991; Gomez-Foix et al., *Biotechniques*, 34(3):600-602, 1992) and vaccine development (Grunhaus & Horwitz, 1992; Graham & Prevec, 1991). Recently, animal studies suggested that recombinant adenovirus could be used for gene therapy (Stratford-Perricaudet & Perricaudet, *Science*, 252(5004): 431-434, 1991; Stratford-Perricaudet et al., *Hum. Gene Ther.*, 1(3):241-256, 1990; Rich et al., *Hum. Gene Ther.*, 4(4):461-476, 1993). Studies in administering recombinant adenovirus to different tissues include trachea instillation (Rosenfeld et al., *Science*, 252(5004):431-434, 1991; Rosenfeld et al., *Cell*, 68(1):143-155, 1992), muscle injection (Ragot et al., *Nature*, 361(6413):647-650, 1993), peripheral intravenous injections (Herz & Gerard, *Proc. Natl. Acad. Sci. USA*, 90(7):2812-2816, 1993) and stereotactic inoculation into the brain (Le Gal La Salle et al., *Science*, 259 (5097):988-990, 1993).

Adenovirus vectors may originate from human adenovirus. Alternatively they may originate from adenovirus of other species e.g. chimpanzee which may have the advantage that the viral vectors are not neutralised by antibodies against human adenovirus circulating in many human subjects (see e.g.: Tatsis N et al *Gene Therapy* 2006 13:421-429).

Adenovirus type 35, which is relatively uncommon and therefore there are low levels of pre-existing immunity to the vector itself, has been used as a delivery system in certain *tuberculosis* vaccines which are being developed (see for example, Radosevic et al *Infection and Immunity* 2007 75(8):4105-4115). Adenovirus type 35 may also be of particular value in the present invention as a delivery vector.

2. Retroviruses

The retroviruses are a group of single-stranded RNA viruses characterised by an ability to convert their RNA to double-stranded DNA in infected cells by a process of reverse-transcription (Coffin, *J. Med. Virol.*, 31(1):43-49, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., *Virology*, 196(1):57-69, 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas & Rubenstein, *Biotechnology*, 10:493-513, 1988; Temin, *Cell Biophys.*, 9(1-2):9-16, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., *Virology*, 67(1):242-8, 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., *Proc. Natl. Acad. Sci. USA.*, 86(23):9079-9083, 1989). Using antibodies against major histocompatibility complex class I and class II antigens, they demonstrated the infection of a variety of human cells that bore those surface antigens with an ecotropic virus in vitro (Roux et al., 1989).

3. Adeno-Associated Viruses

AAV (Ridgeway, *FEMS Microbiol. Immunol.*, (3):157-62, 1988; Hermonat & Muzycska, *Proc. Nat. Acad. Sci. USA*, 81:6466-6470, 1984) is a parovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Five serotypes have been isolated, of which AAV-2 is the best characterised.

AAV has a single-stranded linear DNA that is encapsidated into capsid proteins VP1, VP2 and VP3 to form an icosahedral virion of 20 to 24 nm in diameter (Muzyczka & McLaughlin, *J. Virol.* 62(6):1963-1973, 1988).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat & Muzyczka, 1984).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering antisense constructs.

AAV is also a good choice of delivery vehicles due to its safety. There is a relatively complicated rescue mechanism: not only wild type adenovirus but also AAV genes are required to mobilise rAAV. Likewise, AAV is not pathogenic and not associated with any disease. The removal of viral coding sequences minimises immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., *Gene,* 15:68(1):1-10, 1988), lentiviruses, polio viruses and herpes viruses may be employed. Other poxvirus derived vectors, such as fowl-pox derived vectors, may also be expected to be of use. They offer several attractive features for various mammalian cells (Friedmann, *Mol. Biol. Med.,* 6(2):117-125, 1989; Ridgeway, 1988; Coupar et al., 1988; Horwich et al., *J. Virol.* 64(2):642-50, 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (Chang et al., *Immunogenetics,* 33(3):171-177, 1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titres of the recombinant virus were used to infect primary duckling hepatocytes. Stable CAT gene expression was detected for at least 24 days after transfection (Chang et al., 1991).

Additional 'viral' vectors include virus like particles (VLPs) and phages.

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronisation with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed, for example, by any method which physically or chemically permeabilises the cell membrane. This is particularly applicable for transfer in vitro but it may be applied to in vivo use as well. Dubensky et al. (Dubensky et al., *J. Virol.* 50(3):779-83, 1984) successfully injected polyomavirus DNA in the form of calcium phosphate precipitates into liver and spleen of adult and newborn mice demonstrating active viral replication and acute infection. Benvenisty & Reshef (Benvenisty & Reshef, *Proc. Natl. Acad. Sci. USA,* 83(24):9551-9555, 1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., *J. Virol.,* 61(5):1552-1558, 1987). Several devices for accelerating small particles have been developed. One such device relies on a high voltage discharge to generate an electrical current, which in turn provides the motive force (Yang et al., *Proc. Natl. Acad. Sci. USA,* 87(24):9568-9572, 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., *FEBS Lett.* 287(1-2):118-20, 1991). This may require surgical exposure of the tissue or cells, to eliminate any intervening tissue between the gun and the target organ, i.e., ex vivo treatment. Again, DNA encoding a particular gene may be delivered via this method and still be incorporated.

Bacteria may also be utilised as a delivery method (e.g. *listeria,* see WO2004/11048) and in particular BCG.

Polypeptide Compositions

The present invention, in other aspects, provides polypeptide compositions.

Generally, a polypeptide of the invention will be an isolated polypeptide (i.e. separated from those components with which it may usually be found in nature).

For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Polypeptides of the invention, immunogenic fragments thereof, and other variants having less than about 100 amino acids, and generally less than about 50 amino acids, may also be generated by synthetic means, using techniques well known to those of ordinary skill in the art. For example, such polypeptides may be synthesised using any of the commercially available solid-phase techniques, such as the Merrifield solid-phase synthesis method, where amino acids are sequentially added to a growing amino acid chain. See Merrifield, *J. Am. Chem. Soc.* 85:2149-2146 (1963). Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, examples of such proteins include tetanus, *tuberculosis* and hepatitis proteins (see, e.g., Stoute et al., *New Engl. J. Med.* 336:86-91 (1997)). A fusion partner may, for example, assist in providing T helper epitopes (an immunological fusion partner), preferably T helper epitopes recognised by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46 (1985); Murphy et al., *Proc. Natl. Acad. Sci. USA* 83:8258-8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

T Cells

Immunotherapeutic compositions may also, or alternatively, comprise T cells specific for a *Mycobacterium* antigen. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide of the invention, polynucleotide encoding such a polypeptide, and/or an antigen presenting cell (APC) that expresses such a polypeptide. Such stimulation is performed under conditions and for a time sufficient to permit the generation of T cells that are specific for the polypeptide. Preferably, the polypeptide or polynucleotide is present within a delivery vehicle, such as a microsphere, to facilitate the generation of specific T cells.

T cells are considered to be specific for a polypeptide of the invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labelling cultures of T cells with tritiated thymidine and measuring the amount of tritiated thymidine incorporated into DNA). Contact with a polypeptide of the invention (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a polypeptide, polynucleotide or polypeptide-expressing APC may be $CD4^+$ and/or $CD8^+$. Protein-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a polypeptide, polynucleotide or APC can be expanded in number either in vitro or in vivo. Proliferation of such T cells in vitro may be accomplished in a variety of ways. For example, the T cells can be re-exposed to a polypeptide, or a short peptide corresponding to an immunogenic portion of such a polypeptide, with or without the addition of T cell growth factors, such as interleukin-2, and/or stimulator cells that synthesise a polypeptide. Alternatively, one or more T cells that proliferate in the presence of the protein can be expanded in number by cloning. Methods for cloning cells are well known in the art, and include limiting dilution.

Pharmaceutical Compositions

In additional embodiments, the polynucleotide, polypeptide, T-cell and/or antibody compositions disclosed herein will be formulated in pharmaceutically-acceptable or physiologically-acceptable solutions for administration to a cell or an animal, either alone, or in combination with one or more other modalities of therapy.

It will also be understood that, if desired, the nucleic acid segment (e.g., RNA or DNA) that expresses a polypeptide as disclosed herein may be administered in combination with other agents as well, such as, e.g., other proteins or polypeptides or various pharmaceutically-active agents, including chemotherapeutic agents effective against a *M. tuberculosis* infection. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesised as described herein. Likewise, such compositions may further comprise substituted or derivatised RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation. Other routes of administration include via the mucosal surfaces.

Typically, formulations comprising a therapeutically effective amount deliver about 0.1 ug to about 1000 ug of polypeptide per administration, more typically about 2.5 ug to about 100 ug of polypeptide per administration. In respect of polynucleotide compositions, these typically deliver about 10 ug to about 20 mg of the inventive polynucleotide per administration, more typically about 0.1 mg to about 10 mg of the inventive polynucleotide per administration.

Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., *Nature*, 386(6623): 410-414, 1997; Hwang et al., *Adv. Drug Deliv. Rev.* 32:139-152, 1998; U.S. Pat. No. 5,641,515; U.S. Pat. No. 5,580,579 and U.S. Pat. No. 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavouring agent, such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active component, sucrose as a sweetening agent methyl and propylparabens as preservatives, a dye and flavouring, such as cherry or orange flavour. Of course, any material used in preparing any dosage unit form should be pharmaceutically pure and substantially non-toxic in the amounts employed. In addition, the active components may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, intradermally, or even intraperitoneally as described in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal and Buccal Delivery

In certain embodiments, the pharmaceutical compositions may be delivered by intranasal sprays, buccal sprays, inhalation, and/or other aerosol delivery vehicles. Methods for delivering genes, nucleic acids, and peptide compositions directly to the lungs eg via nasal and buccal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., *J. Control. Release*, 52(1-2):81-87, 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., *FEBS Lett.* 84(2):323-326, 1977; Couvreur, *Crit. Rev. Ther. Drug. Carrier Syst.*, 5(1):1-20, 1988; Lasic, *Trends Biotechnol.*, 16(7):307-321, 1998; which describes the use of liposomes and nanocapsules in the targeted antibiotic therapy for intracellular bacterial infections and diseases). Recently, liposomes were developed with improved serum stability and circulation half-times (Gabizon & Papahadjopoulos, *Proc. Natl. Acad. Sci. USA* 85(18):6949-6953, 1988; Allen and Choun, *FEBS Lett.*, 223:42-46, 1987; U.S. Pat. No. 5,741,516, specifically incorporated herein by reference in its entirety). Further, various methods of liposome and liposome like preparations as potential drug carriers have been reviewed (Takakura, *Nihon Rinsho.*, 56(3):691-695, 1998; Chandran et al., *Indian J. Exp. Biol.*, 35(8):801-809, 1997; Margalit, *Crit. Rev. Ther. Drug Carrier Syst.*, 12(2-3):233-261, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., *J. Biol. Chem.*, 265(27):16337-16342, 1990; Muller et al., *DNA Cell Biol.*, 9(3):221-229, 1990). In addition, liposomes are free of the DNA length constraints that are typical of viral-based delivery systems. Liposomes have been used effectively to introduce genes, drugs (Heath & Martin, Chem. Phys. Lipids, 40(2-4):347-358, 1986; Heath et al., *Biochim. Biophys. Acta.*, 862(1):72-80, 1986; Balazsovits et al., *Cancer Chemother. Pharmacol.*, 23(2):81-86, 1989; Fresta & Puglisi, *J. Drug Target.*, 4(2):95-101, 1996), radiotherapeutic agents (Pikul et al., *Arch. Surg.*, 122(12):1417-1420, 1987), enzymes (Imaizumi et al., *Stroke*, 21(9):1312-1317, 1990a; Imaizumi et al., *Acta. Neurochir. Suppl.* (Wien), 51:236-238, 1990b), viruses (Faller & Baltimore, *J. Virol.*, 49(1):269-72, 1984), transcription factors and allosteric effectors (Nicolau & Gersonde, *Naturwissenschaften.*, 66(11):563-566, 1979) into a variety of cultured cell lines and animals. In addition, several successful clinical trails examining the effectiveness of liposome-mediated drug delivery have been completed (Lopez-Berestein et al., *J. Infect. Dis.*, 151(4):704-710, 1985a; 1985b; Coune, *Infection*, 16(3):141-147, 1988; Sculier et al., *Eur. J. Cancer Clin. Oncol.*, 24(3):527-538, 1988). Furthermore, several studies suggest that the use of liposomes is not associated with autoimmune responses, toxicity or gonadal localization after systemic delivery (Mon & Fukatsu, Epilepsia, 33(6):994-1000, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behaviour limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., *Journal of Pharmacy and Pharmacology*, 39(12):973-977, 1987; Quintanar-Guerrero et al., *Drug Dev. Ind. Pharm.* 24(12):1113-1128, 1998; Douglas et al., *Crit. Rev. Ther. Drug Carrier Syst.*, 3(3):233-261, 1987). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., *J. Pharm. Sci.*, 69(2):199-202, 1980; 1988; zur Muhlen et al., *Eur. J. Pharm. Biopharm.*, 45(2):149-155, 1998; Zambaux et al., *J. Control. Release*. 50(1-3):31-40, 1998; Pinto-Alphandry et al., *J. Drug Target.*, 3:167-169, 1995 and U.S. Pat. No. 5,145,684, specifically incorporated herein by reference in its entirety).

Skin patches may also be utilised for transcutaneous delivery.

Immunogenic Compositions

In certain preferred embodiments of the present invention, immunogenic compositions are provided. The immunogenic compositions will generally comprise one or more polypeptides or polynucleotides, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877).

Preparation of immunogenic compositions is generally described in, for example, Powell & Newman, eds., *Vaccine Design* (the subunit and adjuvant approach) (1995). Pharmaceutical compositions and immunogenic compositions within the scope of the present invention may also contain other compounds, which may be biologically active or inactive. For example, one or more immunogenic portions of other *M. tuberculosis* antigens may be present, either incorporated into a fusion polypeptide or as a separate compound, within the pharmaceutical or immunogenic composition.

Illustrative immunogenic compositions may contain a polynucleotide (e.g. DNA) encoding one or more of the polypeptides as described above, such that the polypeptide is generated in situ (thereby eliciting an immune response). As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198 (1998), and references cited therein. Appropriate nucleic acid expression systems contain the necessary DNA sequences for expression in the patient (such as a suitable promoter and terminating signal). Bacterial delivery systems involve the administration of a bacterium host cell (for example, a *Mycobacterium*, *Bacillus* or *Lactobacillus* strain, including *Bacillus*-Calmette-Guerrin or *Lactococcus lactis*) that expresses the polypeptide (e.g. on its cell surface or secretes the polypeptide) (see, for example, Ferreira, et al., *An Acad Bras Cienc* (2005) 77:113-124; and Raha, et al., *Appl Microbiol Biotechnol* (2005) PubMedID 15635459). In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321 (1989); Flexner et al., *Ann. N.Y. Acad. Sci.* 569:86-103 (1989); Flexner et al., *Vaccine* 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627 (1988); Rosenfeld et al., *Science* 252:431-434 (1991); Kolls et al., *Proc. Natl. Acad. Sci. USA* 91:215-219 (1994); Kass-Eisler et al., *Proc. Natl. Acad. Sci. USA* 90:11498-11502 (1993); Guzman et al., *Circulation* 88:2838-2848 (1993); and Guzman et al., *Cir. Res.* 73:1202-1207 (1993). Techniques for incorporating DNA into such expression systems are well known to those of ordinary skill in the art. The DNA may also be "naked," as described, for example, in Ulmer et al., *Science* 259:1745-1749 (1993) and reviewed by Cohen, *Science* 259:1691-1692 (1993). The uptake of naked DNA may be increased by coating the DNA onto biodegradable beads, which are efficiently transported into the cells. It will be apparent that a immunogenic composition may comprise both a polynucleotide and a polypeptide component. Such immunogenic composition may provide for an enhanced immune response.

It will be apparent that an immunogenic composition may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the immunogenic compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the immunogenic compositions of this invention. For example, an adjuvant may be included. Most adjuvants contain a substance designed to protect the antigen from rapid catabolism, such as aluminium hydroxide or mineral oil, and a stimulator of immune responses, such as lipid A, *Bortadella pertussis* or *Mycobacterium* species or *Mycobacterium* derived proteins. For example, delipidated, deglycolipidated *M. vaccae* ("pVac") can be used. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS01B, AS02A, AS15, AS-2 and derivatives thereof (GlaxoSmithKline, Philadelphia, Pa.); CWS (cell wall skeleton from a tubercule *bacillus*), TDM (trehalose dicorynomycolate), Leif (Leishmania elongation initiation factor), aluminium salts such as aluminium hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A (MPL®); and quil A (e.g. QS-21). Cytokines, such as GM-CSF or interleukin-2, -7, or -12, may also be used as adjuvants.

An adjuvant refers to the components in a vaccine or therapeutic composition that increase the specific immune response to the antigen (see, e.g., Edelman, *AIDS Res. Hum Retroviruses* 8:1409-1411 (1992)). Adjuvants induce immune responses of the Th1-type and Th-2 type response. Th1-type cytokines (e.g., IFN-γ, IL-2, and IL-12) tend to favour the induction of cell-mediated immune response to an administered antigen, while Th-2 type cytokines (e.g., IL-4, IL-5, 11-6, IL-10) tend to favour the induction of humoral immune responses. Adjuvants capable of preferential stimulation of a Th-1 cell-mediated immune response are described in WO 94/00153 and WO 95/17209.

Within the immunogenic compositions provided herein, the adjuvant composition is preferably designed to induce an immune response predominantly of the Th1 type. Following application of a immunogenic composition as provided herein, a patient will typically support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Janeway, et al., *Immunobiology*, 5$^{th}$ Edition, 2001.

The Rv2386c compositions usually comprise one or more adjuvants, e.g., AS01B (3-de-O-acylated monophosphoryl lipid A (3D-MPL®) and QS21 in a liposome formulation; see, U.S. Patent Publication No. 2003/0143240); AS02A (3D-MPL® and QS21 and an oil in water emulsion; see, Bojang, et al., *Lancet* (2001) 358:1927); ENHANZYN® (Detox); 3D-MPL®; saponins including Quil A and its components e.g. QS21 and saponin mimetics; CWS (cell wall skeleton from a tubercule *bacillus*); TDM (trehalose dicorynomycolate); aminoalkyl glucosaminide 4-phosphates (AGPs); immunostimulatory oligonucleoptides e.g. CPG; Leif (Leishmania elongation initiation factor); and derivatives thereof. In a preferred embodiment, an Rv2386c polypeptide is administered with one or more adjuvants selected from the group consisting of 3D-MPL® and QS21 in a liposome formulation eg AS01B and 3D-MPL® and QS21 and an oil in water emulsion (e.g. AS02A). Adjuvant systems AS01B and AS02A are further described in Pichyangkul, et al., *Vaccine* (2004) 22:3831-40.

When delivering the Rv2386c antigen as a nucleic acid, it can be delivered, for example, in a viral vector (i.e., an adenovirus vector), or in a mutant bacterium host cell (i.e., a mutant, avirulent *Mycobacterium, Lactobacillus* or *Bacillus* host cell including *Bacillus* Calmette-Guerin (BCG) and *Lactococcus lactis*).

Preferred adjuvants for use in eliciting a predominantly Th1-type response include, for example, a combination of monophosphoryl lipid A (MPL®), preferably 3-O-deacylated monophosphoryl lipid A (3D-MPL®), optionally with an aluminium salt (see, for example, Ribi, et al., 1986, Immunology and Immunopharmacology of Bacterial Endotoxins, Plenum Publ. Corp., NY, pp. 407-419; GB 2122204B; GB 2220211; and U.S. Pat. No. 4,912,094). A preferred form of 3D-MPL® is in the form of an emulsion having a small particle size less than 0.2 mm in diameter, and its method of manufacture is disclosed in WO 94/21292. Aqueous formulations comprising monophosphoryl lipid A and a surfactant have been described in WO 98/43670. Exemplified preferred adjuvants include AS01B (MPL® and QS21 in a liposome formulation), 3D-MPL® and QS21 in a liposome formulation, AS02A (MPL® and QS21 and an oil in water emulsion), 3D-MPL® and QS21 and an oil in water emulsion, and AS15, available from GlaxoSmithKline. MPL® adjuvants are available from GlaxoSmithKline (see U.S. Pat. Nos. 4,436,727; 4,877,611; 4,866,034 and 4,912,094).

CpG-containing oligonucleotides (in which the CpG dinucleotide is unmethylated) also induce a predominantly Th1 response. CpG is an abbreviation for cytosine-guanosine dinucleotide motifs present in DNA. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). CpG when formulated into immunogenic compositions, is generally administered in free solution together with free antigen (WO 96/02555; McCluskie and Davis, supra) or covalently conjugated to an antigen (WO 98/16247), or formulated with a carrier such as aluminium hydroxide ((Hepatitis surface antigen) Davis et al. supra; Brazolot-Millan et al., Proc. Natl. Acad. Sci., USA, 1998, 95(26), 15553-8). CpG is known in the art as being an adjuvant that can be administered by both systemic and mucosal routes (WO 96/02555, EP 468520, Davis et al., *J. Immunol*, 1998, 160(2):870-876; McCluskie and Davis, *J. Immunol.*, 1998, 161(9):4463-6).

Another preferred adjuvant is a saponin or saponin mimetics or derivatives, such as Quil A, preferably QS21 (Aquila Biopharmaceuticals Inc., Framingham, Mass.), which may be used alone or in combination with other adjuvants. For example, an enhanced system involves the combination of a monophosphoryl lipid A (MPL®) and saponin derivative, such as the combination of QS21 and 3D-MPL® as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL® and tocopherol in an oil-in-water emulsion is described in WO 95/17210. Additional saponin adjuvants of use in the present invention include QS7 (described in WO 96/33739 and WO 96/11711) and QS17 (described in U.S. Pat. No. 5,057,540 and EP 0 362 279 B1).

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOM®s. Furthermore, the saponins may be formulated together with a polyoxyethylene ether or ester, in either a non-particulate solution or suspension, or in a particulate structure such as a paucilamelar liposome or ISCOM®. The saponins may also be formulated with excipients such as CARBOPOL® to increase viscosity, or may be formulated in a dry powder form with a powder excipient such as lactose.

In one embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol containing liposomes, as described in WO 96/33739. Other suitable formulations comprise an oil-in-water emulsion and tocopherol. Another suitable adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 as disclosed in WO 00/09159. Suitably the formulation additionally comprises an oil in water emulsion and tocopherol.

Other suitable adjuvants include MONTANIDE® ISA 720 (Seppic, France), SAF (Chiron, Calif., United States), ISCOMS® (CSL), MF-59 (Chiron), the SBAS series of adjuvants (SmithKline Beecham, Rixensart, Belgium), Detox (Corixa), RC-529 (Corixa) and other aminoalkyl glucosaminide 4-phosphates (AGPs), such as those described in pending U.S. patent application Ser. Nos. 08/853,826 and 09/074,720 (U.S. Pat. Nos. 6,113,918 and 6,355,257, respectively), the disclosures of which are incorporated herein by reference in their entireties, and polyoxyethylene ether adjuvants such as those described in WO 99/52549A1. SmithKline Beecham and Corixa Corporation are now part of GlaxoSmithKline.

Other suitable adjuvants include adjuvant molecules of the general formula (I):

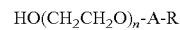

HO(CH$_2$CH$_2$O)$_n$-A-R wherein, n is 1-50, A is a bond or —C(O)—, R is C$_{1-50}$ alkyl or Phenyl C$_{1-50}$ alkyl.

A further adjuvant of interest is shiga toxin b chain, used for example as described in WO2005/112991.

One embodiment of the present invention consists of an immunogenic composition comprising a polyoxyethylene ether of general formula (I), wherein n is between 1 and 50, preferably 4-24, most preferably 9; the R component is C$_{1-50}$, preferably C$_4$-C$_{20}$ alkyl and most preferably C$_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12$^{th}$ edition: entry 7717). These adjuvant molecules are described in WO 99/52549.

Any immunogenic composition provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429-1438 (1996)) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly (lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release.

Any of a variety of delivery vehicles may be employed within pharmaceutical compositions and immunogenic compositions to facilitate production of an antigen-specific immune response. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response and/or to be immunologically compatible with the receiver (i.e., matched HLA haplotype). APCs may generally be isolated from any of a variety of biological fluids and organs, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau & Steinman, *Nature* 392:245-251 (1998)) and have been shown to be effective as a physiological adjuvant for eliciting prophylactic or therapeutic immunity (see Timmerman & Levy, *Ann. Rev. Med.* 50:507-529 (1999)). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within an immunogenic composition (see Zitvogel et al., *Nature Med.* 4:594-600 (1998)).

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorised as "immature" and "mature" cells, which allows a simple way to discriminate between two well characterised phenotypes. However, this nomenclature should not be construed to exclude all possible intermediate stages of differentiation. Immature dendritic cells are characterised as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1 BB).

APCs may generally be transfected with a polynucleotide encoding a protein (or portion or other variant thereof) such that the polypeptide, is expressed on the cell surface. Such transfection may take place ex vivo, and a pharmaceutical composition or immunogenic composition comprising such transfected cells may then be used, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and Cell Biology* 75:456-460 (1997). Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Immunogenic compositions and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, an immunogenic composition or pharmaceutical composition may be stored in a freeze-dried condition requiring only the addition of a sterile liquid carrier immediately prior to use.

In some embodiments, a "priming" or first administration of an Rv2386c polypeptide (including variants, immunogenic fragments or fusion proteins), or polynucleotide encoding said polypeptide, is followed by one or more "boosting" or subsequent administrations of an Rv2386c polypeptide (including variants, immunogenic fragments or fusion proteins) or polynucleotide encoding said polypeptide ("prime and boost" method). For instance, a first administration with an Rv2386c polypeptide (including variants, immunogenic fragments or fusion proteins) or polynucleotide encoding said polypeptide is followed by one or more subsequent administrations of an Rv2386c polypeptide (including variants, immunogenic fragments or fusion proteins) or polynucleotide encoding said polypeptide.

In one embodiment, a first administration with an Rv2386c polypeptide or polynucleotide is followed by one or more subsequent administrations of an Rv2386c polypeptide. In one embodiment, a first administration with an Rv2386c polypeptide or polynucleotide is followed by one or more subsequent administrations of an Rv2386c polynucleotide. Usually the first or "priming" administration and the second or "boosting" administration are given about 2-12 weeks apart, or up to 4-6 months apart. Subsequent "booster" administrations are given about 6 months apart, or as long as 1, 2, 3, 4 or 5 years apart. Conventional booster treatment (e.g., a protein priming administration followed by a protein boosting administration) may also useful be in preventing or treating *tuberculosis* (e.g. preventing or treating latent *tuberculosis*, in particular preventing or delay *tuberculosis* reactivation).

Antibodies

"Antibody" refers to a polypeptide comprising a framework region from an immunoglobulin gene or fragments thereof that specifically binds and recognises an antigen. The recognised immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterised fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesised de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanised antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) and *Using Antibodies: A Laboratory Manual* (1998), for a description of immunoassay formats and conditions that can be used to determine specific immunoreactivity). Typically a specific or selective reaction will be at least twice background signal or noise and more typically more than 10, 20 or 100 times background (e.g. binding to other *Mycobacterium* proteins, such as other *Mycobacterium tuberculosis* proteins).

Diagnostics

In another aspect, this invention provides methods for using one or more of the polypeptides described above to diagnose *tuberculosis* (for example using T cell response based assays or antibody based assays of conventional format).

For example, there is provided a method for determining prior *M. tuberculosis* infection in an individual comprising:
 (a) obtaining a sample from the individual;
 (b) contacting said sample with an isolated polypeptide which comprises:
  (i) an Rv2386c protein sequence;
  (ii) a variant of an Rv2386c protein sequence; or
  (iii) an immunogenic fragment of an Rv2386c protein sequence;
 (c) quantifying the sample response.

The sample may for example be whole blood or purified cells. Suitably the sample will contain peripheral blood mononucleated cells (PBMC). In one embodiment of the invention the individual will be seropositive. In a second embodiment of the invention the individual will be seronegative.

Suitably the individual will not previously have been vaccinated against *M. tuberculosis* infection (e.g. suitably the individual will not previously have been vaccinated with BCG).

The sample response may be quantified by a range of means known to those skilled in the art, including the monitoring of lymphocyte proliferation or the production of specific cytokines or antibodies. For example, T-cell ELISPOT may be used to monitor cytokines such as interferon gamma (IFNγ), interleukin 2 (IL2) and interleukin 5 (IL5). B-cell ELLISPOT may be used to monitor the stimulation of *M. tuberculosis* specific antigens. The cellular response may also be characterised by the use of by intra- and extra-cellular staining and analysis by a flow cytometer.

Methods of quantifying a sample proliferation response include:
  (i) pulsing cultured cells with a radiolabel (e.g. tritiated thymidine) and monitoring tritium uptake (e.g. gas scintillation);
  (ii) carboxyfluorsecein diacetate succinimidyl ester (CFSE) labelling and fluorescence monitoring of cell division using flow cytometry.

Quantifying a sample cytokine response includes in particular the monitoring of interferon gamma production.

When using such quantification methods, a positive response to an antigen may be defined by a signal to noise ratio (S/N ratio) of at least 2:1 (for example, at least 3:1 or at least 5:1).

In a further aspect of the present invention methods are provided to diagnose *M. tuberculosis* infection using a skin test. As used herein, a "skin test" is any assay performed directly on a patient in which a delayed-type hypersensitivity (DTH) reaction (such as swelling, reddening or dermatitis) is measured following intradermal injection of an Rv153c polypeptide as described above (or variant, immunogenic fragments thereof or nucleotides encoding them). Such injection may be achieved using any suitable device sufficient to contact the antigen combinations with dermal cells of the patient, such as a tuberculin syringe or 1 mL syringe. The reaction is measured after a period of time, for example at least 48 hours after injection, especially 48-72 hours.

The DTH reaction is a cell-mediated immune response, which is greater in patients that have been exposed previously to the test antigen. The response may be measured visually, using a ruler. In general, a response that is greater than about 0.5 cm in diameter, especially greater than about 1.0 cm in diameter, is a positive response, indicative of prior *M. tuberculosis* infection, which may or may not be manifested as an active disease.

For use in a skin test, the Rv2386c component is suitably formulated as a pharmaceutical composition containing a physiologically acceptable carrier. Suitably, the carrier employed in such pharmaceutical compositions is a saline solution with appropriate preservatives, such as phenol and/or Tween™ 80.

The present invention further provides kits for use within any of the above diagnostic methods. Such kits typically comprise two or more components necessary for performing a diagnostic assay. Components may be compounds, reagents, containers and/or equipment.

For example, one container within a kit may contain a monoclonal antibody or fragment thereof that specifically binds to a protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a protein in a biological sample. Such kits generally comprise at least one oligonucleotide probe or primer, as described above, that hybridises to a polynucleotide encoding a protein. Such an oligonucleotide may be used, for example, within a PCR or hybridization assay. Additional components that may be present within such kits include a second oligonucleotide and/or a diagnostic reagent or container to facilitate the detection of a polynucleotide encoding a protein of the invention.

Other diagnostics kits include those designed for the detection of cell mediated responses (which may, for example, be of use in the diagnostic methods of the present invention). Such kits will typically comprise:
  (i) apparatus for obtaining an appropriate cell sample from a subject;
  (ii) means for stimulating said cell sample with an Rv2386c polypeptide (or variant thereof, immunogenic fragments thereof, or DNA encoding such polypeptides);
  (iii) means for detecting or quantifying the cellular response to stimulation.

Suitable means for quantifying the cellular response include a B-cell ELISPOT kit or alternatively a T-cell ELISPOT kit, which are known to those skilled in the art.

One possible kit comprises:
  (a) a polypeptide of the invention; and
  (b) a detection reagent suitable for direct or indirect detection of antibody binding.

Of particular interest are diagnostic kits tailored for quantifying T cell responses:

A diagnostic kit comprising:
  (a) a polypeptide of the invention; and
  (b) apparatus sufficient to contact said polypeptide with the dermal cells of an individual.

A diagnostic kit comprising:
  (a) a polypeptide of the invention;
  (b) apparatus sufficient to contact said polypeptide with a sample (e.g. whole blood or more suitably PBMC) from an individual; and
  (c) means to quantify the T cell response (e.g. proliferation or IFN-gamma production).

EXAMPLES

The following examples are provided by way of illustration only and not by way of limitation. Those of skill in the art will readily recognize a variety of noncritical parameters that could be changed or modified to yield essentially similar results.

Example 1

Identification of Rv2386c as a Latent TB Vaccine Target

The gene Rv2386c also known as Mbtl, encodes for a protein which is involved in the biogenesis of hydroxyphenyloxazoline-containing siderophore mycobactins where it converts chorismate to salicylate, the starter unit for mycobacterin siderophore synthesis.

Rv2386c was selected based on a genome-wide analysis of *Mycobacterium tuberculosis* genes associated with dormancy phase maintenance and infectivity as in Murphy and Brown BMC. Infect. Dis. 2007 7:84-99. Potential dormancy phase gene targets in Mycobacterium tuberculosis were prioritised through a bioinformatics meta-analysis of published genome-wide DNA microarray datasets of bacterial gene expression under simulated dormancy conditions. Subcellular localisation of M. tuberculosis proteins encoded by genes, was subsequently carried out on the entire genome to identify vaccine targets.

Briefly, experimental conditions in the dormancy models were quite varied so a zero to five scoring system was developed to normalise these data based upon two criteria: 1) the relevance of the experimental conditions to the dormant state and 2) the rank order of expression. The maximum score for a particular experimental dataset was adjusted based on potential relevance to the clinical occurrence of dormancy phase *M. tuberculosis* infections. Table 1 shows the data sets collected for Step 1 together with the adjusted maximum scores for each dataset. Additional datasets on gene essentiality for growth were obtained from published studies using transposon-based knockout experiments (TraSH). Genes which had no effect on growth received a score of zero.

TABLE 1

Sources, experimental models, and scoring criteria for *M. tuberculosis* DNA microarray gene expression and genome-wide gene knock-out (growth phase essentiality).

| Reference | Experimental model | Timepoint: Maximum score[a] |
|---|---|---|
| Betts J C et al.<br>*Mol. Microbiol.* 2002 43: 717-731 | Starvation under controlled $O_2$ | 96 h: 3<br>24 h: 2<br>4 h: 1 |
| Hampshire T et al.<br>*Tuberculosis.* (Edinb.) 2004 84: 228-238 | Nutrient depletion under controlled $O_2$ | 62 and 75 d: 5<br>49 d: 4<br>18 d: 2 |
| Muttucumaru D G et al.<br>*Tuberculosis.* (Edinb.) 2004 84: 239-246 | Wayne model of hypoxia[#] | 14 d (NRP-2): 4<br>7 d (NRP-1): 2 |
| Voskuil M I et al.<br>*Tuberculosis.* (Edinb.) 2004 84: 218-227 | Wayne model of hypoxia[#] | 30 and 80 d: 5<br>14 and 20 d: 4<br>10 and 12 d: 3<br>6 and 8 d: 2 |
| Schnappinger D et al.<br>*J. Exp. Med.* 2003 198: 693-704 | Infection of mouse macrophages, +/−γ-INF | 24 and 48 h: 5 |
| Karakousis P C et al.<br>*J. Exp. Med.* 2004 200: 647-657 | Hollow fiber subcutaneous implant in mice | 10 d: 3 |
| Talaat A M et al.<br>*Proc. Natl. Acad. Sci. U.S.A* 2004, 101: 4602-4607 | Infection of mice. MTB harvested from lung[b] | 28 d: 3 |
| Sassetti C M et al.<br>*Mol. Microbiol.* 2003 48: 77-84 | TraSH mutated libraries grown on solid media | 14 d: 5 |
| Rengarajan J et al.<br>*Proc. Natl. Acad. Sci. U.S.A* 2005, 102: 8327-8332 | Infection of mouse macrophages, +/−γ-INF with TraSH mutated libraries of *M. tuberculosis* | 7 d: 5 |
| Sassetti C M et al.<br>*Proc. Natl. Acad. Sci. U.S.A* 2003 100: 12989-12994 | C57BL/6J mice infected with TraSH mutated libraries of *M. tuberculosis* | 7, 14, 28 and 56 d: 5 |

[a]Maximum score based on relevance as a dormancy model; h = hour; d = day.
[b]Ratio of *M. tuberculosis* from Balb/c lung to MTB in aerated culture for 28 d.
[#]Wayne L G and Hayes L G *Infect. Immun.* 1996 64: 2062-2069

Step 2—In applying the second criterion, the rank order of gene expression, gene scores from each dataset were ordered from highest to lowest based on expression ratio (fold expression in the experimental condition versus cells in log-phase liquid culture). The highest scoring gene received the maximum score for that particular dataset (listed in column 3 of Table 1. (e.g. 5, 4 . . . , 1 point)). The score was decreased by 0.005 points for each gene in order until zero, or the end of the data set was reached. Thus when the maximum score was 4 points, the 100th ranked gene would receive a score of 3.500. For a maximum score of 5 points, 1000 genes or 25% of the *M. tuberculosis* genome received a score. For experiments where data from multiple time points were collected, the maximum score across all time points was used as the final score.

In Step 3 scores for each gene in each of the experimental conditions were collected into a Microsoft Access database. Reference fields were added to facilitate prioritisation, such as the Refseq ID, Genbank function, Genbank note, Tuberculist classification, and KEGG and Sanger Center links. By combining the data from different studies and sources, a consensus view was reached about the particular genes and pathways most critical for survival in the dormant state.

In Step 4, a prioritised list of therapeutic targets was derived utilising the top 400 scoring genes (~10% of the genome) supplemented by expert computational and manual analysis of biochemical pathways, enzymology, drug tractability, homology to human genes and other prior knowledge. The great majority of the high scoring genes come from the subset where two or three of the groups intersect.

In Step 5, the identification of subcellular localisation of *M. tuberculosis* proteins encoded by genes, was carried out on the entire genome. The heuristic used for membrane protein prediction is described in Chalker et al. *J. Bacteriol.* 2001 183:1259-1268. Average hydropathy profiles (H) (von Heijne G *J. Mol. Biol.* 1992 225:487-494) were generated using GES hydropathy values (Engelman D M et al. *Annu. Rev. Biophys. Biophys. Chem.* 1986 15:321-353) weighted using a trapezoid window. Using a process similar to the initial steps of the TopPred II algorithm (Claros M G et al. *Comput. Appl. Biosci.* 1994 10:685-686), helical transmembrane segments (TMS) were predicted for each peptide sequence by selecting 19 amino acids centered on the highest H value (MaxH), masking these from further consideration, and repeating the process until no peaks with a H of >0.5 remained. Subcellular locations were assigned based on the peak MaxH value, number of segments with a H of >1.0, and distribution and peak H values of the putative TMS. A MaxH cutoff of 1.15 was chosen to maximize the discrimination between two SwissProtein release 34 test datasets containing transmembrane and cytoplasmic proteins, respectively (Boyd D et al. *Protein Sci.* 1998 7:201-205). Proteins with a MaxH of <1.15 were classified as cytoplasmic, while those with a MaxH of >1.15 and at least three possible TMS were classified as membrane proteins. Anchored proteins were defined as having exactly two TMS, one starting before amino acid (aa) 35 and one having a H of >1.15 with the other having a H not lower than 0.5. SignalP with Gram positive settings was specifically used for *M. bacterium* to identify secreted proteins amongst those classified as either cytoplasmic or "unknown" in the heuristic analysis (Nielsen H et al. *Protein Eng.* 1997 10:1-6).

Rv2386c ranked very high as a vaccine antigen according to several criteria:

(i) Rv2386c is consistently up-regulated across all models of dormancy. Among the entire suite of 3999 genes scored in the meta-analysis, Rv2386c was ranked 120th as one of the top 10% of over-expressed genes across all dormancy models. The up-regulated score for Rv2386c was 13.165 which favourably compared with the top gene score of 22.28. Rv2386c was minimally down-regulated, scoring only slightly less than 0 (−2.316 compared to −18.13 for the most widely down regulated gene).

(ii) The scavenging of iron from macrophages is crucial for *M. tuberculosis* survival and infectivity. Small molecules called siderophores function in bacteria to bind iron for intra-cellular uptake, Mbtl catalyses the first step in the formation of the only *M. tuberculosis* siderophore, mycobactin T, the biosynthesis of which depends on the production of salicylate from chorismate (Harrison et al. *J. Bacteriol.* 2006 188:6081-6091). Expression of Mbtl is induced during *M. tuberculosis* infection of human THP-1 macrophages (Gold et al. *Mol. Microbiol.* 2001 42:851-865). The 3D protein structure is available and the mechanism of enzymatic action Mbtl has been well-studied (Zwahlen et al. *Biochemistry* 2007 46:954-964). Rv2386c ranked high in essentiality scoring and is required by *M. tuberculosis* for survival in in vitro growth models (scoring 2.6 out of a possible scoring of 5).

(iii) Subcellular localisation predicted that the Rv2386c protein is secreted and thus has significant extracellular exposure, indicating suitability as a vaccine target.

Example 2

Rv2386c Epitope Identification

Method

T cell epitope prediction was based on the following approaches:

| Prediction | Name | URL/References |
|---|---|---|
| CD4 and CD8 | Multipred | website: antigen.i2r.a-star.edu.sg/multipred/<br>Zhang, G. L., Khan, A. M., Srinivasan, K. N., August, J. T. and Brusic, V. (2005) "MULTIPRED: a computational system for prediction of promiscuous HLA binding peptides" Nucleic Acids Res. 33, W172-W179. |
| | SVMHC | website: www-bs.informatik.uni-tuebingen.de/SVMHC<br>"Prediction of MHC class I binding peptides, using SVMHC." Pierre Dönnes and Arne Elofsson in: BMC Bioinformatics 2002 3: 25 |
| CD4 | ProPred | website: www.imtech.res.in/raghava/propred/<br>Singh, H. and Raghava, G. P. S. (2001) "ProPred: Prediction of HLA-DR binding sites." *Bioinformatics*, 17(12), 1236-37. |
| | Tepitope2 | In house program based on:<br>H. Bian, J. Hammer (2004) "Discovery of promiscuous HLA-II-restricted T cell epitopes with TEPITOPE." Methods 34: 468-75 |
| CD8 | nHLA | website: www.imtech.res.in/raghava/nhlapred/<br>Bhasin M. and Raghava G P S (2006) "A hybrid approach for predicting promiscuous MHC class I restricted T cell epitopes"; J. Biosci. 32: 31-42 |
| | NetCTL | website: www.cbs.dtu.dk/services/NetCTL/<br>"An integrative approach to CTL epitope prediction. A combined algorithm integrating MHC-I binding, TAP transport efficiency, and proteasomal cleavage predictions." Larsen M. V., Lundegaard C., Kasper Lamberth, Buus S,. Brunak S., Lund O., and Nielsen M. European Journal of Immunology. 35(8): 2295-303. 2005 |
| | Epijen | website: www.jenner.ac.uk/EpiJen/<br>Doytchinova, I. A., P. Guan, D. R. Flower. "EpiJen: a server for multi-step T cell epitope prediction." *BMC Bioinformatics*, 2006, 7, 131. |
| | Syfpeithi | website: www.syfpeithi.de/Scripts/MHCServer.dll/EpitopePrediction.htm<br>Hans-Georg Rammensee, Jutta Bachmann, Niels Nikolaus Emmerich, Oskar Alexander Bachor, Stefan Stevanovic: "SYFPEITHI: database for MHC ligands and peptide motifs." Immunogenetics (1999) 50: 213-219 |
| | PredTAP | website: antigen.i2r.a-star.edu.sg/predTAP/<br>Zhang, G. L., Petrovsky, N., Kwoh, C. K., August, J. T. and Brusic, V. (2006) "M PRED$^{TAP}$: a system for prediction of peptide binding to the human transporter associated with antigen processing." Immunome Res. 2(1), 3. |

| Prediction | Name | URL/References |
|---|---|---|
| | PAPROC | website: www.paproc2.de/paproc1/paproc1.html<br>C. Kuttler, A. K. Nussbaum, T. P. Dick, H.-G. Rammensee, H. Schild, K. P. Hadeler, "An algorithm for the prediction of proteasomal cleavages", J. Mol. Biol. 298 (2000), 417-429<br>A. K. Nussbaum, C. Kuttler, K. P. Hadeler, H.-G. Rammensee, H. Schild, "PAProC: A Prediction Algorithm for Proteasomal Cleavages available on the WWW", Immunogenetics 53 (2001), 87-94 |

Results

TABLE 2

Putative Rv2386c human CD4+ T cell epitopes

| Putative CD4 epitope number | Amino acid position | Epitope sequence | SEQ ID No: | HLA allele |
|---|---|---|---|---|
| 1 | 54 | WVLAAGVQA | SEQ ID No: 30 | DRB1_0401 |
| 2 | 55 | VLAAGVQAM | SEQ ID No: 31 | DRB1_0301, DRB1_1301 |
| 3 | 73 | VIRDGVTRR | SEQ ID No: 32 | DRB1_0301, DRB1_0401 |
| 4 | 125 | LAPHTPLAR | SEQ ID No: 33 | DRB1_1301 |
| 5 | 148 | IRLFDAGIR | SEQ ID No: 34 | DRB1_1101, DRB1_1301, DRB1_1501 |
| 6 | 155 | IRHREAIDR | SEQ ID No: 35 | DRB1_0801, DRB1_1301 |
| 7 | 164 | LLATGVREV | SEQ ID No: 36 | DRB1_1301 |
| 8 | 187 | FRRRVAVAV | SEQ ID No: 37 | DRB1_0101, DRB1_0801 |
| 9 | 216 | FAIDFPLTY | SEQ ID No: 38 | DRB1_0301, DRB1_0401 |
| 10 | 220 | FPLTYRLGR | SEQ ID No: 39 | DRB1_1101 |
| 11 | 224 | YRLGRRHNT | SEQ ID No: 40 | DRB1_0801, DRB1_1101, DRB1_1501 |
| 12 | 234 | VRSFLLQLG | SEQ ID No: 41 | DRB1_1301 |
| 13 | 238 | LLQLGGIRA | SEQ ID No: 42 | DRB1_1501 |
| 14 | 253 | LVTAVRADG | SEQ ID No: 43 | DRB1_1301 |
| 15 | 257 | VRADGVVIT | SEQ ID No: 44 | DRB1_0301, DRB1_0401 |
| 16 | 262 | VVITEPLAG | SEQ ID No: 45 | DRB1_0301, DRB1_0401, DRB1_1301, DRB1_1501 |
| 17 | 295 | IVEHAISVR | SEQ ID No: 46 | DRB1_1301 |
| 18 | 321 | IDFMTVRER | SEQ ID No: 47 | DRB1_1301 |
| 19 | 375 | FRLDECPRG | SEQ ID No: 48 | DRB1_0301, DRB1_0401 |
| 20 | 384 | LYSGAVVML | SEQ ID No: 49 | DRB1_0301 |
| 21 | 385 | YSGAVVMLS | SEQ ID No: 50 | DRB1_0401, DRB1_1101 |
| 22 | 389 | VVMLSADGG | SEQ ID No: 51 | DRB1_0401, DRB1_1301 |
| 23 | 415 | WLRAGAGII | SEQ ID No: 52 | DRB1_0101 |

TABLE 3

Putative Rv2386c human CD8+ T cell epitopes

| Putative CD8 epitope number | Amino acid position | Epitope sequence | SEQ ID No: | HLA allele |
|---|---|---|---|---|
| 1 | 3 | ELSVATGAV | SEQ ID No: 53 | A_0201 |
| 2 | 5 | SVATGAVST | SEQ ID No: 54 | A_0201 |
| 3 | 18 | IPMPAGVNP | SEQ ID No: 55 | B_0702, B51, Cw_0401 |
| 4 | 19 | PMPAGVNPA | SEQ ID No: 56 | A_0201 |

TABLE 3-continued

Putative Rv2386c human CD8+ T cell epitopes

| Putative CD8 epitope number | Amino acid position | Epitope sequence | SEQ ID No: | HLA allele |
|---|---|---|---|---|
| 5 | 21 | PAGVNPADL | SEQ ID No: 57 | A_2402, B_3501 |
| 6 | 23 | GVNPADLAA | SEQ ID No: 58 | A3 |
| 7 | 25 | NPADLAAEL | SEQ ID No: 59 | A24, B_0702, B44, Cw_0401, Cw_0602, B7, B_3501, B51 |
| 8 | 28 | DLAAELAAV | SEQ ID No: 60 | A_0201 |
| 9 | 33 | LAAVVTESV | SEQ ID No: 61 | A2, A_0201, B51 |
| 10 | 37 | VTESVDEDY | SEQ ID No: 62 | A1, A_0101, A_0301 |
| 11 | 38 | TESVDEDYL | SEQ ID No: 63 | B44 |
| 12 | 40 | SVDEDYLLY | SEQ ID No: 64 | A1, A_0101, A3 |
| 13 | 48 | YECDGQWVL | SEQ ID No: 65 | A24, B_4403, B51, Cw_0401, B44 |
| 14 | 52 | GQWVLAAGV | SEQ ID No: 66 | A2, A_0201 |
| 15 | 55 | VLAAGVQAM | SEQ ID No: 67 | A2, B8 |
| 16 | 65 | ELDSDELRV | SEQ ID No: 68 | A_0201 |
| 17 | 67 | DSDELRVIR | SEQ ID No: 69 | A_0101, A_0301 |
| 18 | 82 | QQWSGRPGA | SEQ ID No: 70 | A_0201, A_0301 |
| 19 | 86 | GRPGAALGE | SEQ ID No: 71 | A3, B8 |
| 20 | 87 | RPGAALGEA | SEQ ID No: 72 | B7, B_0702, B_3501, B51 |
| 21 | 91 | ALGEAVDRL | SEQ ID No: 73 | A2, A_0201 |
| 22 | 93 | GEAVDRLLL | SEQ ID No: 74 | B44 |
| 23 | 106 | AFGWVAFEF | SEQ ID No: 75 | A24 |
| 24 | 124 | RLAPHTPLA | SEQ ID No: 76 | A2, A_0201, A3 |
| 25 | 125 | LAPHTPLAR | SEQ ID No: 77 | A_0101, A_0301 |
| 26 | 126 | APHTPLARV | SEQ ID No: 78 | B7, B_3501, B51 |
| 27 | 127 | PHTPLARVF | SEQ ID No: 79 | A24, B44 |
| 28 | 130 | PLARVFSPR | SEQ ID No: 80 | A_0101, A3, A_0301 |
| 29 | 133 | RVFSPRTRI | SEQ ID No: 81 | B7 |
| 30 | 134 | VFSPRTRIM | SEQ ID No: 82 | A24, B8 |
| 31 | 143 | VSEKEIRLF | SEQ ID No: 83 | A1, A24 |
| 32 | 153 | AGIRHREAI | SEQ ID No: 84 | B8, B51 |
| 33 | 164 | LLATGVREV | SEQ ID No: 85 | A2, A_0201 |
| 34 | 170 | REVPQSRSV | SEQ ID No: 86 | B44 |
| 35 | 172 | VPQSRSVDV | SEQ ID No: 87 | B7, B8 |
| 36 | 180 | VSDDPSGFR | SEQ ID No: 88 | A_0101, A_0301 |
| 37 | 183 | DPSGFRRRV | SEQ ID No: 89 | B_3501, B51 |
| 38 | 185 | SGFRRRVAV | SEQ ID No: 90 | B8, B51 |

TABLE 3-continued

Putative Rv2386c human CD8+ T cell epitopes

| Putative CD8 epitope number | Amino acid position | Epitope sequence | SEQ ID No: | HLA allele |
|---|---|---|---|---|
| 39 | 186 | GFRRRVAVA | SEQ ID No: 91 | A_0301, B8 |
| 40 | 187 | FRRRVAVAV | SEQ ID No: 92 | A3, B8, B51 |
| 41 | 190 | RVAVAVDEI | SEQ ID No: 93 | A24, B7 |
| 42 | 198 | IAAGRYHKV | SEQ ID No: 94 | B8, B51 |
| 43 | 200 | AGRYHKVIL | SEQ ID No: 95 | B7, B8 |
| 44 | 202 | RYHKVILSR | SEQ ID No: 96 | A3, A24 |
| 45 | 206 | VILSRCVEV | SEQ ID No: 97 | A2, A_0201 |
| 46 | 214 | VPFAIDFPL | SEQ ID No: 98 | B7, B_3501, B51 |
| 47 | 216 | FAIDFPLTY | SEQ ID No: 99 | A1, A_0101, B_3501, B51 |
| 48 | 218 | IDFPLTYRL | SEQ ID No: 100 | B44 |
| 49 | 226 | LGRRHNTPV | SEQ ID No: 101 | B8, B51 |
| 50 | 228 | RRHNTPVRS | SEQ ID No: 102 | A3, B8 |
| 51 | 231 | NTPVRSFLL | SEQ ID No: 103 | A_0101, A24 |
| 52 | 233 | PVRSFLLQL | SEQ ID No: 104 | A_0201, B7 |
| 53 | 245 | RALGYSPEL | SEQ ID No: 105 | A2, A_0201, B_3501, B51 |
| 54 | 246 | ALGYSPELV | SEQ ID No: 106 | A_0101, A2, A_0201 |
| 55 | 249 | YSPELVTAV | SEQ ID No: 107 | A2 |
| 56 | 250 | SPELVTAVR | SEQ ID No: 108 | B_0702, B_3501, B51 |
| 57 | 256 | AVRADGVVI | SEQ ID No: 109 | A3, A_0301, B7 |
| 58 | 264 | ITEPLAGTR | SEQ ID No: 110 | A_0101, A_0301 |
| 59 | 266 | EPLAGTRAL | SEQ ID No: 111 | B7, B8, B_3501, B51 |
| 60 | 270 | GTRALGRGP | SEQ ID No: 112 | A3, B8 |
| 61 | 272 | RALGRGPAI | SEQ ID No: 113 | A24, B7, B51 |
| 62 | 288 | LESNSKEIV | SEQ ID No: 114 | B44 |
| 63 | 294 | EIVEHAISV | SEQ ID No: 115 | A_0201 |
| 64 | 295 | IVEHAISVR | SEQ ID No: 116 | A_0101 |
| 65 | 298 | HAISVRSSL | SEQ ID No: 117 | B7, B8, B_3501 |
| 66 | 301 | SVRSSLEEI | SEQ ID No: 118 | B7 |
| 67 | 305 | SLEEITDIA | SEQ ID No: 119 | A2 |
| 68 | 311 | DIAEPGSAA | SEQ ID No: 120 | A_0101, A_0301 |
| 69 | 313 | AEPGSAAVI | SEQ ID No: 121 | B44 |
| 70 | 327 | RERGSVQHL | SEQ ID No: 122 | B7, B44 |
| 71 | 331 | SVQHLGSTI | SEQ ID No: 123 | A24, B7 |
| 72 | 342 | RLDPSSDRM | SEQ ID No: 124 | A2, A_0201 |
| 73 | 344 | DPSSDRMAA | SEQ ID No: 125 | B7, B_3501 |
| 74 | 346 | SSDRMAALE | SEQ ID No: 126 | A1, B8 |

TABLE 3-continued

Putative Rv2386c human CD8+ T cell epitopes

| Putative CD8 epitope number | Amino acid position | Epitope sequence | SEQ ID No: | HLA allele |
|---|---|---|---|---|
| 75 | 348 | DRMAALEAL | SEQ ID No: 127 | B7, Cw_0401, Cw_0602 |
| 76 | 349 | RMAALEALF | SEQ ID No: 128 | A24 |
| 77 | 351 | AALEALFPA | SEQ ID No: 129 | A2, A_0201, B_3501 |
| 78 | 352 | ALEALFPAV | SEQ ID No: 130 | A_0101, A2, A_0201 |
| 79 | 353 | LEALFPAVT | SEQ ID No: 131 | B8, B_4403 |
| 80 | 357 | FPAVTASGI | SEQ ID No: 132 | B7, B8, B_3501, B51 |
| 81 | 359 | AVTASGIPK | SEQ ID No: 133 | A3, A_0301, B7 |
| 82 | 360 | VTASGIPKA | SEQ ID No: 134 | A_0201 |
| 83 | 364 | GIPKAAGVE | SEQ ID No: 135 | A_0301, B8 |
| 84 | 365 | IPKAAGVEA | SEQ ID No: 136 | B7, B_3501 |
| 85 | 367 | KAAGVEAIF | SEQ ID No: 137 | A24, B_3501 |
| 87 | 369 | AGVEAIFRL | SEQ ID No: 138 | A_0201, B51 |
| 87 | 376 | RLDECPRGL | SEQ ID No: 139 | A2, A_0201 |
| 88 | 380 | CPRGLYSGA | SEQ ID No: 140 | B7, B_3501 |
| 89 | 383 | GLYSGAVVM | SEQ ID No: 141 | A2, A_0201, A_0301, A3 |
| 90 | 384 | LYSGAVVML | SEQ ID No: 142 | A24, B44 |
| 91 | 390 | VMLSADGGL | SEQ ID No: 143 | A2, A_0201, A24 |
| 92 | 397 | GLDAALTLR | SEQ ID No: 144 | A_0101, A3, A_0301 |
| 93 | 398 | LDAALTLRA | SEQ ID No: 145 | A_0201, B_4403 |
| 94 | 400 | AALTLRAAY | SEQ ID No: 146 | A_0101, A_0301, B_3501 |
| 95 | 402 | LTLRAAYQV | SEQ ID No: 147 | A_0201 |
| 96 | 407 | AYQVGGRTW | SEQ ID No: 148 | A24 |
| 97 | 414 | TWLRAGAGI | SEQ ID No: 149 | A24 |
| 98 | 424 | EESEPEREF | SEQ ID No: 150 | B44 |
| 99 | 430 | REFEETCEK | SEQ ID No: 151 | B44 |
| 100 | 438 | KLSTLTPYL | SEQ ID No: 152 | A2, A_0201 |
| 101 | 440 | STLTPYLVA | SEQ ID No: 153 | A_0101, A_0201 |
| 102 | 441 | TLTPYLVAR | SEQ ID No: 154 | A3, A_0301 |

As can be seen from Tables 2 and 3, Rv2386c contains a number of predicted CD4+ and CD8 T cell epitopes. Furthermore, this information suggests that the protein carries epitopes that can be recognised by HLAs which occur worldwide (that is HLAs from Caucasian, African, Asian or Latin-American individuals available on the worldwide web at allelefrequencies.net).

Example 3

H37Rv Homologues

Rv2386c sequences from a number of *M. tuberculosis* strains and BCG were identified using BLASTP searches of GenBank (H37Rv reference sequence accession number YP_177877.1

| Strain | Accession Number | % identity |
| --- | --- | --- |
| CDC1551 | NP_336935.1 | 100 |
| F11 | YP_001288342.1 | 100 |
| Haarlem | ZP_02247771.1 | 100 |
| C | ZP_00878160.1 | 99 |
| BCG | CAL72388.1 | 100 |

Alignment of the homologue sequences indicates a high level of identity.

Biological Assays

Quantification of T Cell Responses to Rv2386c

Polypeptides may be screened for their ability to activate T-cells (induction of proliferation and/or production of cytokines) in peripheral blood mononuclear cell (PBMC) or in whole blood preparations from infected (such as latently infected) individuals.

Latently infected individuals are usually identified by a skin test that has a diameter above 10 mm and without symptoms, with no Mtb (M. tuberculosis) positive culture, with a negative sputum negative and with no lesion (as detected by chest X-Ray).

A range of in vitro assays can be used based on PBMC samples or whole blood: after restimulation in presence of the antigen (or variant/immunogenic fragment thereof as appropriate) the proliferation of the cells may be determined (as measured by CFSE/flow cytometry) or the production of cytokines quantified (present in the supernatant of cultured cells and measured by ELISA, or, after intracellular staining of CD4 and CD8 T cells and analysis by flow cytometry).

For example, PBMC samples may be obtained from heparinised whole blood by Ficoll-Hypaque density gradient centrifugation following standard procedures. The cells may then be washed and cryopreserved in liquid nitrogen until testing (for further details see Lalvani A et al. *J. Infect. Dis.* 1999 180:1656-1664).

T Cell Proliferation

The specific immune response may be characterised by performing lymphocyte proliferation analysis using the tritiated thymidine. This technique assesses the cellular expansion upon in vitro stimulation to an antigen. In practice, cell proliferation is determined by estimating incorporation of tritiated-thymidine into DNA, a process closely related to underlying changes in cell number.

More suitably, lymphocyte proliferation may be performed using the succinimidyl ester of carboxyfluorsecein diacetate (CFSE). CFSE spontaneously and irreversibly couples to both intracellular and cell surface proteins by reaction with lysine side chains and other available amine groups. When lymphocyte cells divide, CFSE labelling is distributed equally between the daughter cells, which are therefore half as fluorescent as the parents. As a result, halving of cellular fluorescence intensity marks each successive generation in a population of proliferating cells and is readily followed by flow cytometry (for further details see Hodgkins, P D et al *J. Exp. Med.* 1996 184:277-281).

Practically, after thawing, PMBC may be washed and stained with CFSE before being cultivated ($2\times10^5$ cells) for 72 hrs with 10 ug/ml of antigen in culture media (RPMI-1640 supplemented with glutamine, non essential amino acid, pyruvate and heat inactivated human AB serum). Cells may then be harvested and their phenotype characterised using surface staining to identify memory CD8 and CD4+ T-Cells. Subsequently, flow cytometry analysis can be used to indicate the extent of lymphocyte proliferation in response to each antigen (proportion of cells with decreased CFSE intensity upon in vitro stimulation).

Cytokine Production

IFN-γ production (or the production of other cytokines such as e.g. IL2, TNF-alpha, IL5, IL12 etc) may be measured using an enzyme-linked immunosorbent assay (ELISA). ELISA plates may be coated with a mouse monoclonal antibody directed to human IFN-γ (PharMingen, San Diego, Calif.) in PBS for four hours at room temperature. Wells are then blocked with PBS containing 5% (W/V) non-fat dried milk for 1 hour at room temperature. The plates are then washed, for example, six times in PBS/0.2% TWEEN™-20 and samples diluted 1:2 in culture medium in the ELISA plates are incubated overnight at room temperature. The plates are again washed and a polyclonal rabbit anti-human IFN-γ serum, for example, diluted 1:3000 in PBS/10% normal goat serum may be added to each well. The plates are then incubated for two hours at room temperature, washed and horseradish peroxidase-coupled anti-rabbit IgG (Sigma Chemical So., St. Louis, Mo.) may be added, for example, at a 1:2000 dilution in PBS/5% non-fat dried milk. After a further two hour incubation at room temperature, the plates are washed and TMB substrate added. The reaction may be stopped after 20 min with 1 N sulfuric acid. Optical density can then be determined at 450 nm using 570 nm as a reference wavelength. Typically, fractions that result in both replicates giving an OD two fold greater than the mean OD from cells cultured in medium alone may be considered positive.

Example 4

Immunogenicity in CB6F1 Mice

The immunogenicity of the antigen was evaluated in CB6F1 mice (first generation cross of BALB/c and C57BL/6 mice).

CB6F1 mice were immunised intramuscularly three times (on day 0, day 14 and day 28) with 0.5 ug or 2 ug of protein antigen in combination with the Adjuvant System AS01E (a liposomal adjuvant formulation comprising 3D-MPL and QS21).

The experimental design was as follows:

| Group | Day 0 | Day 14 | Day 28 |
| --- | --- | --- | --- |
| 1 | 2 ug Rv2386c/AS01E | 2 ug Rv2386c/AS01E | 2 ug Rv2386c/AS01E |
| 2 | 0.5 ug Rv2386c/AS01E | 0.5 ug Rv2386c/AS01E | 0.5 ug Rv2386c/AS01E |

A total of 24 mice were used in each protocol group.

Peripheral blood lymphocytes (PBL) were collected and pooled on day 21 (i.e. 7 days post second immunisation) and day 35 (i.e. 7 days post third immunisation) and the antigen-specific CD4 & CD8 T cell responses (as determined by CD4 or CD8 T cells producing IL-2 and/or IFN-gamma and/or TNF-alpha) were measured by flow cytometry after overnight in vitro restimulation with pools of 15mer peptides covering the sequences of interest. The detection of mouse T cells that express IL-2 and/or IFN-gamma and/or TNF-alpha was done by using short-term antigen-driven in vitro amplification of cytokine expression.

Briefly, PharmLyse solution (BD-Pharmingen) was added to heparinised mouse peripheral blood in order to lyse the red blood cells. The PBLs (Peripheral Blood Lymphocytes)

obtained were washed and then incubated in the presence of a pool of 15-mer peptides—overlapping by 11 amino acids—covering the sequence of the antigen of interest and of 1 ug/ml of antibodies to CD28 and CD49d (BD-Pharmingen). Each 15-mer peptide was used at a final concentration of 1 ug/ml. Medium controls were also stimulated with antibodies to CD28 and CD49d.

The cytokine secretion blocking compound brefeldin-A (BD-Pharmingen) was added 2 h after the onset of the cultures at 37° C., 5% $CO_2$ and the cells maintained at 37° C., 5% $CO_2$ for 4 additional hours followed by overnight incubation at +4° C.

Cells were then harvested and stained with Pacific Blue-coupled anti-CD4 (BD—clone RM4-5, BD-Pharmingen) and peridinin chlorophyll A protein (PerCp) cyanin5.5 (Cy5.5)-coupled anti-CD8 alpha (clone 53-6.7, BD-Pharmingen) antibodies.

Cells were then washed, fixed, permeabilised (Cytofix-cytoperm kit, BD-Pharmingen) and stained with allophyco-cyanin-coupled anti-IFN-g antibodies (clone XMG1.2, BDPharmingen), fluorescein isothiocyanate (FITC)-coupled anti-IL-2 antibodies (clone JES 6-5H4, Beckman Coulter) and phycoerythrin (PE)-coupled anti-TNF alpha antibodies (clone MP6-XT22, BDPharmingen). After final washes, stained cells were analysed on a LSR II flow cytometer (Beckton-Dickinson). A minimum number of 10,000 cells were acquired in the CD8+ subset.

For further background see Walzer T et al *Cell Immunol.* 2000 206(1):16-25 and Maecker H T et al *J. Immunol. Methods* 2001 255(1-2):27-40.

As negative controls, some cells were also cultured overnight in vitro in culture medium (unstimulated). The antigen-specific responses were calculated by subtracting the average cytokine response produced by unstimulated cells from the average cytokine response produced by the peptide-stimulated cells.

At each timepoint and for each group, the data was collected from 4 pools of 6 mice each. The data below is presented as the % of CD4 or CD8 T cells producing IL-2 and/or IFN-gamma and/or TNF-alpha. Each individual pool of mice is plotted (triangles) as well as the average value of the group (bar).

FIG. 1 shows that on day 21 (i.e. 7 days post second immunisation), Rv2386c-specific CD4 and CD8 T cell responses are detected in mice immunised with either dose of Rv2386c/AS01E. The levels of Rv2386c-specific CD4 T cell responses are similar regardless of the immunising dose of Rv2386. In contrast, mice immunised with 2 ug Rv2386c/AS01E displayed higher Rv2386c-specific CD8 T cell responses than mice immunised with 0.5 ug Rv2386c/AS01E.

FIG. 2 shows the cytokine profile of CD4 T cell response from the Rv2386c peptide pool-stimulated PBL (not medium removed) on day 21 (i.e. 7 days post second immunisation).

Figure 3:
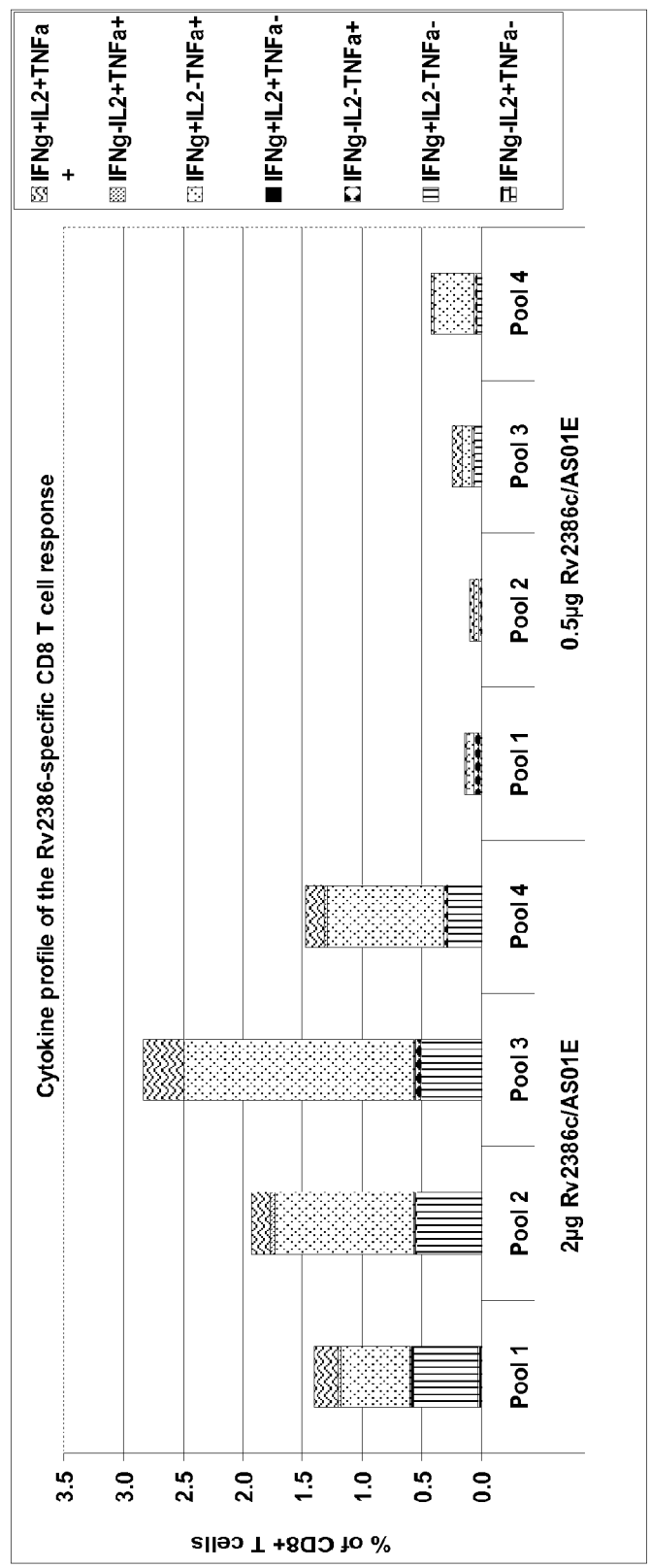
FIG. 3: Cytokine profile at day 21 (i.e. 7 days post second immunisation) of the antigen specific CD8 response in immunised CB6F1 mice.

FIG. 3 shows the cytokine profile of CD8 T cell response from the Rv2386c peptide pool-stimulated PBL (not medium removed) on day 21 (i.e. 7 days post second immunisation).

Figure 4:
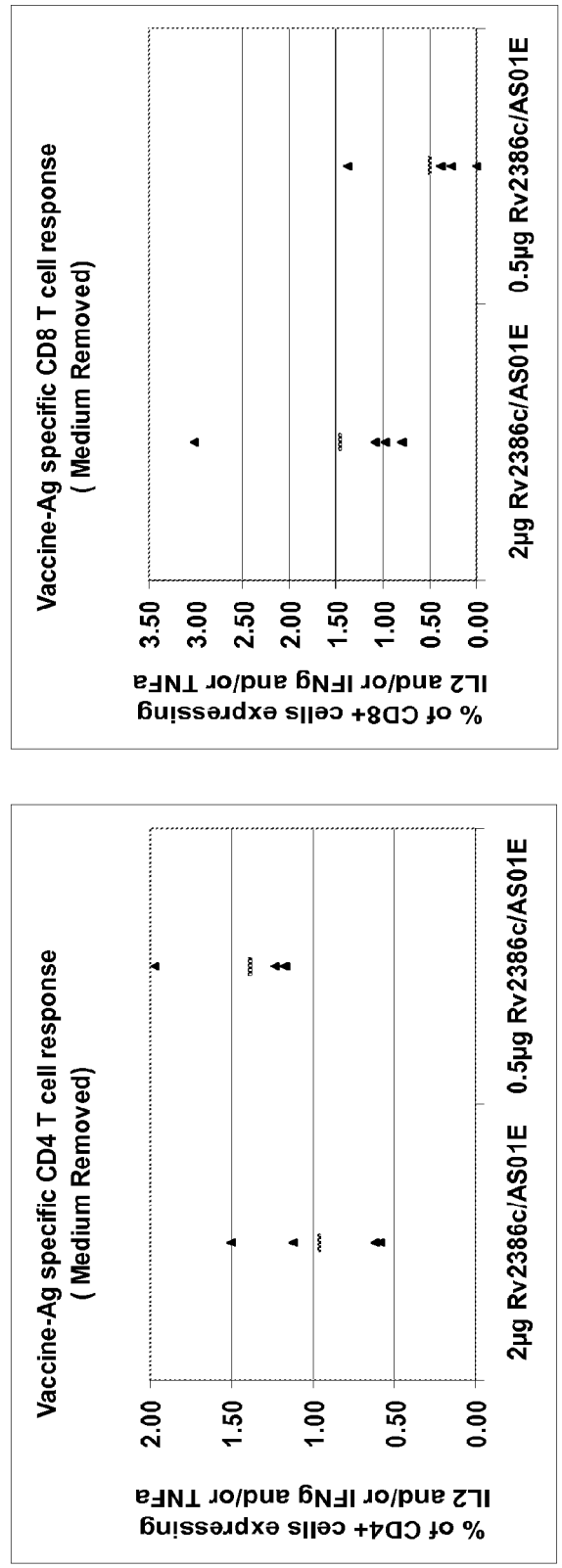
FIG. 4: Percentage of CD4 and CD8 cells from immunised CB6F1 mice expressing IFN-gamma and/or IL-2 and/or TNF-alpha cytokines at day 35 (i.e. 7 days post third immunisation).

FIG. 4 shows that on day 35 (i.e. 7 days post third immunisation), Rv2386c-specific CD4 and CD8 T cell responses are detected in mice immunised with either dose of Rv2386c/AS01E. The levels of Rv2386c-specific CD4 T cell responses are similar regardless of the immunising dose of Rv2386. In contrast, mice immunised with 2 ug Rv2386c/ AS01E displayed higher Rv2386c-specific CD8 T cell responses than mice immunised with 0.5 ug Rv2386c/AS01E.

The third immunisation dose increases the CD4 T cell response but not the CD8 T cell response.

Figure 5:
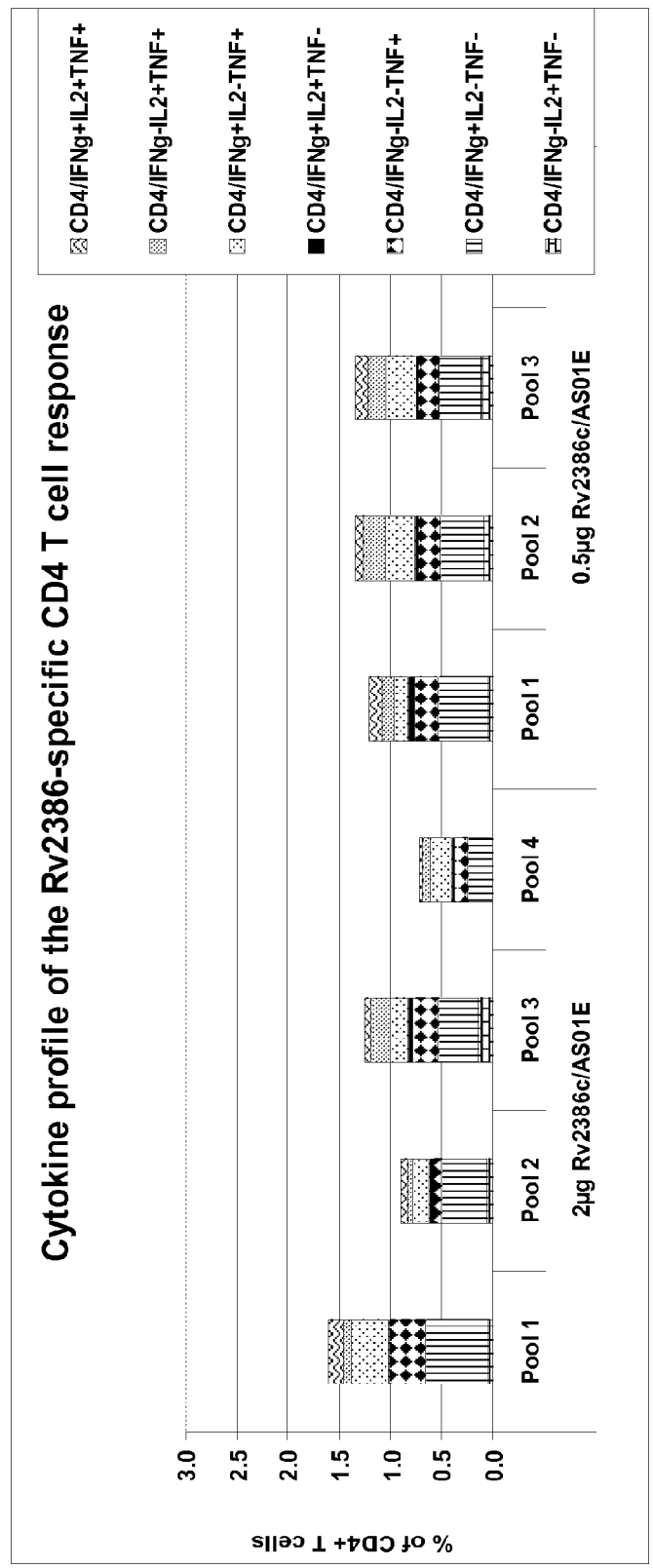
FIG. 5: Cytokine profile at day 35 (i.e. 7 days post third immunisation) of the antigen specific CD4 response in immunised CB6F1 mice.

FIG. 5 shows the cytokine profile of CD4 T cell response from the Rv2386c peptide pool-stimulated PBL (not medium removed) on day 35 (i.e. 7 days post third immunisation).

Figure 6:
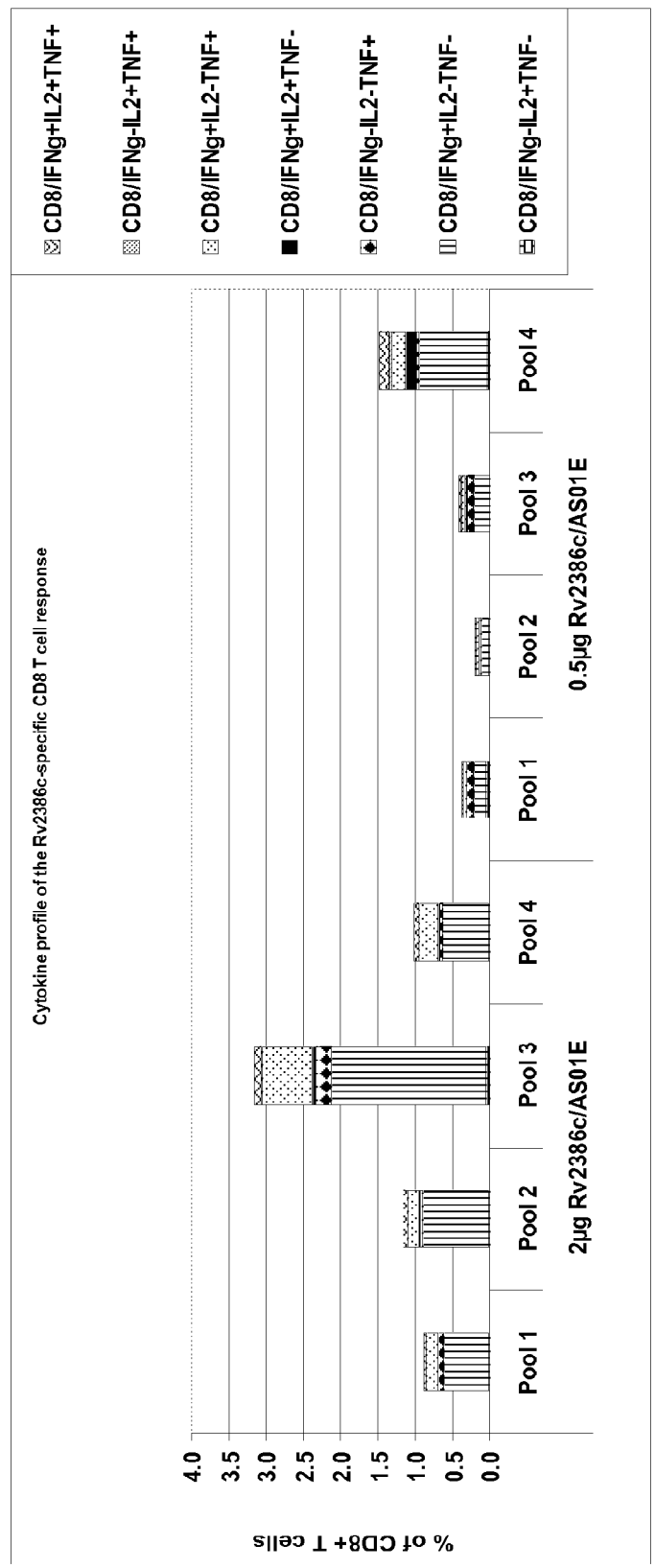
FIG. 6: Cytokine profile at day 35 (i.e. 7 days post third immunisation) of the antigen specific CD8 response in immunised CB6F1 mice.

FIG. 6 shows the cytokine profile of CD8 T cell response from the Rv2386c peptide pool-stimulated PBL (not medium removed) on day 35 (i.e. 7 days post third immunisation).

Example 5

Immunogenicity in C57BL/6 Mice

The immunogenicity of the antigen was also evaluated in C57BL/6 mice. C57BL/6 mice were immunised intramuscularly three times (on day 0, day 14 and day 28) with 1 ug or 4 ug of protein antigen in combination with a the Adjuvant System AS01E (a liposomal adjuvant formulation comprising 3D-MPL and QS21).

The experimental design was the following:

| Group | Day 0 | Day 14 | Day 28 |
|---|---|---|---|
| 1 | 4 ug Rv2386c/ AS01E | 4 ug Rv2386c/AS01E | 4 ug Rv2386c/AS01E |
| 2 | 1 ug Rv2386c/ AS01E | 1 ug Rv2386c/AS01E | 1 ug Rv2386c/AS01E |

Peripheral blood lymphocytes (PBL) were collected and pooled on day 21 (i.e. 7 days post second immunisation) and day 35 (i.e. 7 days post third immunisation) and the antigen-specific CD4 & CD8 T cell responses (as determined by CD4 or CD8 T cells producing IL-2 and/or IFN-gamma and/or TNF-alpha) were measured by flow cytometry after overnight in vitro restimulation with pools of 15mer peptides covering the sequences of interest. The procedure followed was as described previously.

As negative controls, some cells were also cultured overnight in vitro in culture medium (unstimulated). The antigen-specific responses were calculated by subtracting the average cytokine response produced by unstimulated cells from the average cytokine response produced by the peptide-stimulated cells.

At each timepoint and for each group, the data was collected from 4 pools of 6 mice each. The data below is presented as the % of CD4 or CD8 T cells producing IL-2 and/or IFN-gamma and/or TNF-alpha. Each individual pool of mice is plotted (triangles) as well as the average value of the group (bar).

Figure 7:
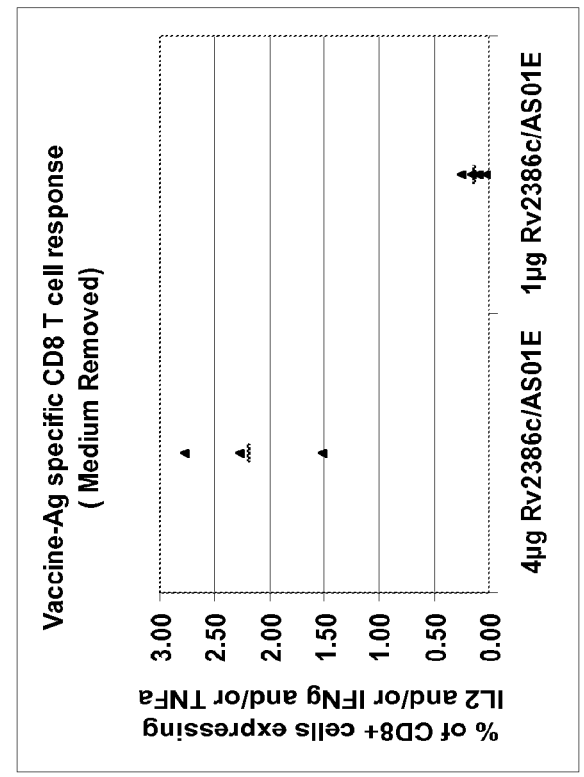
FIG. 7: Percentage of CD4 and CD8 cells from immunised C57BL/6 mice expressing IFN-gamma and/or IL-2 and/or TNF-alpha cytokines at day 21 (i.e. 7 days post second immunisation).
Figure 7:
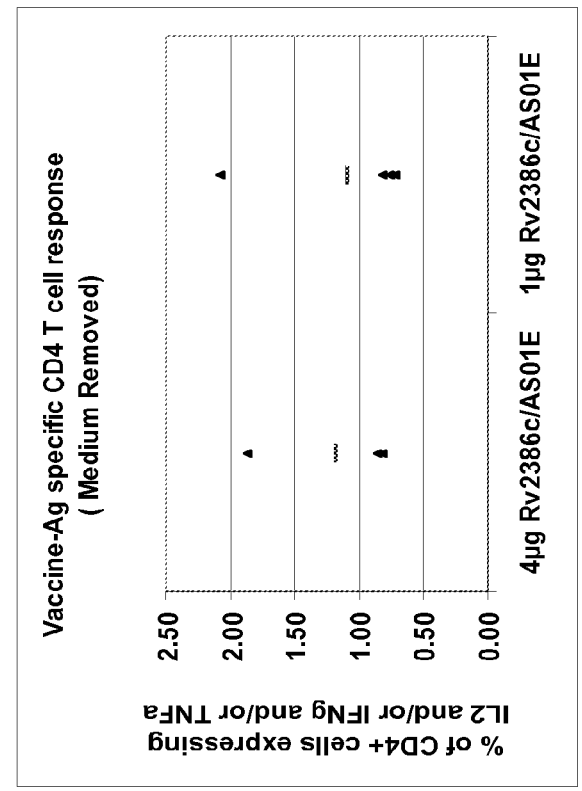

FIG. 7 shows that on day 21 (i.e. 7 days post second immunisation), Rv2386c-specific CD4 and CD8 T cell responses are detected in mice immunised with either dose of Rv2386c/AS01E. The levels of Rv2386c-specific CD4 T cell responses are similar regardless of the immunising dose of Rv2386c. In contrast, mice immunised with 4 ug Rv2386c/AS01E displayed higher Rv2386c-specific CD8 T cell responses than mice immunized with 1 ug Rv2386c/AS01E. Due to technical difficulties, data for the first pool of cells at the 4 ug dose are not available.

Figure 8:
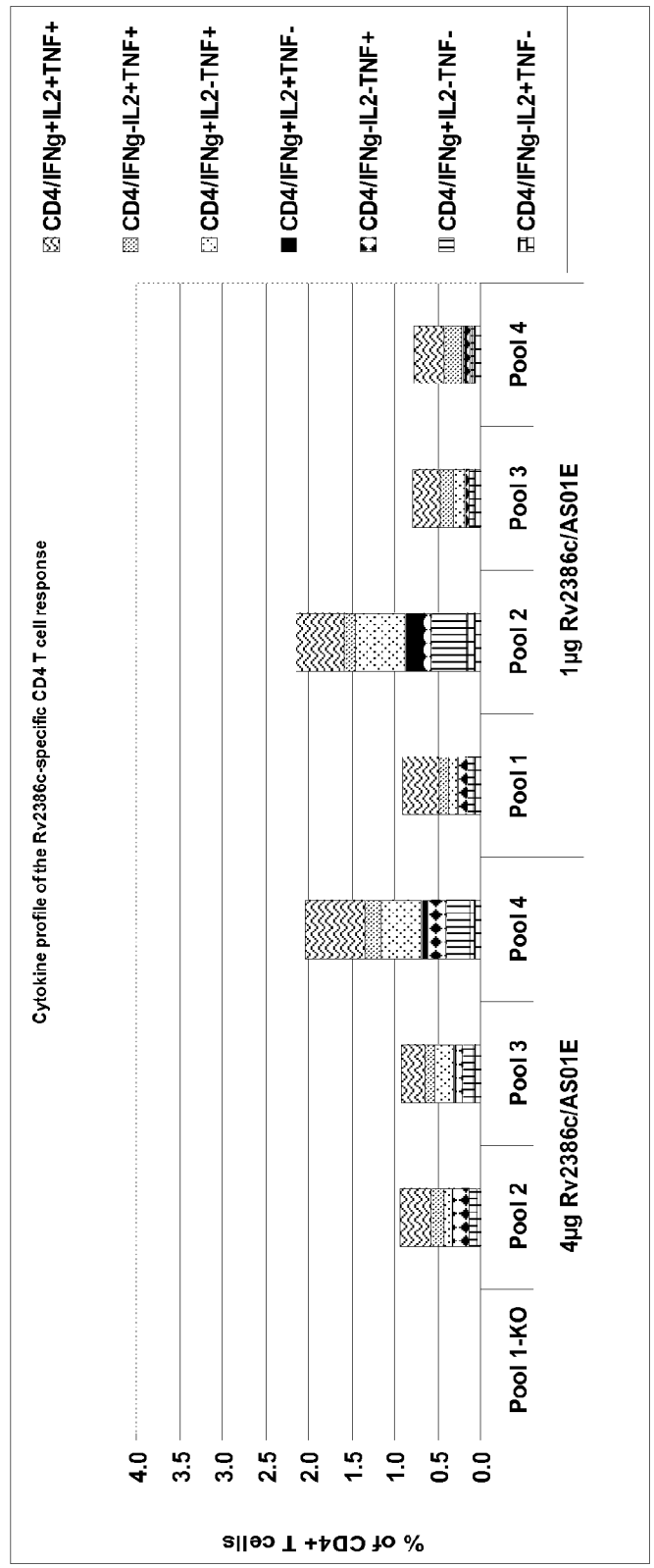
FIG. 8: Cytokine profile at day 21 (i.e. 7 days post second immunisation) of the antigen specific CD4 response in immunised C57BL/6 mice.

FIG. 8 shows the cytokine profile of CD4 T cell response from the Rv2386c peptide pool-stimulated PBL (not medium removed) on day 21 (i.e. 7 days post second immunisation). Due to technical difficulties, data for the first pool of cells at the 4 ug dose are not available.

Figure 9:
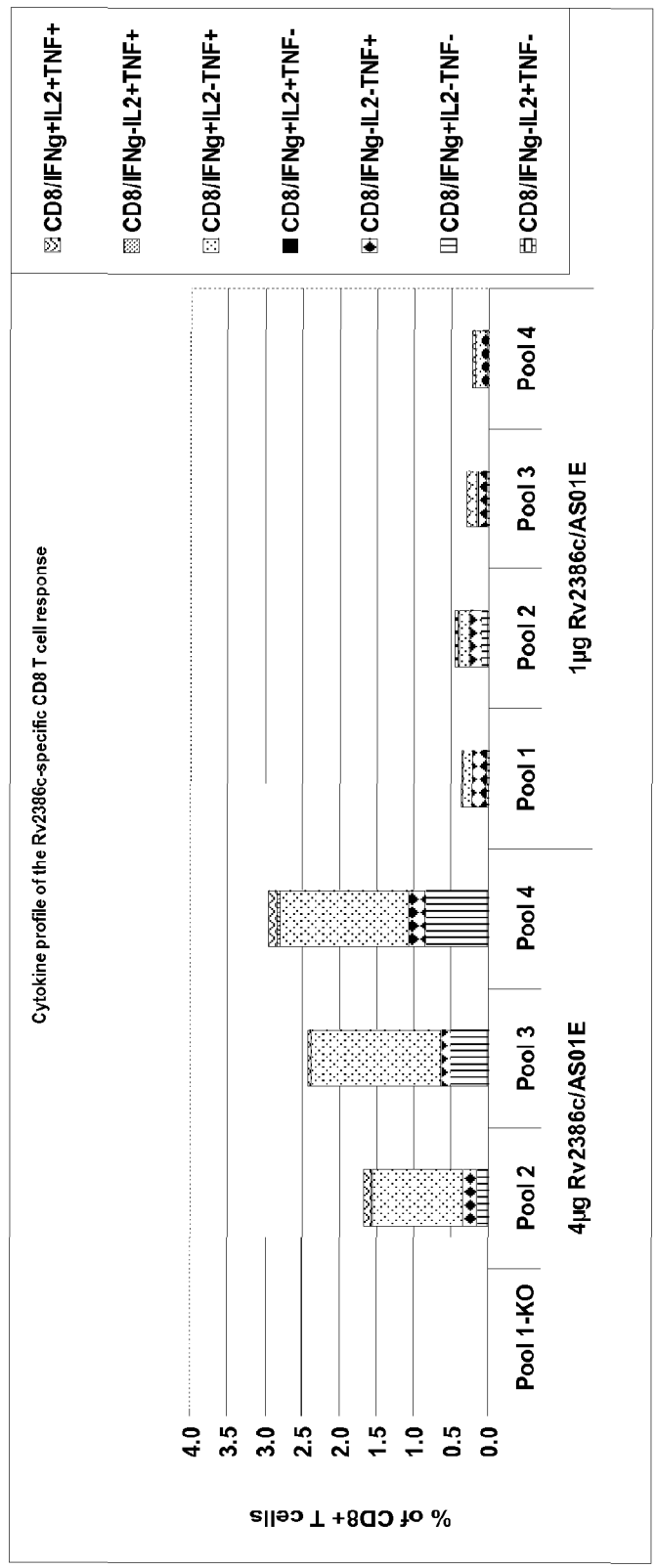
FIG. 9: Cytokine profile at day 21 (i.e. 7 days post second immunisation) of the antigen specific CD8 response in immunised C57BL/6 mice.

FIG. 9 shows the cytokine profile of CD8 T cell response from the Rv2386c peptide pool-stimulated PBL (not medium removed) on day 21 (i.e. 7 days post second immunisation). Due to technical difficulties, data for the first pool of cells at the 4 ug dose are not available.

Immunological data for day 35 were not yet available at the time this application was prepared.

In conclusion it may be noted that the Rv2386c antigen is capable of eliciting an immune response in both CB6F1 and C57BL/6 mice. Furthermore, the profile of cytokine production indicates that a large proportion of antigen-specific T-cells express a plurality of Th1 associated cytokines (i.e. a polyfunctional T-cell response is elicited). Importantly both CD4 and CD8 antigen-specific T-cells are present after immunisation, CD8 cells may be particularly important in a latent TB scenario. Rv2386c may therefore be expected to be of substantial value in the prevention, treatment and diagnosis of latent *tuberculosis* infection.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All references referred to in this application, including patents and patent applications, are incorporated herein by reference to the fullest extent possible as if each individual publication or patent application were specifically and individually indicated to be incorporated by reference.

THROUGHOUT THE SPECIFICATION AND THE CLAIMS WHICH FOLLOW, UNLESS THE CONTEXT REQUIRES OTHERWISE, THE WORD ‘COMPRISE’, AND VARIATIONS SUCH AS ‘COMPRISES’ AND ‘COMPRISING’, WILL BE UNDERSTOOD TO IMPLY THE INCLUSION OF A STATED INTEGER, STEP, GROUP OF INTEGERS OR GROUP OF STEPS BUT NOT TO THE EXCLUSION OF ANY OTHER INTEGER, STEP, GROUP OF INTEGERS OR GROUP OF STEPS.

We claim:

1. A sterile pharmaceutical composition comprising a polypeptide which comprises:
   (i) an Rv2386c protein comprising an amino acid sequence selected from the group consisting of SEQ ID NOS: 1 and 6; or
   (ii) an Rv2386c protein comprising an amino acid sequence at least 90% identical to an amino acid sequence selected from the group consisting of SEQ ID NOS: 1 and 6; and a pharmaceutically acceptable carrier or excipient.

2. An immunogenic composition comprising a polypeptide which comprises:

(i) an Rv2386c protein comprising an amino acid sequence selected from the group consisting of SEQ ID NOS: 1 and 6; or (ii) an Rv2386c protein comprising an amino acid sequence at least 90% identical to an amino acid sequence selected from the group consisting of SEQ ID NOS: 1 and 6; and a non-specific immune response enhancer.

3. The composition according to claim 1, wherein the polypeptide comprises an amino acid sequence at least 90% identical to SEQ ID NO: 1.

4. The immunogenic composition according to claim 2, wherein the polypeptide comprises an amino acid sequence at least 90% identical to SEQ ID NO:1.

5. The composition according to claim 1, wherein the polypeptide comprises an amino acid sequence at least 90% identical to SEQ ID NO: 6.

6. The immunogenic composition according to claim 2, wherein the polypeptide comprises an amino acid sequence at least 90% identical to SEQ ID NO:6.

* * * * *

SEQUENCE LISTING

```
<160> NUMBER OF SEQ ID NOS: 156

<210> SEQ ID NO 1
<211> LENGTH: 450
<212> TYPE: PRT
<213> ORGANISM: Mycobacterium tuberculosis
<220> FEATURE:
<221> NAME/KEY: MISC_FEATURE
<223> OTHER INFORMATION: Strain H37Rv

<400> SEQUENCE: 1

Met Ser Glu Leu Ser Val Ala Thr Gly Ala Val Ser Thr Ala Ser Ser
1               5                   10                  15

Ser Ile Pro Met Pro Ala Gly Val Asn Pro Ala Asp Leu Ala Ala Glu
            20                  25                  30

Leu Ala Ala Val Val Thr Glu Ser Val Asp Glu Asp Tyr Leu Leu Tyr
        35                  40                  45

Glu Cys Asp Gly Gln Trp Val Leu Ala Ala Gly Val Gln Ala Met Val
    50                  55                  60

Glu Leu Asp Ser Asp Glu Leu Arg Val Ile Arg Asp Gly Val Thr Arg
65                  70                  75                  80

Arg Gln Gln Trp Ser Gly Arg Pro Gly Ala Ala Leu Gly Glu Ala Val
                85                  90                  95

Asp Arg Leu Leu Leu Glu Thr Asp Gln Ala Phe Gly Trp Val Ala Phe
            100                 105                 110

Glu Phe Gly Val His Arg Tyr Gly Leu Gln Gln Arg Leu Ala Pro His
        115                 120                 125

Thr Pro Leu Ala Arg Val Phe Ser Pro Arg Thr Arg Ile Met Val Ser
    130                 135                 140

Glu Lys Glu Ile Arg Leu Phe Asp Ala Gly Ile Arg His Arg Glu Ala
145                 150                 155                 160

Ile Asp Arg Leu Leu Ala Thr Gly Val Arg Glu Val Pro Gln Ser Arg
                165                 170                 175

Ser Val Asp Val Ser Asp Asp Pro Ser Gly Phe Arg Arg Arg Val Ala
            180                 185                 190

Val Ala Val Asp Glu Ile Ala Ala Gly Arg Tyr His Lys Val Ile Leu
        195                 200                 205
```

```
Ser Arg Cys Val Glu Val Pro Phe Ala Ile Asp Phe Pro Leu Thr Tyr
    210                 215                 220
Arg Leu Gly Arg Arg His Asn Thr Pro Val Arg Ser Phe Leu Leu Gln
225                 230                 235                 240
Leu Gly Gly Ile Arg Ala Leu Gly Tyr Ser Pro Glu Leu Val Thr Ala
                245                 250                 255
Val Arg Ala Asp Gly Val Val Ile Thr Glu Pro Leu Ala Gly Thr Arg
                260                 265                 270
Ala Leu Gly Arg Gly Pro Ala Ile Asp Arg Leu Ala Arg Asp Asp Leu
                275                 280                 285
Glu Ser Asn Ser Lys Glu Ile Val Glu His Ala Ile Ser Val Arg Ser
    290                 295                 300
Ser Leu Glu Glu Ile Thr Asp Ile Ala Glu Pro Gly Ser Ala Ala Val
305                 310                 315                 320
Ile Asp Phe Met Thr Val Arg Glu Arg Gly Ser Val Gln His Leu Gly
                325                 330                 335
Ser Thr Ile Arg Ala Arg Leu Asp Pro Ser Ser Asp Arg Met Ala Ala
                340                 345                 350
Leu Glu Ala Leu Phe Pro Ala Val Thr Ala Ser Gly Ile Pro Lys Ala
                355                 360                 365
Ala Gly Val Glu Ala Ile Phe Arg Leu Asp Glu Cys Pro Arg Gly Leu
                370                 375                 380
Tyr Ser Gly Ala Val Val Met Leu Ser Ala Asp Gly Gly Leu Asp Ala
385                 390                 395                 400
Ala Leu Thr Leu Arg Ala Ala Tyr Gln Val Gly Gly Arg Thr Trp Leu
                405                 410                 415
Arg Ala Gly Ala Gly Ile Ile Glu Glu Ser Glu Pro Glu Arg Glu Phe
                420                 425                 430
Glu Glu Thr Cys Glu Lys Leu Ser Thr Leu Thr Pro Tyr Leu Val Ala
                435                 440                 445
Arg Gln
    450

<210> SEQ ID NO 2
<211> LENGTH: 1353
<212> TYPE: DNA
<213> ORGANISM: Mycobacterium tuberculosis
<220> FEATURE:
<221> NAME/KEY: misc_feature
<223> OTHER INFORMATION: Strain H37Rv

<400> SEQUENCE: 2
atgtccgagc tcagcgtcgc gacaggcgcc gtcagcaccg cgtcgtcgtc catcccgatg      60
cccgccggtg tcaaccccgc cgacctggca gcggagctgg cggcggtggt taccgagtcc     120
gtcgacgagg attacctgct ctacgagtgc gacggccaat gggtcctggc cgccggtgtg     180
caggcgatgt ggagctaga cagcgacgaa ctgcgcgtca tccgtgatgg cgttacgcgg     240
cgacagcaat ggtcgggtcg cccgggagcg gccctgggcg aagccgtcga tcggctgttg     300
ctggaaaccg atcaagcttt tggctgggtc gccttcgaat cggcgtgca ccgctatggg      360 ttgcagcagc ggctggcgcc gcacacccca ctggcccggg tgttttcgcc ccgaaccccgg    420 atcatggtga gcgaaaagga gattcgcctg ttcgatgctg ggattcgcca ccgcgaggcc     480
atcgaccgat actcgccac cggggtgcga gaggtgccgc agtcccgctc cgtcgacgtc      540
tccgacgatc catccggctt ccgccgtcgg gtggcggtag ccgtcgatga aatcgctgcc     600
```

```
ggccgctacc acaaggtgat tctgtcccgt tgtgtcgaag tgcctttcgc gatcgacttt    660
ccgttgacct accggctggg gcgtcggcac aacaccccgg tgaggtcgtt tttgttgcag    720
ttgggcggaa tccgtgctct gggttacagc cccgaactcg tcacggcggt gcgcgccgac    780
ggagtggtga tcaccgagcc gttggccggt accgcgcgcct tgggccgtgg tcccgccatt    840
gaccgactgg ctcgtgatga cctggaatca aactccaaag aaattgtcga gcacgccatt    900
tcagtgcgct cttcgcttga ggagattacc gacatcgccg aaccagggag tgctgcggtc    960
atcgatttca tgacggtgcg cgagcgcggc agtgtgcagc acctcggctc caccatcaga   1020
gcacggttgg atccatcgag cgaccggatg gccgccctgg aagcccttt tcctgctgtc    1080 actgcatccg gaatcccgaa agcagctggc gttgaggcca tctttcgcct cgatgagtgc   1140
ccacgtgggc tgtattccgg tgcggtggtg atgctttcgg cggatggcgg gctagacgcc   1200
gcgctgacgc tgcgggcggc ataccaggtc ggcgggcgga cttggctgcg ggccggcgcc   1260
ggcatcatcg aagaatcgga gccagagcgc gaattcgagg agacttgcga aaagctatcc   1320
acattgacgc cttatctggt tgcacgccag taa                                1353
```

<210> SEQ ID NO 3
<211> LENGTH: 450
<212> TYPE: PRT
<213> ORGANISM: Mycobacterium tuberculosis
<220> FEATURE:
<221> NAME/KEY: MISC_FEATURE
<223> OTHER INFORMATION: Strain CDC1551

<400> SEQUENCE: 3

```
Met Ser Glu Leu Ser Val Ala Thr Gly Ala Val Ser Thr Ala Ser Ser
1               5                   10                  15

Ser Ile Pro Met Pro Ala Gly Val Asn Pro Ala Asp Leu Ala Ala Glu
            20                  25                  30

Leu Ala Ala Val Val Thr Glu Ser Val Asp Glu Asp Tyr Leu Leu Tyr
        35                  40                  45

Glu Cys Asp Gly Gln Trp Val Leu Ala Ala Gly Val Gln Ala Met Val
    50                  55                  60

Glu Leu Asp Ser Asp Glu Leu Arg Val Ile Arg Asp Gly Val Thr Arg
65                  70                  75                  80

Arg Gln Gln Trp Ser Gly Arg Pro Gly Ala Ala Leu Gly Glu Ala Val
                85                  90                  95

Asp Arg Leu Leu Leu Glu Thr Asp Gln Ala Phe Gly Trp Val Ala Phe
            100                 105                 110

Glu Phe Gly Val His Arg Tyr Gly Leu Gln Gln Arg Leu Ala Pro His
        115                 120                 125

Thr Pro Leu Ala Arg Val Phe Ser Pro Arg Thr Arg Ile Met Val Ser
    130                 135                 140

Glu Lys Glu Ile Arg Leu Phe Asp Ala Gly Ile Arg His Arg Glu Ala
145                 150                 155                 160

Ile Asp Arg Leu Leu Ala Thr Gly Val Arg Glu Val Pro Gln Ser Arg
                165                 170                 175

Ser Val Asp Val Ser Asp Pro Ser Gly Phe Arg Arg Val Ala
            180                 185                 190

Val Ala Val Asp Glu Ile Ala Ala Gly Arg Tyr His Lys Val Ile Leu
        195                 200                 205

Ser Arg Cys Val Glu Val Pro Phe Ala Ile Asp Phe Pro Leu Thr Tyr
    210                 215                 220
```

-continued

```
Arg Leu Gly Arg Arg His Asn Thr Pro Val Arg Ser Phe Leu Leu Gln
225                 230                 235                 240

Leu Gly Gly Ile Arg Ala Leu Gly Tyr Ser Pro Glu Leu Val Thr Ala
            245                 250                 255

Val Arg Ala Asp Gly Val Val Ile Thr Glu Pro Leu Ala Gly Thr Arg
        260                 265                 270

Ala Leu Gly Arg Gly Pro Ala Ile Asp Arg Leu Ala Arg Asp Asp Leu
    275                 280                 285

Glu Ser Asn Ser Lys Glu Ile Val Glu His Ala Ile Ser Val Arg Ser
290                 295                 300

Ser Leu Glu Glu Ile Thr Asp Ile Ala Glu Pro Gly Ser Ala Ala Val
305                 310                 315                 320

Ile Asp Phe Met Thr Val Arg Glu Arg Gly Ser Val Gln His Leu Gly
                325                 330                 335

Ser Thr Ile Arg Ala Arg Leu Asp Pro Ser Ser Asp Arg Met Ala Ala
            340                 345                 350

Leu Glu Ala Leu Phe Pro Ala Val Thr Ala Ser Gly Ile Pro Lys Ala
        355                 360                 365

Ala Gly Val Glu Ala Ile Phe Arg Leu Asp Glu Cys Pro Arg Gly Leu
    370                 375                 380

Tyr Ser Gly Ala Val Val Met Leu Ser Ala Asp Gly Gly Leu Asp Ala
385                 390                 395                 400

Ala Leu Thr Leu Arg Ala Ala Tyr Gln Val Gly Gly Arg Thr Trp Leu
                405                 410                 415

Arg Ala Gly Ala Gly Ile Ile Glu Glu Ser Gly Pro Gly Arg Glu Phe
            420                 425                 430

Glu Glu Thr Cys Glu Lys Leu Ser Thr Leu Thr Pro Tyr Leu Val Ala
        435                 440                 445

Arg Gln
    450

<210> SEQ ID NO 4
<211> LENGTH: 450
<212> TYPE: PRT
<213> ORGANISM: Mycobacterium tuberculosis
<220> FEATURE:
<221> NAME/KEY: MISC_FEATURE
<223> OTHER INFORMATION: Strain F11

<400> SEQUENCE: 4

Met Ser Glu Leu Ser Val Ala Thr Gly Ala Val Ser Thr Ala Ser Ser
1               5                   10                  15

Ser Ile Pro Met Pro Ala Gly Val Asn Pro Ala Asp Leu Ala Ala Glu
            20                  25                  30

Leu Ala Val Val Thr Glu Ser Val Asp Glu Asp Tyr Leu Leu Tyr
        35                  40                  45

Glu Cys Asp Gly Gln Trp Val Leu Ala Ala Gly Val Gln Ala Met Val
    50                  55                  60

Glu Leu Asp Ser Asp Glu Leu Arg Val Ile Arg Asp Gly Val Thr Arg
65                  70                  75                  80

Arg Gln Gln Trp Ser Gly Arg Pro Gly Ala Ala Leu Gly Glu Ala Val
                85                  90                  95

Asp Arg Leu Leu Leu Glu Thr Asp Gln Ala Phe Gly Trp Val Ala Phe
            100                 105                 110

Glu Phe Gly Val His Arg Tyr Gly Leu Gln Gln Arg Leu Ala Pro His
        115                 120                 125
```

Thr Pro Leu Ala Arg Val Phe Ser Pro Arg Thr Arg Ile Met Val Ser
    130                 135                 140

Glu Lys Glu Ile Arg Leu Phe Asp Ala Gly Ile Arg His Arg Glu Ala
145                 150                 155                 160

Ile Asp Arg Leu Leu Ala Thr Gly Val Arg Glu Val Pro Gln Ser Arg
                165                 170                 175

Ser Val Asp Val Ser Asp Pro Ser Gly Phe Arg Arg Val Ala
            180                 185                 190

Val Ala Val Asp Glu Ile Ala Ala Gly Arg Tyr His Lys Val Ile Leu
            195                 200                 205

Ser Arg Cys Val Glu Val Pro Phe Ala Ile Asp Phe Pro Leu Thr Tyr
210                 215                 220

Arg Leu Gly Arg Arg His Asn Thr Pro Val Arg Ser Phe Leu Leu Gln
225                 230                 235                 240

Leu Gly Gly Ile Arg Ala Leu Gly Tyr Ser Pro Glu Leu Val Thr Ala
                245                 250                 255

Val Arg Ala Asp Gly Val Val Ile Thr Glu Pro Leu Ala Gly Thr Arg
            260                 265                 270

Ala Leu Gly Arg Gly Pro Ala Ile Asp Arg Leu Ala Arg Asp Asp Leu
            275                 280                 285

Glu Ser Asn Ser Lys Glu Ile Val Glu His Ala Ile Ser Val Arg Ser
290                 295                 300

Ser Leu Glu Glu Ile Thr Asp Ile Ala Glu Pro Gly Ser Ala Ala Val
305                 310                 315                 320

Ile Asp Phe Met Thr Val Arg Glu Arg Gly Ser Val Gln His Leu Gly
                325                 330                 335

Ser Thr Ile Arg Ala Arg Leu Asp Pro Ser Ser Asp Arg Met Ala Ala
            340                 345                 350

Leu Glu Ala Leu Phe Pro Ala Val Thr Ala Ser Gly Ile Pro Lys Ala
            355                 360                 365

Ala Gly Val Glu Ala Ile Phe Arg Leu Asp Glu Cys Pro Arg Gly Leu
370                 375                 380

Tyr Ser Gly Ala Val Val Met Leu Ser Ala Asp Gly Gly Leu Asp Ala
385                 390                 395                 400

Ala Leu Thr Leu Arg Ala Ala Tyr Gln Val Gly Gly Arg Thr Trp Leu
                405                 410                 415

Arg Ala Gly Ala Gly Ile Ile Glu Glu Ser Glu Pro Glu Arg Glu Phe
            420                 425                 430

Glu Glu Thr Cys Glu Lys Leu Ser Thr Leu Thr Pro Tyr Leu Val Ala
            435                 440                 445

Arg Gln
    450

<210> SEQ ID NO 5
<211> LENGTH: 450
<212> TYPE: PRT
<213> ORGANISM: Mycobacterium tuberculosis
<220> FEATURE:
<221> NAME/KEY: MISC_FEATURE
<223> OTHER INFORMATION: Strain Haarlem A

<400> SEQUENCE: 5

Met Ser Glu Leu Ser Val Ala Thr Gly Ala Val Ser Thr Ala Ser Ser
1               5                   10                  15

Ser Ile Pro Met Pro Ala Gly Val Asn Pro Ala Asp Leu Ala Ala Glu

-continued

```
             20                  25                  30
Leu Ala Ala Val Val Thr Glu Ser Val Asp Glu Asp Tyr Leu Leu Tyr
         35                  40                  45
Glu Cys Asp Gly Gln Trp Val Leu Ala Gly Val Gln Ala Met Val
     50                  55                  60
Glu Leu Asp Ser Asp Glu Leu Arg Val Ile Arg Asp Gly Val Thr Arg
 65                  70                  75                  80
Arg Gln Gln Trp Ser Gly Arg Pro Gly Ala Ala Leu Gly Glu Ala Val
                 85                  90                  95
Asp Arg Leu Leu Leu Glu Thr Asp Gln Ala Phe Gly Trp Val Ala Phe
            100                 105                 110
Glu Phe Gly Val His Arg Tyr Gly Leu Gln Gln Arg Leu Ala Pro His
        115                 120                 125
Thr Pro Leu Ala Arg Val Phe Ser Pro Arg Thr Arg Ile Met Val Ser
    130                 135                 140
Glu Lys Glu Ile Arg Leu Phe Asp Ala Gly Ile Arg His Arg Glu Ala
145                 150                 155                 160
Ile Asp Arg Leu Leu Ala Thr Gly Val Arg Glu Val Pro Gln Ser Arg
                165                 170                 175
Ser Val Asp Val Ser Asp Asp Pro Ser Gly Phe Arg Arg Val Ala
            180                 185                 190
Val Ala Val Asp Glu Ile Ala Ala Gly Arg Tyr His Lys Val Ile Leu
        195                 200                 205
Ser Arg Cys Val Glu Val Pro Phe Ala Ile Asp Phe Pro Leu Thr Tyr
    210                 215                 220
Arg Leu Gly Arg Arg His Asn Thr Pro Val Arg Ser Phe Leu Leu Gln
225                 230                 235                 240
Leu Gly Gly Ile Arg Ala Leu Gly Tyr Ser Pro Glu Leu Val Thr Ala
                245                 250                 255
Val Arg Ala Asp Gly Val Val Ile Thr Glu Pro Leu Ala Gly Thr Arg
            260                 265                 270
Ala Leu Gly Arg Gly Pro Ala Ile Asp Arg Leu Ala Arg Asp Asp Leu
        275                 280                 285
Glu Ser Asn Ser Lys Glu Ile Val Glu His Ala Ile Ser Val Arg Ser
    290                 295                 300
Ser Leu Glu Glu Ile Thr Asp Ile Ala Glu Pro Gly Ser Ala Ala Val
305                 310                 315                 320
Ile Asp Phe Met Thr Val Arg Glu Arg Gly Ser Val Gln His Leu Gly
                325                 330                 335
Ser Thr Ile Arg Ala Arg Leu Asp Pro Ser Ser Asp Arg Met Ala Ala
            340                 345                 350
Leu Glu Ala Leu Phe Pro Ala Val Thr Ala Ser Gly Ile Pro Lys Ala
        355                 360                 365
Ala Gly Val Glu Ala Ile Phe Arg Leu Asp Glu Cys Pro Arg Gly Leu
    370                 375                 380
Tyr Ser Gly Ala Val Val Met Leu Ser Ala Asp Gly Gly Leu Asp Ala
385                 390                 395                 400
Ala Leu Thr Leu Arg Ala Ala Tyr Gln Val Gly Gly Arg Thr Trp Leu
                405                 410                 415
Arg Ala Gly Ala Gly Ile Ile Glu Glu Ser Glu Pro Glu Arg Glu Phe
            420                 425                 430
Glu Glu Thr Cys Glu Lys Leu Ser Thr Leu Thr Pro Tyr Leu Val Ala
        435                 440                 445
```

Arg Gln
    450

<210> SEQ ID NO 6
<211> LENGTH: 450
<212> TYPE: PRT
<213> ORGANISM: Mycobacterium tuberculosis
<220> FEATURE:
<221> NAME/KEY: MISC_FEATURE
<223> OTHER INFORMATION: Strain C

<400> SEQUENCE: 6

Met Ser Glu Leu Ser Val Ala Thr Gly Ala Val Ser Thr Ala Ser Ser
1               5                   10                  15

Ser Ile Pro Met Pro Ala Gly Val Asn Pro Ala Asp Leu Ala Ala Glu
            20                  25                  30

Leu Ala Val Val Thr Glu Ser Val Asp Glu Asp Tyr Leu Leu Tyr
        35                  40                  45

Glu Cys Asp Gly Gln Trp Val Leu Ala Ala Gly Val Gln Ala Met Val
 50                  55                  60

Glu Leu Asp Ser Asp Glu Leu Arg Val Ile Arg Asp Gly Val Thr Arg
65                  70                  75                  80

Arg Gln Gln Trp Ser Gly Arg Pro Gly Ala Ala Leu Gly Glu Ala Val
                85                  90                  95

Asp Arg Leu Leu Leu Glu Thr Asp Gln Ala Phe Gly Trp Val Ala Leu
            100                 105                 110

Glu Phe Gly Val His Arg Tyr Gly Leu Gln Gln Arg Leu Ala Pro His
        115                 120                 125

Thr Pro Leu Ala Arg Val Phe Ser Pro Arg Thr Arg Ile Met Val Ser
130                 135                 140

Glu Lys Glu Ile Arg Leu Phe Asp Ala Gly Ile Arg His Arg Glu Ala
145                 150                 155                 160

Ile Asp Arg Leu Leu Ala Thr Gly Val Arg Glu Val Pro Gln Ser Arg
                165                 170                 175

Ser Val Asp Val Ser Asp Asp Pro Ser Gly Phe Arg Arg Arg Val Ala
            180                 185                 190

Val Ala Val Asp Glu Ile Ala Ala Gly Arg Tyr His Lys Val Ile Leu
        195                 200                 205

Ser Arg Cys Val Glu Val Pro Phe Ala Ile Asp Phe Pro Leu Thr Tyr
210                 215                 220

Arg Leu Gly Arg Arg His Asn Thr Pro Val Arg Ser Phe Leu Leu Gln
225                 230                 235                 240

Leu Gly Gly Ile Arg Ala Leu Gly Tyr Ser Pro Glu Leu Val Thr Ala
                245                 250                 255

Val Arg Ala Asp Gly Val Val Ile Thr Glu Pro Leu Ala Gly Thr Arg
            260                 265                 270

Ala Leu Gly Arg Gly Pro Ala Ile Asp Arg Leu Ala Arg Asp Asp Leu
        275                 280                 285

Glu Ser Asn Ser Lys Glu Ile Val Glu His Ala Ile Ser Val Arg Ser
    290                 295                 300

Ser Leu Glu Glu Ile Thr Asp Ile Ala Glu Pro Gly Ser Ala Ala Val
305                 310                 315                 320

Ile Asp Phe Met Thr Val Arg Glu Arg Gly Ser Val Gln His Leu Gly
                325                 330                 335

Ser Thr Ile Arg Ala Arg Leu Asp Pro Ser Ser Asp Arg Met Ala Ala

```
            340                 345                 350
Leu Glu Ala Leu Phe Pro Ala Val Thr Ala Ser Gly Ile Pro Lys Ala
            355                 360                 365

Ala Gly Val Glu Ala Ile Phe Arg Leu Asp Glu Cys Pro Arg Gly Leu
        370                 375                 380

Tyr Ser Gly Ala Val Val Met Leu Ser Ala Asp Gly Gly Leu Asp Ala
385                 390                 395                 400

Ala Leu Thr Leu Arg Ala Ala Tyr Gln Val Gly Gly Arg Thr Trp Leu
                405                 410                 415

Arg Ala Gly Ala Gly Ile Ile Glu Glu Ser Glu Pro Glu Arg Glu Phe
            420                 425                 430

Glu Glu Thr Cys Glu Lys Leu Ser Thr Leu Thr Pro Tyr Leu Val Ala
        435                 440                 445

Arg Gln
    450

<210> SEQ ID NO 7
<211> LENGTH: 450
<212> TYPE: PRT
<213> ORGANISM: Mycobacterium bovis
<220

```
Leu Gly Gly Ile Arg Ala Leu Gly Tyr Ser Pro Glu Leu Val Thr Ala
                245                 250                 255

Val Arg Ala Asp Gly Val Val Ile Thr Glu Pro Leu Ala Gly Thr Arg
            260                 265                 270

Ala Leu Gly Arg Gly Pro Ala Ile Asp Arg Leu Ala Arg Asp Asp Leu
        275                 280                 285

Glu Ser Asn Ser Lys Glu Ile Val Glu His Ala Ile Ser Val Arg Ser
    290                 295                 300

Ser Leu Glu Glu Ile Thr Asp Ile Ala Glu Pro Gly Ser Ala Ala Val
305                 310                 315                 320

Ile Asp Phe Met Thr Val Arg Glu Arg Gly Ser Val Gln His Leu Gly
                325                 330                 335

Ser Thr Ile Arg Ala Arg Leu Asp Pro Ser Ser Asp Arg Met Ala Ala
            340                 345                 350

Leu Glu Ala Leu Phe Pro Ala Val Thr Ala Ser Gly Ile Pro Lys Ala
        355                 360                 365

Ala Gly Val Glu Ala Ile Phe Arg Leu Asp Glu Cys Pro Arg Gly Leu
    370                 375                 380

Tyr Ser Gly Ala Val Val Met Leu Ser Ala Asp Gly Gly Leu Asp Ala
385                 390                 395                 400

Ala Leu Thr Leu Arg Ala Ala Tyr Gln Val Gly Gly Arg Thr Trp Leu
                405                 410                 415

Arg Ala Gly Ala Gly Ile Ile Glu Glu Ser Glu Pro Glu Arg Glu Phe
            420                 425                 430

Glu Glu Thr Cys Glu Lys Leu Ser Thr Leu Thr Pro Tyr Leu Val Ala
        435                 440                 445

Arg Gln
    450

<210> SEQ ID NO 8
<211> LENGTH: 110
<212> TYPE: PRT
<213> ORGANISM: Mycobacterium tuberculosis
<220> FEATURE:
<221> NAME/KEY: mat_peptide
<222> LOCATION: (29)..(110)

<400> SEQUENCE: 8

Met Arg Leu Ser Leu Thr Ala Leu Ser Ala Gly Val Gly Ala Val Ala
            -25                 -20                 -15

Met Ser Leu Thr Val Gly Ala Gly Val Ala Ser Ala Asp Pro Val Asp
-10                  -5                  -1   1

Ala Val Ile Asn Thr Thr Cys Asn Tyr Gly Gln Val Val Ala Ala Leu
5                   10                  15                  20

Asn Ala Thr Asp Pro Gly Ala Ala Ala Gln Phe Asn Ala Ser Pro Val
                25                  30                  35

Ala Gln Ser Tyr Leu Arg Asn Phe Leu Ala Ala Pro Pro Gln Arg
            40                  45                  50

Ala Ala Met Ala Ala Gln Leu Gln Ala Val Pro Gly Ala Ala Gln Tyr
        55                  60                  65

Ile Gly Leu Val Glu Ser Val Ala Gly Ser Cys Asn Asn Tyr
    70                  75                  80

<210> SEQ ID NO 9
<211> LENGTH: 97
<212> TYPE: PRT
<213> ORGANISM: Mycobacterium tuberculosis
```

<400> SEQUENCE: 9

Met Ser Leu Leu Asp Ala His Ile Pro Gln Leu Val Ala Ser Gln Ser
1               5                   10                  15

Ala Phe Ala Ala Lys Ala Gly Leu Met Arg His Thr Ile Gly Gln Ala
            20                  25                  30

Glu Gln Ala Ala Met Ser Ala Gln Phe His Gln Gly Glu Ser Ser
        35                  40                  45

Ala Ala Phe Gln Ala Ala His Ala Arg Phe Val Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ser Thr Tyr Thr Gly
                85                  90                  95

Phe

<210> SEQ ID NO 10
<211> LENGTH: 94
<212> TYPE: PRT
<213> ORGANISM: Mycobacterium tuberculosis

<400> SEQUENCE: 10

Met Thr Ile Asn Tyr Gln Phe Gly Asp Val Asp Ala His Gly Ala Met
1               5                   10                  15

Ile Arg Ala Gln Ala Ala Ser Leu Glu Ala Glu His Gln Ala Ile Val
            20                  25                  30

Arg Asp Val Leu Ala Ala Gly Asp Phe Trp Gly Gly Ala Gly Ser Val
        35                  40                  45

Ala Cys Gln Glu Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90

<210> SEQ ID NO 11
<211> LENGTH: 132
<212> TYPE: PRT
<213> ORGANISM: Mycobacterium tuberculosis

<400> SEQUENCE: 11

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
            20                  25                  30

Gly Gly Gly Ser Pro Thr Val His Ile Gly Pro Thr Ala Phe Leu Gly
        35                  40                  45

Leu Gly Val Val Asp Asn Asn Gly Asn Gly Ala Arg Val Gln Arg Val
    50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Thr Trp
                100                 105                 110

Gln Thr Lys Ser Gly Gly Thr Arg Thr Gly Asn Val Thr Leu Ala Glu

```
                115                 120                 125
Gly Pro Pro Ala
    130

<210> SEQ ID NO 12
<211> LENGTH: 195
<212> TYPE: PRT
<213> ORGANISM: Mycobacterium tuberculosis

<400> SEQUENCE: 12

Ala Pro Pro Ala Leu Ser Gln Asp Arg Phe Ala Asp Phe Pro Ala Leu
1               5                   10                  15

Pro Leu Asp Pro Ser Ala Met Val Ala Gln Val Gly Pro Gln Val Val
            20                  25                  30

Asn Ile Asn Thr Lys Leu Gly Tyr Asn Asn Ala Val Gly Ala Gly Thr
        35                  40                  45

Gly Ile Val Ile Asp Pro Asn Gly Val Val Leu Thr Asn Asn His Val
    50                  55                  60

Ile Ala Gly Ala Thr Asp Ile Asn Ala Phe Ser Val Gly Ser Gly Gln
65                  70                  75                  80

Thr Tyr Gly Val Asp Val Val Tyr Asp Arg Thr Gln Asp Val Ala
                85                  90                  95

Val Leu Gln Leu Arg Gly Ala Gly Gly Leu Pro Ser Ala Ala Ile Gly
            100                 105                 110

Gly Gly Val Ala Val Gly Glu Pro Val Val Ala Met Gly Asn Ser Gly
        115                 120                 125

Gly Gln Gly Gly Thr Pro Arg Ala Val Pro Gly Arg Val Val Ala Leu
    130                 135                 140

Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ser
                165                 170                 175

Gly Gly Pro Val Val Asn Gly Leu Gly Gln Val Val Gly Met Asn Thr
            180                 185                 190

Ala Ala Ser
    195

<210> SEQ ID NO 13
<211> LENGTH: 391
<212> TYPE: PRT
<213> ORGANISM: Mycobacterium tuberculosis

<400> SEQUENCE: 13

Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Ala Gln Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Pro Val Ile Ala
```

```
            100                 105                 110
Glu Asn Arg Ala Glu Leu Met Ile Leu Ile Ala Thr Asn Leu Leu Gly
            115                 120                 125

Gln Asn Thr Pro Ala Ile Ala Val Asn Glu Ala Glu Tyr Gly Glu Met
        130                 135                 140

Trp Ala Gln Asp Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                    165                 170                 175

Ser Ala Gly Gly Leu Leu Glu Gln Ala Ala Val Glu Glu Ala Ser
                180                 185                 190

Asp Thr Ala Ala Ala Asn Gln Leu Met Asn Asn Val Pro Gln Ala Leu
                195                 200                 205

Gln Gln Leu Ala Gln Pro Thr Gln Gly Thr Thr Pro Ser Ser Lys Leu
        210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
                260                 265                 270

Ala Ala Ala Gln Ala Val Gln Thr Ala Ala Gln Asn Gly Val Arg Ala
            275                 280                 285

Met Ser Ser Leu Gly Ser Ser Leu Gly Ser Ser Gly Leu Gly Gly Gly
        290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
                340                 345                 350

Gln Met Leu Gly Gly Leu Pro Val Gly Gln Met Gly Ala Arg Ala Gly
            355                 360                 365

Gly Gly Leu Ser Gly Val Leu Arg Val Pro Arg Pro Tyr Val Met
        370                 375                 380

Pro His Ser Pro Ala Ala Gly
385                 390

<210> SEQ ID NO 14
<211> LENGTH: 392
<212> TYPE: PRT
<213> ORGANISM: Mycobacterium tuberculosis

<400> SEQUENCE: 14

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
                20                  25                  30

Tyr Ser Ser Leu Glu Tyr Phe Glu Lys Ala Leu Glu Glu Leu Ala Ala
            35                  40                  45

Ala Phe Pro Gly Asp Gly Trp Leu Gly Ser Ala Ala Asp Lys Tyr Ala
        50                  55                  60

Gly Lys Asn Arg Asn His Val Asn Phe Phe Gln Glu Leu Ala Asp Leu
65                  70                  75                  80
```

```
Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
        115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Ile
            180                 185                 190

Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
    210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
            260                 265                 270

Ser Ala Ser Leu Pro Ala Leu Ala Gly Ile Gly Gly Ser Gly Phe
        275                 280                 285

Gly Gly Leu Pro Ser Leu Ala Gln Val His Ala Ser Thr Arg Gln
    290                 295                 300

Ala Leu Arg Pro Arg Ala Asp Gly Pro Val Gly Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Gly Met His Pro Ser Ser Gly Ala Ser
            340                 345                 350

Lys Gly Thr Thr Thr Lys Lys Tyr Ser Glu Gly Ala Ala Ala Gly Thr
        355                 360                 365

Glu Asp Ala Glu Arg Ala Pro Val Glu Ala Asp Ala Gly Gly Gly Gln
    370                 375                 380

Lys Val Leu Val Arg Asn Val Val
385                 390

<210> SEQ ID NO 15
<211> LENGTH: 423
<212> TYPE: PRT
<213> ORGANISM: Mycobacterium tuberculosis

<400> SEQUENCE: 15

Met Asp Phe Gly Leu Leu Pro Pro Glu Val Asn Ser Ser Arg Met Tyr
1               5                   10                  15

Ser Gly Pro Gly Pro Glu Ser Met Leu Ala Ala Ala Ala Trp Asp
            20                  25                  30

Gly Val Ala Ala Glu Leu Thr Ser Ala Ala Val Ser Tyr Gly Ser Val
        35                  40                  45

Val Ser Thr Leu Ile Val Glu Pro Trp Met Gly Pro Ala Ala Ala Ala
    50                  55                  60
```

```
Met Ala Ala Ala Thr Pro Tyr Val Gly Trp Leu Ala Thr Ala
 65                  70                  75                  80

Ala Leu Ala Lys Glu Thr Ala Thr Gln Ala Arg Ala Ala Ala Glu Ala
                 85                  90                  95

Phe Gly Thr Ala Phe Ala Met Thr Val Pro Pro Ser Leu Val Ala Ala
            100                 105                 110

Asn Arg Ser Arg Leu Met Ser Leu Val Ala Ala Asn Ile Leu Gly Gln
        115                 120                 125

Asn Ser Ala Ala Ile Ala Ala Thr Gln Ala Glu Tyr Ala Glu Met Trp
130                 135                 140

Ala Gln Asp Ala Ala Val Met Tyr Ser Tyr Glu Gly Ala Ser Ala Ala
145                 150                 155                 160

Ala Ser Ala Leu Pro Pro Phe Thr Pro Pro Val Gln Gly Thr Gly Pro
                165                 170                 175

Ala Gly Pro Ala Ala Ala Ala Ala Thr Gln Ala Ala Gly Ala Gly
            180                 185                 190

Ala Val Ala Asp Ala Gln Ala Thr Leu Ala Gln Leu Pro Pro Gly Ile
        195                 200                 205

Leu Ser Asp Ile Leu Ser Ala Leu Ala Ala Asn Ala Asp Pro Leu Thr
210                 215                 220

Ser Gly Leu Leu Gly Ile Ala Ser Thr Leu Asn Pro Gln Val Gly Ser
225                 230                 235                 240

Ala Gln Pro Ile Val Ile Pro Thr Pro Ile Gly Glu Leu Asp Val Ile
                245                 250                 255

Ala Leu Tyr Ile Ala Ser Ile Ala Thr Gly Ser Ile Ala Leu Ala Ile
            260                 265                 270

Thr Asn Thr Ala Arg Pro Trp His Ile Gly Leu Tyr Gly Asn Ala Gly
        275                 280                 285

Gly Leu Gly Pro Thr Gln Gly His Pro Leu Ser Ser Ala Thr Asp Glu
290                 295                 300

Pro Glu Pro His Trp Gly Pro Phe Gly Gly Ala Ala Pro Val Ser Ala
305                 310                 315                 320

Gly Val Gly His Ala Ala Leu Val Gly Ala Leu Ser Val Pro His Ser
                325                 330                 335

Trp Thr Thr Ala Ala Pro Glu Ile Gln Leu Ala Val Gln Ala Thr Pro
            340                 345                 350

Thr Phe Ser Ser Ser Ala Gly Ala Asp Pro Thr Ala Leu Asn Gly Met
        355                 360                 365

Pro Ala Gly Leu Leu Ser Gly Met Ala Leu Ala Ser Leu Ala Ala Arg
                370                 375                 380

Gly Thr Thr Gly Gly Gly Thr Arg Ser Gly Thr Ser Thr Asp Gly
385                 390                 395                 400

Gln Glu Asp Gly Arg Lys Pro Pro Val Val Ile Arg Glu Gln Pro
                405                 410                 415

Pro Pro Gly Asn Pro Pro Arg
            420

<210> SEQ ID NO 16
<211> LENGTH: 95
<212> TYPE: PRT
<213> ORGANISM: Mycobacterium tuberculosis
<220> FEATURE:
<221> NAME/KEY: INIT_MET
<222> LOCATION: (1)..(1)
<220> FEATURE:
```

```
<221> NAME/KEY: mat_peptide
<222> LOCATION: (2)..(95)

<400> SEQUENCE: 16

Met Thr Glu Gln Gln Trp Asn Phe Ala Gly Ile Glu Ala Ala Ala Ser
 -1   1               5                  10                  15

Ala Ile Gln Gly Asn Val Thr Ser Ile His Ser Leu Leu Asp Glu Gly
             20                  25                  30

Lys Gln Ser Leu Thr Lys Leu Ala Ala Trp Gly Gly Ser Gly Ser
             35                  40                  45

Glu Ala Tyr Gln Gly Val Gln Gln Lys Trp Asp Ala Thr Ala Thr Glu
             50                  55                  60

Leu Asn Asn Ala Leu Gln Asn Leu Ala Arg Thr Ile Ser Glu Ala Gly
 65              70                  75

Gln Ala Met Ala Ser Thr Glu Gly Asn Val Thr Gly Met Phe Ala
 80              85                  90

<210> SEQ ID NO 17
<211> LENGTH: 338
<212> TYPE: PRT
<213> ORGANISM: Mycobacterium tuberculosis
<220> FEATURE:
<221> NAME/KEY: mat_peptide
<222> LOCATION: (43)..(338)

<400> SEQUENCE: 17

Met Gln Leu Val Asp Arg Val Arg Gly Ala Val Thr Gly Met Ser Arg
             -40                 -35                 -30

Arg Leu Val Val Gly Ala Val Gly Ala Ala Leu Val Ser Gly Leu Val
             -25                 -20                 -15

Gly Ala Val Gly Gly Thr Ala Thr Ala Gly Ala Phe Ser Arg Pro Gly
 -10              -5                  -1  1                5

Leu Pro Val Glu Tyr Leu Gln Val Pro Ser Pro Ser Met Gly Arg Asp
             10                  15                  20

Ile Lys Val Gln Phe Gln Ser Gly Gly Ala Asn Ser Pro Ala Leu Tyr
             25                  30                  35

Leu Leu Asp Gly Leu Arg Ala Gln Asp Asp Phe Ser Gly Trp Asp Ile
             40                  45                  50

Asn Thr Pro Ala Phe Glu Trp Tyr Asp Gln Ser Gly Leu Ser Val Val
 55              60                  65                  70

Met Pro Val Gly Gly Gln Ser Ser Phe Tyr Ser Asp Trp Tyr Gln Pro
             75                  80                  85

Ala Cys Gly Lys Ala Gly Cys Gln Thr Tyr Lys Trp Glu Thr Phe Leu
             90                  95                  100

Thr Ser Glu Leu Pro Gly Trp Leu Gln Ala Asn Arg His Val Lys Pro
             105                 110                 115

Thr Gly Ser Ala Val Val Gly Leu Ser Met Ala Ala Ser Ser Ala Leu
             120                 125                 130

Thr Leu Ala Ile Tyr His Pro Gln Gln Phe Val Tyr Ala Gly Ala Met
 135             140                 145                 150

Ser Gly Leu Leu Asp Pro Ser Gln Ala Met Gly Pro Thr Leu Ile Gly
             155                 160                 165

Leu Ala Met Gly Asp Ala Gly Gly Tyr Lys Ala Ser Asp Met Trp Gly
             170                 175                 180

Pro Lys Glu Asp Pro Ala Trp Gln Arg Asn Asp Pro Leu Leu Asn Val
             185                 190                 195
```

```
Gly Lys Leu Ile Ala Asn Asn Thr Arg Val Trp Val Tyr Cys Gly Asn
200                 205                 210

Gly Lys Pro Ser Asp Leu Gly Asn Asn Leu Pro Ala Lys Phe Leu
215                 220                 225                 230

Glu Gly Phe Val Arg Thr Ser Asn Ile Lys Phe Gln Asp Ala Tyr Asn
                235                 240                 245

Ala Gly Gly Gly His Asn Gly Val Phe Asp Phe Pro Asp Ser Gly Thr
            250                 255                 260

His Ser Trp Glu Tyr Trp Gly Ala Gln Leu Asn Ala Met Lys Pro Asp
                265                 270                 275

Leu Gln Arg Ala Leu Gly Ala Thr Pro Asn Thr Gly Pro Ala Pro Gln
280                 285                 290

Gly Ala
295

<210> SEQ ID NO 18
<211> LENGTH: 325
<212> TYPE: PRT
<213> ORGANISM: Mycobacterium tuberculosis
<220> FEATURE:
<221> NAME/KEY: mat_peptide
<222> LOCATION: (41)..(325)

<400> SEQUENCE: 18

Met Thr Asp Val Ser Arg Lys Ile Arg Ala Trp Gly Arg Arg Leu Met
-40                 -35                 -30                 -25

Ile Gly Thr Ala Ala Ala Val Val Leu Pro Gly Leu Val Gly Leu Ala
                -20                 -15                 -10

Gly Gly Ala Ala Thr Ala Gly Ala Phe Ser Arg Pro Gly Leu Pro Val
            -5                  -1  1                   5

Glu Tyr Leu Gln Val Pro Ser Pro Ser Met Gly Arg Asp Ile Lys Val
                10                  15                  20

Gln Phe Gln Ser Gly Gly Asn Asn Ser Pro Ala Val Tyr Leu Leu Asp
25                  30                  35                  40

Gly Leu Arg Ala Gln Asp Asp Tyr Asn Gly Trp Asp Ile Asn Thr Pro
                45                  50                  55

Ala Phe Glu Trp Tyr Tyr Gln Ser Gly Leu Ser Ile Val Met Pro Val
                60                  65                  70

Gly Gly Gln Ser Ser Phe Tyr Ser Asp Trp Tyr Ser Pro Ala Cys Gly
                75                  80                  85

Lys Ala Gly Cys Gln Thr Tyr Lys Trp Glu Thr Phe Leu Thr Ser Glu
90                  95                  100

Leu Pro Gln Trp Leu Ser Ala Asn Arg Ala Val Lys Pro Thr Gly Ser
105                 110                 115                 120

Ala Ala Ile Gly Leu Ser Met Ala Gly Ser Ser Ala Met Ile Leu Ala
                125                 130                 135

Ala Tyr His Pro Gln Gln Phe Ile Tyr Ala Gly Ser Leu Ser Ala Leu
            140                 145                 150

Leu Asp Pro Ser Gln Gly Met Gly Pro Ser Leu Ile Gly Leu Ala Met
            155                 160                 165

Gly Asp Ala Gly Gly Tyr Lys Ala Ala Asp Met Trp Gly Pro Ser Ser
            170                 175                 180

Asp Pro Ala Trp Glu Arg Asn Asp Pro Thr Gln Gln Ile Pro Lys Leu
185                 190                 195                 200

Val Ala Asn Asn Thr Arg Leu Trp Val Tyr Cys Gly Asn Gly Thr Pro
                205                 210                 215
```

```
Asn Glu Leu Gly Gly Ala Asn Ile Pro Ala Glu Phe Leu Glu Asn Phe
            220                 225                 230

Val Arg Ser Ser Asn Leu Lys Phe Gln Asp Ala Tyr Asn Ala Ala Gly
            235                 240                 245

Gly His Asn Ala Val Phe Asn Phe Pro Pro Asn Gly Thr His Ser Trp
            250                 255                 260

Glu Tyr Trp Gly Ala Gln Leu Asn Ala Met Lys Gly Asp Leu Gln Ser
265                 270                 275                 280

Ser Leu Gly Ala Gly
            285

<210> SEQ ID NO 19
<211> LENGTH: 144
<212> TYPE: PRT
<213> ORGANISM: Mycobacterium tuberculosis
<220> FEATURE:
<221> NAME/KEY: INIT_MET
<222> LOCATION: (1)..(1)
<220> FEATURE:
<221> NAME/KEY: mat_peptide
<222> LOCATION: (2)..(144)

<400> SEQUENCE: 19

Met Ala Thr Thr Leu Pro Val Gln Arg His Pro Arg Ser Leu Phe Pro
 -1   1           5                  10                  15

Glu Phe Ser Glu Leu Phe Ala Ala Phe Pro Ser Phe Ala Gly Leu Arg
            20                  25                  30

Pro Thr Phe Asp Thr Arg Leu Met Arg Leu Glu Asp Glu Met Lys Glu
            35                  40                  45

Gly Arg Tyr Glu Val Arg Ala Glu Leu Pro Gly Val Asp Pro Asp Lys
            50                  55                  60

Asp Val Asp Ile Met Val Arg Asp Gly Gln Leu Thr Ile Lys Ala Glu
            65                  70                  75

Arg Thr Glu Gln Lys Asp Phe Asp Gly Arg Ser Glu Phe Ala Tyr Gly
80                  85                  90                  95

Ser Phe Val Arg Thr Val Ser Leu Pro Val Gly Ala Asp Glu Asp Asp
            100                 105                 110

Ile Lys Ala Thr Tyr Asp Lys Gly Ile Leu Thr Val Ser Val Ala Val
            115                 120                 125

Ser Glu Gly Lys Pro Thr Glu Lys His Ile Gln Ile Arg Ser Thr Asn
            130                 135                 140

<210> SEQ ID NO 20
<211> LENGTH: 228
<212> TYPE: PRT
<213> ORGANISM: Mycobacterium tuberculosis
<220> FEATURE:
<221> NAME/KEY: mat_peptide
<222> LOCATION: (24)..(228)

<400> SEQUENCE: 20

Met Arg Ile Lys Ile Phe Met Leu Val Thr Ala Val Val Leu Leu Cys
            -20                 -15                 -10

Cys Ser Gly Val Ala Thr Ala Ala Pro Lys Thr Tyr Cys Glu Glu Leu
             -5             -1   1               5

Lys Gly Thr Asp Thr Gly Gln Ala Cys Gln Ile Gln Met Ser Asp Pro
10                  15                  20                  25

Ala Tyr Asn Ile Asn Ile Ser Leu Pro Ser Tyr Tyr Pro Asp Gln Lys
            30                  35                  40
```

```
Ser Leu Glu Asn Tyr Ile Ala Gln Thr Arg Asp Lys Phe Leu Ser Ala
            45                  50                  55

Ala Thr Ser Ser Thr Pro Arg Glu Ala Pro Tyr Glu Leu Asn Ile Thr
        60                  65                  70

Ser Ala Thr Tyr Gln Ser Ala Ile Pro Pro Arg Gly Thr Gln Ala Val
 75                  80                  85

Val Leu Lys Val Tyr Gln Asn Ala Gly Gly Thr His Pro Thr Thr Thr
 90                  95                 100                 105

Tyr Lys Ala Phe Asp Trp Asp Gln Ala Tyr Arg Lys Pro Ile Thr Tyr
                110                 115                 120

Asp Thr Leu Trp Gln Ala Asp Thr Asp Pro Leu Pro Val Val Phe Pro
                125                 130                 135

Ile Val Gln Gly Glu Leu Ser Lys Gln Thr Gly Gln Gln Val Ser Ile
                140                 145                 150

Ala Pro Asn Ala Gly Leu Asp Pro Val Asn Tyr Gln Asn Phe Ala Val
                155                 160                 165

Thr Asn Asp Gly Val Ile Phe Phe Phe Asn Pro Gly Glu Leu Leu Pro
170                 175                 180                 185

Glu Ala Ala Gly Pro Thr Gln Val Leu Val Pro Arg Ser Ala Ile Asp
                190                 195                 200

Ser Met Leu Ala
            205

<210> SEQ ID NO 21
<211> LENGTH: 355
<212> TYPE: PRT
<213> ORGANISM: Mycobacterium tuberculosis
<220> FEATURE:
<221> NAME/KEY: mat_peptide
<222> LOCATION: (33)..(355)

<400> SEQUENCE: 21

Met Ser Asn Ser Arg Arg Arg Ser Leu Arg Trp Ser Trp Leu Leu Ser
        -30                 -25                 -20

Val Leu Ala Ala Val Gly Leu Gly Leu Ala Thr Ala Pro Ala Gln Ala
    -15                 -10                  -5                  -1

Ala Pro Pro Ala Leu Ser Gln Asp Arg Phe Ala Asp Phe Pro Ala Leu
 1                   5                  10                  15

Pro Leu Asp Pro Ser Ala Met Val Ala Gln Val Gly Pro Gln Val Val
                 20                  25                  30

Asn Ile Asn Thr Lys Leu Gly Tyr Asn Asn Ala Val Gly Ala Gly Thr
                35                  40                  45

Gly Ile Val Ile Asp Pro Asn Gly Val Val Leu Thr Asn Asn His Val
50                  55                  60

Ile Ala Gly Ala Thr Asp Ile Asn Ala Phe Ser Val Gly Ser Gly Gln
65                  70                  75                  80

Thr Tyr Gly Val Asp Val Val Gly Tyr Asp Arg Thr Gln Asp Val Ala
                85                  90                  95

Val Leu Gln Leu Arg Gly Ala Gly Gly Leu Pro Ser Ala Ala Ile Gly
                100                 105                 110

Gly Gly Val Ala Val Gly Glu Pro Val Val Ala Met Gly Asn Ser Gly
                115                 120                 125

Gly Gln Gly Gly Thr Pro Arg Ala Val Pro Gly Arg Val Val Ala Leu
                130                 135                 140

Gly Gln Thr Val Gln Ala Ser Asp Ser Leu Thr Gly Ala Glu Glu Thr
```

```
          145                 150                 155                 160
Leu Asn Gly Leu Ile Gln Phe Asp Ala Ala Ile Gln Pro Gly Asp Ser
                    165                 170                 175
Gly Gly Pro Val Val Asn Gly Leu Gly Gln Val Val Gly Met Asn Thr
                180                 185                 190
Ala Ala Ser Asp Asn Phe Gln Leu Ser Gln Gly Gly Gln Gly Phe Ala
                195                 200                 205
Ile Pro Ile Gly Gln Ala Met Ala Ile Ala Gly Gln Ile Arg Ser Gly
            210                 215                 220
Gly Gly Ser Pro Thr Val His Ile Gly Pro Thr Ala Phe Leu Gly Leu
225                 230                 235                 240
Gly Val Val Asp Asn Asn Gly Asn Gly Ala Arg Val Gln Arg Val Val
                245                 250                 255
Gly Ser Ala Pro Ala Ala Ser Leu Gly Ile Ser Thr Gly Asp Val Ile
                260                 265                 270
Thr Ala Val Asp Gly Ala Pro Ile Asn Ser Ala Thr Ala Met Ala Asp
                275                 280                 285
Ala Leu Asn Gly His His Pro Gly Asp Val Ile Ser Val Thr Trp Gln
                290                 295                 300
Thr Lys Ser Gly Gly Thr Arg Thr Gly Asn Val Thr Leu Ala Glu Gly
305                 310                 315                 320
Pro Pro Ala

<210> SEQ ID NO 22
<211> LENGTH: 323
<212> TYPE: PRT
<213> ORGANISM: Artificial Sequence
<220> FEATURE:
<223> OTHER INFORMATION: Ser/Ala mutant of mature Mtb32A

<400> SEQUENCE: 22

Ala Pro Pro Ala Leu Ser Gln Asp Arg Phe Ala Asp Phe Pro Ala Leu
1               5                   10                  15
Pro Leu Asp Pro Ser Ala Met Val Ala Gln Val Gly Pro Gln Val Val
                20                  25                  30
Asn Ile Asn Thr Lys Leu Gly Tyr Asn Asn Ala Val Gly Ala Gly Thr
            35                  40                  45
Gly Ile Val Ile Asp Pro Asn Gly Val Val Leu Thr Asn Asn His Val
        50                  55                  60
Ile Ala Gly Ala Thr Asp Ile Asn Ala Phe Ser Val Gly Ser Gly Gln
65                  70                  75                  80
Thr Tyr Gly Val Asp Val Val Gly Tyr Asp Arg Thr Gln Asp Val Ala
                85                  90                  95
Val Leu Gln Leu Arg Gly Ala Gly Gly Leu Pro Ser Ala Ala Ile Gly
                100                 105                 110
Gly Gly Val Ala Val Gly Glu Pro Val Ala Met Gly Asn Ser Gly
                115                 120                 125
Gly Gln Gly Gly Thr Pro Arg Ala Val Pro Gly Arg Val Val Ala Leu
            130                 135                 140
Gly Gln Thr Val Gln Ala Ser Asp Ser Leu Thr Gly Ala Glu Glu Thr
145                 150                 155                 160
Leu Asn Gly Leu Ile Gln Phe Asp Ala Ala Ile Gln Pro Gly Asp Ala
                    165                 170                 175
Gly Gly Pro Val Val Asn Gly Leu Gly Gln Val Val Gly Met Asn Thr
                180                 185                 190
```

```
Ala Ala Ser Asp Asn Phe Gln Leu Ser Gln Gly Gly Gln Gly Phe Ala
        195                 200                 205
Ile Pro Ile Gly Gln Ala Met Ala Ile Ala Gly Gln Ile Arg Ser Gly
        210                 215                 220
Gly Gly Ser Pro Thr Val His Ile Gly Pro Thr Ala Phe Leu Gly Leu
225                 230                 235                 240
Gly Val Val Asp Asn Asn Gly Asn Gly Ala Arg Val Gln Arg Val Val
                245                 250                 255
Gly Ser Ala Pro Ala Ala Ser Leu Gly Ile Ser Thr Gly Asp Val Ile
                260                 265                 270
Thr Ala Val Asp Gly Ala Pro Ile Asn Ser Ala Thr Ala Met Ala Asp
                275                 280                 285
Ala Leu Asn Gly His His Pro Gly Asp Val Ile Ser Val Thr Trp Gln
        290                 295                 300
Thr Lys Ser Gly Gly Thr Arg Thr Gly Asn Val Thr Leu Ala Glu Gly
305                 310                 315                 320
Pro Pro Ala
```

<210> SEQ ID NO 23
<211> LENGTH: 96
<212> TYPE: PRT
<213> ORGANISM: Mycobacterium tuberculosis

<400> SEQUENCE: 23

```
Met Ser Gln Ile Met Tyr Asn Tyr Pro Ala Met Leu Gly His Ala Gly
1               5                   10                  15
Asp Met Ala Gly Tyr Ala Gly Thr Leu Gln Ser Leu Gly Ala Glu Ile
            20                  25                  30
Ala Val Glu Gln Ala Ala Leu Gln Ser Ala Trp Gln Gly Asp Thr Gly
        35                  40                  45
Ile Thr Tyr Gln Ala Trp Gln Ala Gln Trp Asn Gln Ala Met Glu Asp
    50                  55                  60
Leu Val Arg Ala Tyr His Ala Met Ser Ser Thr His Glu Ala Asn Thr
65                  70                  75                  80
Met Ala Met Met Ala Arg Asp Thr Ala Glu Ala Ala Lys Trp Gly Gly
                85                  90                  95
```

<210> SEQ ID NO 24
<211> LENGTH: 723
<212> TYPE: PRT
<213> ORGANISM: Artificial Sequence
<220> FEATURE:
<223> OTHER INFORMATION: Mtb72f

<400> SEQUENCE: 24

```
Met Thr Ala Ala Ser Asp Asn Phe Gln Leu Ser Gln Gly Gly Gln Gly
1               5                   10                  15
Phe Ala Ile Pro Ile Gly Gln Ala Met Ala Ile Ala Gly Gln Ile Arg
            20                  25                  30
Ser Gly Gly Gly Ser Pro Thr Val His Ile Gly Pro Thr Ala Phe Leu
        35                  40                  45
Gly Leu Gly Val Val Asp Asn Asn Gly Asn Gly Ala Arg Val Gln Arg
    50                  55                  60
Val Val Gly Ser Ala Pro Ala Ala Ser Leu Gly Ile Ser Thr Gly Asp
65                  70                  75                  80
Val Ile Thr Ala Val Asp Gly Ala Pro Ile Asn Ser Ala Thr Ala Met
```

```
                    85                  90                  95
Ala Asp Ala Leu Asn Gly His His Pro Gly Asp Val Ile Ser Val Thr
                100                 105                 110

Trp Gln Thr Lys Ser Gly Gly Thr Arg Thr Gly Asn Val Thr Leu Ala
                115                 120                 125

Glu Gly Pro Pro Ala Glu Phe Met Val Asp Phe Gly Ala Leu Pro Pro
            130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
                180                 185                 190

Trp Ile Gly Ser Ser Ala Gly Leu Met Val Ala Ala Ser Pro Tyr
                195                 200                 205

Val Ala Trp Met Ser Val Thr Ala Gly Gln Ala Glu Leu Thr Ala Ala
        210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                    245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
            275                 280                 285

Gly Tyr Ala Ala Ala Thr Ala Thr Ala Thr Leu Leu Pro Phe
        290                 295                 300

Glu Glu Ala Pro Glu Met Thr Ser Ala Gly Leu Leu Glu Gln Ala
305                 310                 315                 320

Ala Ala Val Glu Glu Ala Ser Asp Thr Ala Ala Ala Asn Gln Leu Met
                325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
        355                 360                 365

His Arg Ser Pro Ile Ser Asn Met Val Ser Met Ala Asn Asn His Met
        370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Gly Val Ala Ala Asn Leu Gly Arg Ala Ala
            435                 440                 445

Ser Val Gly Ser Leu Ser Val Pro Gln Ala Trp Ala Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
            485                 490                 495

Gln Met Gly Ala Arg Ala Gly Gly Gly Leu Ser Gly Val Leu Arg Val
            500                 505                 510
```

```
Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
    530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
        595                 600                 605

Thr Tyr Gly Val Asp Val Val Gly Tyr Asp Arg Thr Gln Asp Val Ala
    610                 615                 620

Val Leu Gln Leu Arg Gly Ala Gly Leu Pro Ser Ala Ala Ile Gly
625                 630                 635                 640

Gly Gly Val Ala Val Gly Glu Pro Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
        675                 680                 685

Leu Asn Gly Leu Ile Gln Phe Asp Ala Ala Ile Gln Pro Gly Asp Ser
    690                 695                 700

Gly Gly Pro Val Val Asn Gly Leu Gly Gln Val Val Gly Met Asn Thr
705                 710                 715                 720

Ala Ala Ser

<210> SEQ ID NO 25
<211> LENGTH: 723
<212> TYPE: PRT
<213> ORGANISM: Artificial Sequence
<220> FEATURE:
<223> OTHER INFORMATION: M72

<400> SEQUENCE: 25

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140
```

-continued

```
Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Tyr Glu Thr Ala Tyr Gly Leu Thr
225                 230                 235                 240

Val Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
                260                 265                 270

Glu Ala Glu Tyr Gly Glu Met Trp Ala Gln Asp Ala Ala Ala Met Phe
            275                 280                 285

Gly Tyr Ala Ala Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Asn Gln Leu Met
                325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
                355                 360                 365

His Arg Ser Pro Ile Ser Asn Met Val Ser Met Ala Asn Asn His Met
            370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Val Ala Ala Asn Leu Gly Arg Ala Ala
        435                 440                 445

Ser Val Gly Ser Leu Ser Val Pro Gln Ala Trp Ala Ala Ala Asn Gln
    450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
    530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
```

565                 570                 575
Gly Ile Val Ile Asp Pro Asn Gly Val Val Leu Thr Asn Asn His Val
                580                 585                 590

Ile Ala Gly Ala Thr Asp Ile Asn Ala Phe Ser Val Gly Ser Gly Gln
                595                 600                 605

Thr Tyr Gly Val Asp Val Val Gly Tyr Asp Arg Thr Gln Asp Val Ala
            610                 615                 620

Val Leu Gln Leu Arg Gly Ala Gly Leu Pro Ser Ala Ala Ile Gly
625                 630                 635                 640

Gly Gly Val Ala Val Gly Glu Pro Val Ala Met Gly Asn Ser Gly
                645                 650                 655

Gly Gln Gly Gly Thr Pro Arg Ala Val Pro Gly Arg Val Val Ala Leu
                660                 665                 670

Gly Gln Thr Val Gln Ala Ser Asp Ser Leu Thr Gly Ala Glu Glu Thr
                675                 680                 685

Leu Asn Gly Leu Ile Gln Phe Asp Ala Ala Ile Gln Pro Gly Asp Ala
            690                 695                 700

Gly Gly Pro Val Val Asn Gly Leu Gly Gln Val Val Gly Met Asn Thr
705                 710                 715                 720

Ala Ala Ser

<210> SEQ ID NO 26
<211> LENGTH: 702
<212> TYPE: PRT
<213> ORGANISM: Artificial Sequence
<220> FEATURE:
<223> OTHER INFORMATION: Mtb71f

<400> SEQUENCE: 26

Asp Pro Val Asp Ala Val Ile Asn Thr Thr Cys Asn Tyr Gly Gln Val
1               5                   10                  15

Val Ala Ala Leu Asn Ala Thr Asp Pro Gly Ala Ala Gln Phe Asn
            20                  25                  30

Ala Ser Pro Val Ala Gln Ser Tyr Leu Arg Asn Phe Leu Ala Ala Pro
        35                  40                  45

Pro Pro Gln Arg Ala Ala Met Ala Ala Gln Leu Gln Ala Val Pro Gly
    50                  55                  60

Ala Ala Gln Tyr Ile Gly Leu Val Glu Ser Val Ala Gly Ser Cys Asn
65                  70                  75                  80

Asn Tyr Glu Leu Met Thr Ile Asn Tyr Gln Phe Gly Asp Val Asp Ala
                85                  90                  95

His Gly Ala Met Ile Arg Ala Gln Ala Ala Ser Leu Glu Ala Glu His
            100                 105                 110

Gln Ala Ile Val Arg Asp Val Leu Ala Ala Gly Asp Phe Trp Gly Gly
        115                 120                 125

Ala Gly Ser Val Ala Cys Gln Glu Phe Ile Thr Gln Leu Gly Arg Asn
    130                 135                 140

Phe Gln Val Ile Tyr Glu Gln Ala Asn Ala His Gly Gln Lys Val Gln
145                 150                 155                 160

Ala Ala Gly Asn Asn Met Ala Gln Thr Asp Ser Ala Val Gly Ser Ser
                165                 170                 175

Trp Ala Thr Ser Met Ser Leu Leu Asp Ala His Ile Pro Gln Leu Val
            180                 185                 190

Ala Ser Gln Ser Ala Phe Ala Ala Lys Ala Gly Leu Met Arg His Thr
        195                 200                 205

```
Ile Gly Gln Ala Glu Gln Ala Met Ser Ala Gln Ala Phe His Gln
    210                 215                 220

Gly Glu Ser Ser Ala Ala Phe Gln Ala Ala His Ala Arg Phe Val Ala
225                 230                 235                 240

Ala Ala Ala Lys Val Asn Thr Leu Leu Asp Val Ala Gln Ala Asn Leu
                245                 250                 255

Gly Glu Ala Ala Gly Thr Tyr Val Ala Ala Asp Ala Ala Ala Ser
                260                 265                 270

Thr Tyr Thr Gly Phe Asp Ile Met Asp Phe Gly Leu Leu Pro Pro Glu
        275                 280                 285

Val Asn Ser Ser Arg Met Tyr Ser Gly Pro Gly Glu Ser Met Leu
290                 295                 300

Ala Ala Ala Ala Ala Trp Asp Gly Val Ala Ala Glu Leu Thr Ser Ala
305                 310                 315                 320

Ala Val Ser Tyr Gly Ser Val Val Ser Thr Leu Ile Val Glu Pro Trp
                325                 330                 335

Met Gly Pro Ala Ala Ala Ala Met Ala Ala Ala Ala Thr Pro Tyr Val
                340                 345                 350

Gly Trp Leu Ala Ala Thr Ala Ala Leu Ala Lys Glu Thr Ala Thr Gln
            355                 360                 365

Ala Arg Ala Ala Ala Glu Ala Phe Gly Thr Ala Phe Ala Met Thr Val
    370                 375                 380

Pro Pro Ser Leu Val Ala Ala Asn Arg Ser Arg Leu Met Ser Leu Val
385                 390                 395                 400

Ala Ala Asn Ile Leu Gly Gln Asn Ser Ala Ala Ile Ala Ala Thr Gln
                405                 410                 415

Ala Glu Tyr Ala Glu Met Trp Ala Gln Asp Ala Ala Val Met Tyr Ser
            420                 425                 430

Tyr Glu Gly Ala Ser Ala Ala Ser Ala Leu Pro Pro Phe Thr Pro
            435                 440                 445

Pro Val Gln Gly Thr Gly Pro Ala Gly Pro Ala Ala Ala Ala Ala
    450                 455                 460

Thr Gln Ala Ala Gly Ala Gly Ala Val Ala Asp Ala Gln Ala Thr Leu
465                 470                 475                 480

Ala Gln Leu Pro Pro Gly Ile Leu Ser Asp Ile Leu Ser Ala Leu Ala
                485                 490                 495

Ala Asn Ala Asp Pro Leu Thr Ser Gly Leu Leu Gly Ile Ala Ser Thr
                500                 505                 510

Leu Asn Pro Gln Val Gly Ser Ala Gln Pro Ile Val Ile Pro Thr Pro
            515                 520                 525

Ile Gly Glu Leu Asp Val Ile Ala Leu Tyr Ile Ala Ser Ile Ala Thr
    530                 535                 540

Gly Ser Ile Ala Leu Ala Ile Thr Asn Thr Ala Arg Pro Trp His Ile
545                 550                 555                 560

Gly Leu Tyr Gly Asn Ala Gly Gly Leu Gly Pro Thr Gln Gly His Pro
                565                 570                 575

Leu Ser Ser Ala Thr Asp Glu Pro Glu Pro His Trp Gly Pro Phe Gly
            580                 585                 590

Gly Ala Ala Pro Val Ser Ala Gly Val Gly His Ala Ala Leu Val Gly
        595                 600                 605

Ala Leu Ser Val Pro His Ser Trp Thr Thr Ala Ala Pro Glu Ile Gln
    610                 615                 620
```

```
Leu Ala Val Gln Ala Thr Pro Thr Phe Ser Ser Ser Ala Gly Ala Asp
625                 630                 635                 640

Pro Thr Ala Leu Asn Gly Met Pro Ala Gly Leu Leu Ser Gly Met Ala
            645                 650                 655

Leu Ala Ser Leu Ala Ala Arg Gly Thr Thr Gly Gly Gly Thr Arg
            660                 665                 670

Ser Gly Thr Ser Thr Asp Gly Gln Glu Asp Gly Arg Lys Pro Pro Val
        675                 680                 685

Val Val Ile Arg Glu Gln Pro Pro Pro Gly Asn Pro Pro Arg
    690                 695                 700

<210> SEQ ID NO 27
<211> LENGTH: 920
<212> TYPE: PRT
<213> ORGANISM: Artificial Sequence
<220> FEATURE:
<223> OTHER INFORMATION: M72-Mtb9.9-Mtb9.8

<400> SEQUENCE: 27

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
        115                 120                 125

Glu Gly Pro Pro Ala Glu Phe Met Val Asp Phe Gly Ala Leu Pro Pro
    130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
        195                 200                 205

Val Ala Trp Met Ser Val Thr Ala Gly Gln Ala Glu Leu Thr Ala Ala
    210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
        275                 280                 285
```

```
        -continued

Gly Tyr Ala Ala Ala Thr Ala Thr Ala Thr Leu Leu Pro Phe
    290             295             300

Glu Glu Ala Pro Glu Met Thr Ser Ala Gly Gly Leu Leu Glu Gln Ala
305             310             315             320

Ala Ala Val Glu Glu Ala Ser Asp Thr Ala Ala Asn Gln Leu Met
            325             330             335

Asn Asn Val Pro Gln Ala Leu Gln Gln Leu Ala Gln Pro Thr Gln Gly
            340             345             350

Thr Thr Pro Ser Ser Lys Leu Gly Gly Leu Trp Lys Thr Val Ser Pro
            355             360             365

His Arg Ser Pro Ile Ser Asn Met Val Ser Met Ala Asn Asn His Met
370             375             380

Ser Met Thr Asn Ser Gly Val Ser Met Thr Asn Thr Leu Ser Ser Met
385             390             395             400

Leu Lys Gly Phe Ala Pro Ala Ala Ala Gln Ala Val Gln Thr Ala
            405             410             415

Ala Gln Asn Gly Val Arg Ala Met Ser Ser Leu Gly Ser Ser Leu Gly
            420             425             430

Ser Ser Gly Leu Gly Gly Val Ala Ala Asn Leu Gly Arg Ala Ala
            435             440             445

Ser Val Gly Ser Leu Ser Val Pro Gln Ala Trp Ala Ala Asn Gln
            450             455             460

Ala Val Thr Pro Ala Ala Arg Ala Leu Pro Leu Thr Ser Leu Thr Ser
465             470             475             480

Ala Ala Glu Arg Gly Pro Gly Gln Met Leu Gly Gly Leu Pro Val Gly
            485             490             495

Gln Met Gly Ala Arg Ala Gly Gly Leu Ser Gly Val Leu Arg Val
            500             505             510

Pro Pro Arg Pro Tyr Val Met Pro His Ser Pro Ala Ala Gly Asp Ile
            515             520             525

Ala Pro Pro Ala Leu Ser Gln Asp Arg Phe Ala Asp Phe Pro Ala Leu
            530             535             540

Pro Leu Asp Pro Ser Ala Met Val Ala Gln Val Gly Pro Gln Val Val
545             550             555             560

Asn Ile Asn Thr Lys Leu Gly Tyr Asn Asn Ala Val Gly Ala Gly Thr
            565             570             575

Gly Ile Val Ile Asp Pro Asn Gly Val Val Leu Thr Asn Asn His Val
            580             585             590

Ile Ala Gly Ala Thr Asp Ile Asn Ala Phe Ser Val Gly Ser Gly Gln
            595             600             605

Thr Tyr Gly Val Asp Val Val Gly Tyr Asp Arg Thr Gln Asp Val Ala
610             615             620

Val Leu Gln Leu Arg Gly Ala Gly Gly Leu Pro Ser Ala Ala Ile Gly
625             630             635             640

Gly Gly Val Ala Val Gly Glu Pro Val Val Ala Met Gly Asn Ser Gly
            645             650             655

Gly Gln Gly Gly Thr Pro Arg Ala Val Pro Gly Arg Val Val Ala Leu
            660             665             670

Gly Gln Thr Val Gln Ala Ser Asp Ser Leu Thr Gly Ala Glu Glu Thr
            675             680             685

Leu Asn Gly Leu Ile Gln Phe Asp Ala Ala Ile Gln Pro Gly Asp Ala
690             695             700

Gly Gly Pro Val Val Asn Gly Leu Gly Gln Val Val Gly Met Asn Thr
```

```
            705                 710                 715                 720
Ala Ala Ser Ser Thr Met Thr Ile Asn Tyr Gln Phe Gly Asp Val Asp
                    725                 730                 735

Ala His Gly Ala Met Ile Arg Ala Gln Ala Ala Ser Leu Glu Ala Glu
                    740                 745                 750

His Gln Ala Ile Val Arg Asp Val Leu Ala Ala Gly Asp Phe Trp Gly
                    755                 760                 765

Gly Ala Gly Ser Val Ala Cys Gln Glu Phe Ile Thr Gln Leu Gly Arg
                    770                 775                 780

Asn Phe Gln Val Ile Tyr Glu Gln Ala Asn Ala His Gly Gln Lys Val
785                 790                 795                 800

Gln Ala Ala Gly Asn Asn Met Ala Gln Thr Asp Ser Ala Val Gly Ser
                    805                 810                 815

Ser Trp Ala Thr Ser Met Ser Leu Leu Asp Ala His Ile Pro Gln Leu
                    820                 825                 830

Val Ala Ser Gln Ser Ala Phe Ala Ala Lys Ala Gly Leu Met Arg His
                    835                 840                 845

Thr Ile Gly Gln Ala Glu Gln Ala Ala Met Ser Ala Gln Ala Phe His
                    850                 855                 860

Gln Gly Glu Ser Ser Ala Ala Phe Gln Ala Ala His Ala Arg Phe Val
865                 870                 875                 880

Ala Ala Ala Ala Lys Val Asn Thr Leu Leu Asp Val Ala Gln Ala Asn
                    885                 890                 895

Leu Gly Glu Ala Ala Gly Thr Tyr Val Ala Asp Ala Ala Ala Ala
                    900                 905                 910

Ser Thr Tyr Thr Gly Phe Pro Trp
                    915                 920

<210> SEQ ID NO 28
<211> LENGTH: 1010
<212> TYPE: PRT
<213> ORGANISM: Artificial Sequence
<220> FEATURE:
<223> OTHER INFORMATION: M103

<400> SEQUENCE: 28

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
                20                  25                  30

Ser Gly Gly Ser Pro Thr Val His Ile Gly Pro Thr Ala Phe Leu
            35                  40                  45

Gly Leu Gly Val Val Asp Asn Asn Gly Asn Gly Ala Arg Val Gln Arg
        50                  55                  60

Val Val Gly Ser Ala Pro Ala Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
                100                 105                 110

Trp Gln Thr Lys Ser Gly Gly Thr Arg Thr Gly Asn Val Thr Leu Ala
            115                 120                 125

Glu Gly Pro Pro Ala Glu Phe Met Val Asp Phe Gly Ala Leu Pro Pro
        130                 135                 140

Glu Ile Asn Ser Ala Arg Met Tyr Ala Gly Pro Gly Ser Ala Ser Leu
```

-continued

```
            145                 150                 155                 160
        Val Ala Ala Ala Gln Met Trp Asp Ser Val Ala Ser Asp Leu Phe Ser
                        165                 170                 175
        Ala Ala Ser Ala Phe Gln Ser Val Val Trp Gly Leu Thr Val Gly Ser
                        180                 185                 190
        Trp Ile Gly Ser Ser Ala Gly Leu Met Val Ala Ala Ser Pro Tyr
                        195                 200                 205
        Val Ala Trp Met Ser Val Thr Ala Gly Gln Ala Glu Leu Thr Ala Ala
                    210                 215                 220
        Gln Val Arg Val Ala Ala Ala Tyr Glu Thr Ala Tyr Gly Leu Thr
        225                 230                 235                 240
        Val Pro Pro Pro Val Ile Ala Glu Asn Arg Ala Glu Leu Met Ile Leu
                            245                 250                 255
        Ile Ala Thr Asn Leu Leu Gly Gln Asn Thr Pro Ala Ile Ala Val Asn
                        260                 265                 270
        Glu Ala Glu Tyr Gly Glu Met Trp Ala Gln Asp Ala Ala Ala Met Phe
                    275                 280                 285
        Gly Tyr Ala Ala Ala Thr Ala Thr Ala Thr Ala Thr Leu Leu Pro Phe
                290                 295                 300
        Glu Glu Ala Pro Glu Met Thr Ser Ala Gly Gly Leu Leu Glu Gln Ala
        305                 310                 315                 320
        Ala Ala Val Glu Glu Ala Ser Asp Thr Ala Ala Asn Gln Leu Met
                        325                 330                 335
        Asn Asn Val Pro Gln Ala Leu Gln Gln Leu Ala Gln Pro Thr Gln Gly
                        340                 345                 350
        Thr Thr Pro Ser Ser Lys Leu Gly Gly Leu Trp Lys Thr Val Ser Pro
                    355                 360                 365
        His Arg Ser Pro Ile Ser Asn Met Val Ser Met Ala Asn Asn His Met
                    370                 375                 380
        Ser Met Thr Asn Ser Gly Val Ser Met Thr Asn Thr Leu Ser Ser Met
        385                 390                 395                 400
        Leu Lys Gly Phe Ala Pro Ala Ala Ala Gln Ala Val Gln Thr Ala
                        405                 410                 415
        Ala Gln Asn Gly Val Arg Ala Met Ser Ser Leu Gly Ser Ser Leu Gly
                    420                 425                 430
        Ser Ser Gly Leu Gly Gly Val Ala Ala Asn Leu Gly Arg Ala Ala
                    435                 440                 445
        Ser Val Gly Ser Leu Ser Val Pro Gln Ala Trp Ala Ala Ala Asn Gln
                450                 455                 460
        Ala Val Thr Pro Ala Ala Arg Ala Leu Pro Leu Thr Ser Leu Thr Ser
        465                 470                 475                 480
        Ala Ala Glu Arg Gly Pro Gly Gln Met Leu Gly Gly Leu Pro Val Gly
                        485                 490                 495
        Gln Met Gly Ala Arg Ala Gly Gly Leu Ser Gly Val Leu Arg Val
                        500                 505                 510
        Pro Pro Arg Pro Tyr Val Met Pro His Ser Pro Ala Ala Gly Asp Ile
                    515                 520                 525
        Ala Pro Pro Ala Leu Ser Gln Asp Arg Phe Ala Asp Phe Pro Ala Leu
                    530                 535                 540
        Pro Leu Asp Pro Ser Ala Met Val Ala Gln Val Gly Pro Gln Val Val
        545                 550                 555                 560
        Asn Ile Asn Thr Lys Leu Gly Tyr Asn Asn Ala Val Gly Ala Gly Thr
                        565                 570                 575
```

```
Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
            595                 600                 605

Thr Tyr Gly Val Asp Val Gly Tyr Asp Arg Thr Gln Asp Val Ala
    610                 615                 620

Val Leu Gln Leu Arg Gly Ala Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
            675                 680                 685

Leu Asn Gly Leu Ile Gln Phe Asp Ala Ala Ile Gln Pro Gly Asp Ala
        690                 695                 700

Gly Gly Pro Val Val Asn Gly Leu Gly Gln Val Val Gly Met Asn Thr
705                 710                 715                 720

Ala Ala Ser Ser Gly Phe Ser Arg Pro Gly Leu Pro Val Glu Tyr Leu
                725                 730                 735

Gln Val Pro Ser Pro Ser Met Gly Arg Asp Ile Lys Val Gln Phe Gln
            740                 745                 750

Ser Gly Gly Asn Asn Ser Pro Ala Val Tyr Leu Leu Asp Gly Leu Arg
        755                 760                 765

Ala Gln Asp Asp Tyr Asn Gly Trp Asp Ile Asn Thr Pro Ala Phe Glu
        770                 775                 780

Trp Tyr Tyr Gln Ser Gly Leu Ser Ile Val Met Pro Val Gly Gly Gln
785                 790                 795                 800

Ser Ser Phe Tyr Ser Asp Trp Tyr Ser Pro Ala Cys Gly Lys Ala Gly
            805                 810                 815

Cys Gln Thr Tyr Lys Trp Glu Thr Phe Leu Thr Ser Glu Leu Pro Gln
            820                 825                 830

Trp Leu Ser Ala Asn Arg Ala Val Lys Pro Thr Gly Ser Ala Ala Ile
            835                 840                 845

Gly Leu Ser Met Ala Gly Ser Ser Ala Met Ile Leu Ala Ala Tyr His
            850                 855                 860

Pro Gln Gln Phe Ile Tyr Ala Gly Ser Leu Ser Ala Leu Leu Asp Pro
865                 870                 875                 880

Ser Gln Gly Met Gly Pro Ser Leu Ile Gly Leu Ala Met Gly Asp Ala
                885                 890                 895

Gly Gly Tyr Lys Ala Ala Asp Met Trp Gly Pro Ser Ser Asp Pro Ala
            900                 905                 910

Trp Glu Arg Asn Asp Pro Thr Gln Gln Ile Pro Lys Leu Val Ala Asn
            915                 920                 925

Asn Thr Arg Leu Trp Val Tyr Cys Gly Asn Gly Thr Pro Asn Glu Leu
        930                 935                 940

Gly Gly Ala Asn Ile Pro Ala Glu Phe Leu Glu Asn Phe Val Arg Ser
945                 950                 955                 960

Ser Asn Leu Lys Phe Gln Asp Ala Tyr Asn Ala Ala Gly Gly His Asn
                965                 970                 975

Ala Val Phe Asn Phe Pro Pro Asn Gly Thr His Ser Trp Glu Tyr Trp
            980                 985                 990
```

-continued

```
Gly Ala Gln Leu Asn Ala Met Lys Gly Asp Leu Gln Ser  Ser Leu Gly
        995                1000                1005
Ala Gly
    1010

<210> SEQ ID NO 29
<211> LENGTH: 1148
<212> TYPE: PRT
<213> ORGANISM: Artificial Sequence
<220> FEATURE:
<223> OTHER INFORMATION: M114

<400> SEQUENCE: 29

Met Thr Ala Ala Ser Asp Asn Phe Gln Leu Ser Gln Gly Gly Gln Gly
1               5                   10                  15

Phe Ala Ile Pro Ile Gly Gln Ala Met Ala Ile Ala Gly Gln Ile Arg
            20                  25                  30

Ser Gly Gly Gly Ser Pro Thr Val His Ile Gly Pro Thr Ala Phe Leu
        35                  40                  45

Gly Leu Gly Val Val Asp Asn Asn Gly Asn Gly Ala Arg Val Gln Arg
    50                  55                  60

Val Val Gly Ser Ala Pro Ala Ser Leu Gly Ile Ser Thr Gly Asp
65                  70                  75                  80

Val Ile Thr Ala Val Asp Gly Ala Pro Ile Asn Ser Ala Thr Ala Met
                85                  90                  95

Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
            115                 120                 125

Glu Gly Pro Pro Ala Glu Phe Met Val Asp Phe Gly Ala Leu Pro Pro
        130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
            195                 200                 205

Val Ala Trp Met Ser Val Thr Ala Gly Gln Ala Glu Leu Thr Ala Ala
        210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
                245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
        275                 280                 285

Gly Tyr Ala Ala Ala Thr Ala Thr Ala Thr Leu Leu Pro Phe
    290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Asn Gln Leu Met
                325                 330                 335
```

```
Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
        355                 360                 365

His Arg Ser Pro Ile Ser Asn Met Val Ser Met Ala Asn Asn His Met
370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Val Ala Ala Asn Leu Gly Arg Ala Ala
            435                 440                 445

Ser Val Gly Ser Leu Ser Val Pro Gln Ala Trp Ala Ala Ala Asn Gln
        450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
            485                 490                 495

Gln Met Gly Ala Arg Ala Gly Gly Leu Ser Gly Val Leu Arg Val
            500                 505                 510

Pro Pro Arg Pro Tyr Val Met Pro His Ser Pro Ala Ala Gly Asp Ile
        515                 520                 525

Ala Pro Pro Ala Leu Ser Gln Asp Arg Phe Ala Asp Phe Pro Ala Leu
        530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
            565                 570                 575

Gly Ile Val Ile Asp Pro Asn Gly Val Val Leu Thr Asn Asn His Val
            580                 585                 590

Ile Ala Gly Ala Thr Asp Ile Asn Ala Phe Ser Val Gly Ser Gly Gln
        595                 600                 605

Thr Tyr Gly Val Asp Val Val Gly Tyr Asp Arg Thr Gln Asp Val Ala
        610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
            645                 650                 655

Gly Gln Gly Gly Thr Pro Arg Ala Val Pro Gly Arg Val Val Ala Leu
            660                 665                 670

Gly Gln Thr Val Gln Ala Ser Asp Ser Leu Thr Gly Ala Glu Glu Thr
            675                 680                 685

Leu Asn Gly Leu Ile Gln Phe Asp Ala Ala Ile Gln Pro Gly Asp Ala
        690                 695                 700

Gly Gly Pro Val Val Asn Gly Leu Gly Gln Val Val Gly Met Asn Thr
705                 710                 715                 720

Ala Ala Ser Ser Thr Met Asp Phe Gly Leu Pro Pro Glu Val Asn
                725                 730                 735

Ser Ser Arg Met Tyr Ser Gly Pro Gly Pro Glu Ser Met Leu Ala Ala
            740                 745                 750

Ala Ala Ala Trp Asp Gly Val Ala Ala Glu Leu Thr Ser Ala Ala Val
```

```
                755                 760                 765
Ser Tyr Gly Ser Val Val Ser Thr Leu Ile Val Glu Pro Trp Met Gly
    770                 775                 780

Pro Ala Ala Ala Ala Met Ala Ala Ala Thr Pro Tyr Val Gly Trp
785                 790                 795                 800

Leu Ala Ala Thr Ala Ala Leu Ala Lys Glu Thr Ala Thr Gln Ala Arg
                805                 810                 815

Ala Ala Ala Glu Ala Phe Gly Thr Ala Phe Ala Met Thr Val Pro Pro
            820                 825                 830

Ser Leu Val Ala Ala Asn Arg Ser Arg Leu Met Ser Leu Val Ala Ala
                835                 840                 845

Asn Ile Leu Gly Gln Asn Ser Ala Ala Ile Ala Ala Thr Gln Ala Glu
850                 855                 860

Tyr Ala Glu Met Trp Ala Gln Asp Ala Ala Val Met Tyr Ser Tyr Glu
865                 870                 875                 880

Gly Ala Ser Ala Ala Ser Ala Leu Pro Pro Phe Thr Pro Pro Val
                885                 890                 895

Gln Gly Thr Gly Pro Ala Gly Pro Ala Ala Ala Ala Ala Thr Gln
                    900                 905                 910

Ala Ala Gly Ala Gly Ala Val Ala Asp Ala Gln Ala Thr Leu Ala Gln
                915                 920                 925

Leu Pro Pro Gly Ile Leu Ser Asp Ile Leu Ser Ala Leu Ala Ala Asn
930                 935                 940

Ala Asp Pro Leu Thr Ser Gly Leu Leu Gly Ile Ala Ser Thr Leu Asn
945                 950                 955                 960

Pro Gln Val Gly Ser Ala Gln Pro Ile Val Ile Pro Thr Pro Ile Gly
                965                 970                 975

Glu Leu Asp Val Ile Ala Leu Tyr Ile Ala Ser Ile Ala Thr Gly Ser
                980                 985                 990

Ile Ala Leu Ala Ile Thr Asn Thr Ala Arg Pro Trp His Ile Gly Leu
                995                 1000                1005

Tyr Gly Asn Ala Gly Gly Leu  Gly Pro Thr Gln Gly  His Pro Leu
    1010                1015                1020

Ser Ser  Ala Thr Asp Glu Pro  Glu Pro His Trp Gly  Pro Phe Gly
    1025                1030                1035

Gly Ala  Ala Pro Val Ser Ala  Gly Val Gly His Ala  Ala Leu Val
    1040                1045                1050

Gly Ala  Leu Ser Val Pro His  Ser Trp Thr Thr Ala  Ala Pro Glu
    1055                1060                1065

Ile Gln  Leu Ala Val Gln Ala  Thr Pro Thr Phe Ser  Ser Ser Ala
    1070                1075                1080

Gly Ala  Asp Pro Thr Ala Leu  Asn Gly Met Pro Ala  Gly Leu Leu
    1085                1090                1095

Ser Gly  Met Ala Leu Ala Ser  Leu Ala Ala Arg Gly  Thr Thr Gly
    1100                1105                1110

Gly Gly  Gly Thr Arg Ser Gly  Thr Ser Thr Asp Gly  Gln Glu Asp
    1115                1120                1125

Gly Arg  Lys Pro Pro Val Val  Val Ile Arg Glu Gln  Pro Pro Pro
    1130                1135                1140

Gly Asn  Pro Pro Arg
    1145

<210> SEQ ID NO 30
```

```
<211> LENGTH: 9
<212> TYPE: PRT
<213> ORGANISM: Mycobacterium tuberculosis

<400> SEQUENCE: 30

Trp Val Leu Ala Ala Gly Val Gln Ala
1               5

<210> SEQ ID NO 31
<211> LENGTH: 9
<212> TYPE: PRT
<213> ORGANISM: Mycobacterium tuberculosis

<400> SEQUENCE: 31

Val Leu Ala Ala Gly Val Gln Ala Met
1               5

<210> SEQ ID NO 32
<211> LENGTH: 9
<212> TYPE: PRT
<213> ORGANISM: Mycobacterium tuberculosis

<400> SEQUENCE: 32

Val Ile Arg Asp Gly Val Thr Arg Arg
1               5

<210> SEQ ID NO 33
<211> LENGTH: 9
<212> TYPE: PRT
<213> ORGANISM: Mycobacterium tuberculosis

<400> SEQUENCE: 33

Leu Ala Pro His Thr Pro Leu Ala Arg
1               5

<210> SEQ ID NO 34
<211> LENGTH: 9
<212> TYPE: PRT
<213> ORGANISM: Mycobacterium tuberculosis

<400> SEQUENCE: 34

Ile Arg Leu Phe Asp Ala Gly Ile Arg
1               5

<210> SEQ ID NO 35
<211> LENGTH: 9
<212> TYPE: PRT
<213> ORGANISM: Mycobacterium tuberculosis

<400> SEQUENCE: 35

Ile Arg His Arg Glu Ala Ile Asp Arg
1               5

<210> SEQ ID NO 36
<211> LENGTH: 9
<212> TYPE: PRT
<213> ORGANISM: Mycobacterium tuberculosis

<400> SEQUENCE: 36

Leu Leu Ala Thr Gly Val Arg Glu Val
1               5

<210> SEQ ID NO 37
<211> LENGTH: 9
<212> TYPE: PRT
```

```
<213> ORGANISM: Mycobacterium tuberculosis

<400> SEQUENCE: 37

Phe Arg Arg Arg Val Ala Val Ala Val
1               5

<210> SEQ ID NO 38
<211> LENGTH: 9
<212> TYPE: PRT
<213> ORGANISM: Mycobacterium tuberculosis

<400> SEQUENCE: 38

Phe Ala Ile Asp Phe Pro Leu Thr Tyr
1               5

<210> SEQ ID NO 39
<211> LENGTH: 9
<212> TYPE: PRT
<213> ORGANISM: Mycobacterium tuberculosis

<400> SEQUENCE: 39

Phe Pro Leu Thr Tyr Arg Leu Gly Arg
1               5

<210> SEQ ID NO 40
<211> LENGTH: 9
<212> TYPE: PRT
<213> ORGANISM: Mycobacterium tuberculosis

<400> SEQUENCE: 40

Tyr Arg Leu Gly Arg Arg His Asn Thr
1               5

<210> SEQ ID NO 41
<211> LENGTH: 9
<212> TYPE: PRT
<213> ORGANISM: Mycobacterium tuberculosis

<400> SEQUENCE: 41

Val Arg Ser Phe Leu Leu Gln Leu Gly
1               5

<210> SEQ ID NO 42
<211> LENGTH: 9
<212> TYPE: PRT
<213> ORGANISM: Mycobacterium tuberculosis

<400> SEQUENCE: 42

Leu Leu Gln Leu Gly Gly Ile Arg Ala
1               5

<210> SEQ ID NO 43
<211> LENGTH: 9
<212> TYPE: PRT
<213> ORGANISM: Mycobacterium tuberculosis

<400> SEQUENCE: 43

Leu Val Thr Ala Val Arg Ala Asp Gly
1               5

<210> SEQ ID NO 44
<211> LENGTH: 9
<212> TYPE: PRT
<213> ORGANISM: Mycobacterium tuberculosis
```

```
<400> SEQUENCE: 44

Val Arg Ala Asp Gly Val Val Ile Thr
1               5

<210> SEQ ID NO 45
<211> LENGTH: 9
<212> TYPE: PRT
<213> ORGANISM: Mycobacterium tuberculosis

<400> SEQUENCE: 45

Val Val Ile Thr Glu Pro Leu Ala Gly
1               5

<210> SEQ ID NO 46
<211> LENGTH: 9
<212> TYPE: PRT
<213> ORGANISM: Mycobacterium tuberculosis

<400> SEQUENCE: 46

Ile Val Glu His Ala Ile Ser Val Arg
1               5

<210> SEQ ID NO 47
<211> LENGTH: 9
<212> TYPE: PRT
<213> ORGANISM: Mycobacterium tuberculosis

<400> SEQUENCE: 47

Ile Asp Phe Met Thr Val Arg Glu Arg
1               5

<210> SEQ ID NO 48
<211> LENGTH: 9
<212> TYPE: PRT
<213> ORGANISM: Mycobacterium tuberculosis

<400> SEQUENCE: 48

Phe Arg Leu Asp Glu Cys Pro Arg Gly
1               5

<210> SEQ ID NO 49
<211> LENGTH: 9
<212> TYPE: PRT
<213> ORGANISM: Mycobacterium tuberculosis

<400> SEQUENCE: 49

Leu Tyr Ser Gly Ala Val Val Met Leu
1               5

<210> SEQ ID NO 50
<211> LENGTH: 9
<212> TYPE: PRT
<213> ORGANISM: Mycobacterium tuberculosis

<400> SEQUENCE: 50

Tyr Ser Gly Ala Val Val Met Leu Ser
1               5

<210> SEQ ID NO 51
<211> LENGTH: 9
<212> TYPE: PRT
<213> ORGANISM: Mycobacterium tuberculosis

<400> SEQUENCE: 51
```

```
Val Val Met Leu Ser Ala Asp Gly Gly
1               5

<210> SEQ ID NO 52
<211> LENGTH: 9
<212> TYPE: PRT
<213> ORGANISM: Mycobacterium tuberculosis

<400> SEQUENCE: 52

Trp Leu Arg Ala Gly Ala Gly Ile Ile
1               5

<210> SEQ ID NO 53
<211> LENGTH: 9
<212> TYPE: PRT
<213> ORGANISM: Mycobacterium tuberculosis

<400> SEQUENCE: 53

Glu Leu Ser Val Ala Thr Gly Ala Val
1               5

<210> SEQ ID NO 54
<211> LENGTH: 9
<212> TYPE: PRT
<213> ORGANISM: Mycobacterium tuberculosis

<400> SEQUENCE: 54

Ser Val Ala Thr Gly Ala Val Ser Thr
1               5

<210> SEQ ID NO 55
<211> LENGTH: 9
<212> TYPE: PRT
<213> ORGANISM: Mycobacterium tuberculosis

<400> SEQUENCE: 55

Ile Pro Met Pro Ala Gly Val Asn Pro
1               5

<210> SEQ ID NO 56
<211> LENGTH: 9
<212> TYPE: PRT
<213> ORGANISM: Mycobacterium tuberculosis

<400> SEQUENCE: 56

Pro Met Pro Ala Gly Val Asn Pro Ala
1               5

<210> SEQ ID NO 57
<211> LENGTH: 9
<212> TYPE: PRT
<213> ORGANISM: Mycobacterium tuberculosis

<400> SEQUENCE: 57

Pro Ala Gly Val Asn Pro Ala Asp Leu
1               5

<210> SEQ ID NO 58
<211> LENGTH: 9
<212> TYPE: PRT
<213> ORGANISM: Mycobacterium tuberculosis

<400> SEQUENCE: 58

Gly Val Asn Pro Ala Asp Leu Ala Ala
1               5
```

<210> SEQ ID NO 59
<211> LENGTH: 9
<212> TYPE: PRT
<213> ORGANISM: Mycobacterium tuberculosis

<400> SEQUENCE: 59

Asn Pro Ala Asp Leu Ala Ala Glu Leu
1               5

<210> SEQ ID NO 60
<211> LENGTH: 9
<212> TYPE: PRT
<213> ORGANISM: Mycobacterium tuberculosis

<400> SEQUENCE: 60

Asp Leu Ala Ala Glu Leu Ala Ala Val
1               5

<210> SEQ ID NO 61
<211> LENGTH: 9
<212> TYPE: PRT
<213> ORGANISM: Mycobacterium tuberculosis

<400> SEQUENCE: 61

Leu Ala Ala Val Val Thr Glu Ser Val
1               5

<210> SEQ ID NO 62
<211> LENGTH: 9
<212> TYPE: PRT
<213> ORGANISM: Mycobacterium tuberculosis

<400> SEQUENCE: 62

Val Thr Glu Ser Val Asp Glu Asp Tyr
1               5

<210> SEQ ID NO 63
<211> LENGTH: 9
<212> TYPE: PRT
<213> ORGANISM: Mycobacterium tuberculosis

<400> SEQUENCE: 63

Thr Glu Ser Val Asp Glu Asp Tyr Leu
1               5

<210> SEQ ID NO 64
<211> LENGTH: 9
<212> TYPE: PRT
<213> ORGANISM: Mycobacterium tuberculosis

<400> SEQUENCE: 64

Ser Val Asp Glu Asp Tyr Leu Leu Tyr
1               5

<210> SEQ ID NO 65
<211> LENGTH: 9
<212> TYPE: PRT
<213> ORGANISM: Mycobacterium tuberculosis

<400> SEQUENCE: 65

Tyr Glu Cys Asp Gly Gln Trp Val Leu
1               5

<210> SEQ ID NO 66
<211> LENGTH: 9
<212> TYPE: PRT
<213> ORGANISM: Mycobacterium tuberculosis

<400> SEQUENCE: 66

Gly Gln Trp Val Leu Ala Ala Gly Val
1               5

<210> SEQ ID NO 67
<211> LENGTH: 9
<212> TYPE: PRT
<213> ORGANISM: Mycobacterium tuberculosis

<400> SEQUENCE: 67

Val Leu Ala Ala Gly Val Gln Ala Met
1               5

<210> SEQ ID NO 68
<211> LENGTH: 9
<212> TYPE: PRT
<213> ORGANISM: Mycobacterium tuberculosis

<400> SEQUENCE: 68

Glu Leu Asp Ser Asp Glu Leu Arg Val
1               5

<210> SEQ ID NO 69
<211> LENGTH: 9
<212> TYPE: PRT
<213> ORGANISM: Mycobacterium tuberculosis

<400> SEQUENCE: 69

Asp Ser Asp Glu Leu Arg Val Ile Arg
1               5

<210> SEQ ID NO 70
<211> LENGTH: 9
<212> TYPE: PRT
<213> ORGANISM: Mycobacterium tuberculosis

<400> SEQUENCE: 70

Gln Gln Trp Ser Gly Arg Pro Gly Ala
1               5

<210> SEQ ID NO 71
<211> LENGTH: 9
<212> TYPE: PRT
<213> ORGANISM: Mycobacterium tuberculosis

<400> SEQUENCE: 71

Gly Arg Pro Gly Ala Ala Leu Gly Glu
1               5

<210> SEQ ID NO 72
<211> LENGTH: 9
<212> TYPE: PRT
<213> ORGANISM: Mycobacterium tuberculosis

<400> SEQUENCE: 72

Arg Pro Gly Ala Ala Leu Gly Glu Ala
1               5

<210> SEQ ID NO 73
<211> LENGTH: 9

```
<212> TYPE: PRT
<213> ORGANISM: Mycobacterium tuberculosis

<400> SEQUENCE: 73

Ala Leu Gly Glu Ala Val Asp Arg Leu
1               5

<210> SEQ ID NO 74
<211> LENGTH: 9
<212> TYPE: PRT
<213> ORGANISM: Mycobacterium tuberculosis

<400> SEQUENCE: 74

Gly Glu Ala Val Asp Arg Leu Leu Leu
1               5

<210> SEQ ID NO 75
<211> LENGTH: 9
<212> TYPE: PRT
<213> ORGANISM: Mycobacterium tuberculosis

<400> SEQUENCE: 75

Ala Phe Gly Trp Val Ala Phe Glu Phe
1               5

<210> SEQ ID NO 76
<211> LENGTH: 9
<212> TYPE: PRT
<213> ORGANISM: Mycobacterium tuberculosis

<400> SEQUENCE: 76

Arg Leu Ala Pro His Thr Pro Leu Ala
1               5

<210> SEQ ID NO 77
<211> LENGTH: 9
<212> TYPE: PRT
<213> ORGANISM: Mycobacterium tuberculosis

<400> SEQUENCE: 77

Leu Ala Pro His Thr Pro Leu Ala Arg
1               5

<210> SEQ ID NO 78
<211> LENGTH: 9
<212> TYPE: PRT
<213> ORGANISM: Mycobacterium tuberculosis

<400> SEQUENCE: 78

Ala Pro His Thr Pro Leu Ala Arg Val
1               5

<210> SEQ ID NO 79
<211> LENGTH: 9
<212> TYPE: PRT
<213> ORGANISM: Mycobacterium tuberculosis

<400> SEQUENCE: 79

Pro His Thr Pro Leu Ala Arg Val Phe
1               5

<210> SEQ ID NO 80
<211> LENGTH: 9
<212> TYPE: PRT
<213> ORGANISM: Mycobacterium tuberculosis
```

```
<400> SEQUENCE: 80

Pro Leu Ala Arg Val Phe Ser Pro Arg
1               5

<210> SEQ ID NO 81
<211> LENGTH: 9
<212> TYPE: PRT
<213> ORGANISM: Mycobacterium tuberculosis

<400> SEQUENCE: 81

Arg Val Phe Ser Pro Arg Thr Arg Ile
1               5

<210> SEQ ID NO 82
<211> LENGTH: 9
<212> TYPE: PRT
<213> ORGANISM: Mycobacterium tuberculosis

<400> SEQUENCE: 82

Val Phe Ser Pro Arg Thr Arg Ile Met
1               5

<210> SEQ ID NO 83
<211> LENGTH: 9
<212> TYPE: PRT
<213> ORGANISM: Mycobacterium tuberculosis

<400> SEQUENCE: 83

Val Ser Glu Lys Glu Ile Arg Leu Phe
1               5

<210> SEQ ID NO 84
<211> LENGTH: 9
<212> TYPE: PRT
<213> ORGANISM: Mycobacterium tuberculosis

<400> SEQUENCE: 84

Ala Gly Ile Arg His Arg Glu Ala Ile
1               5

<210> SEQ ID NO 85
<211> LENGTH: 9
<212> TYPE: PRT
<213> ORGANISM: Mycobacterium tuberculosis

<400> SEQUENCE: 85

Leu Leu Ala Thr Gly Val Arg Glu Val
1               5

<210> SEQ ID NO 86
<211> LENGTH: 9
<212> TYPE: PRT
<213> ORGANISM: Mycobacterium tuberculosis

<400> SEQUENCE: 86

Arg Glu Val Pro Gln Ser Arg Ser Val
1               5

<210> SEQ ID NO 87
<211> LENGTH: 9
<212> TYPE: PRT
<213> ORGANISM: Mycobacterium tuberculosis

<400> SEQUENCE: 87
```

Val Pro Gln Ser Arg Ser Val Asp Val
1               5

<210> SEQ ID NO 88
<211> LENGTH: 9
<212> TYPE: PRT
<213> ORGANISM: Mycobacterium tuberculosis

<400> SEQUENCE: 88

Val Ser Asp Asp Pro Ser Gly Phe Arg
1               5

<210> SEQ ID NO 89
<211> LENGTH: 9
<212> TYPE: PRT
<213> ORGANISM: Mycobacterium tuberculosis

<400> SEQUENCE: 89

Asp Pro Ser Gly Phe Arg Arg Arg Val
1               5

<210> SEQ ID NO 90
<211> LENGTH: 9
<212> TYPE: PRT
<213> ORGANISM: Mycobacterium tuberculosis

<400> SEQUENCE: 90

Ser Gly Phe Arg Arg Arg Val Ala Val
1               5

<210> SEQ ID NO 91
<211> LENGTH: 9
<212> TYPE: PRT
<213> ORGANISM: Mycobacterium tuberculosis

<400> SEQUENCE: 91

Gly Phe Arg Arg Arg Val Ala Val Ala
1               5

<210> SEQ ID NO 92
<211> LENGTH: 9
<212> TYPE: PRT
<213> ORGANISM: Mycobacterium tuberculosis

<400> SEQUENCE: 92

Phe Arg Arg Arg Val Ala Val Ala Val
1               5

<210> SEQ ID NO 93
<211> LENGTH: 9
<212> TYPE: PRT
<213> ORGANISM: Mycobacterium tuberculosis

<400> SEQUENCE: 93

Arg Val Ala Val Ala Val Asp Glu Ile
1               5

<210> SEQ ID NO 94
<211> LENGTH: 9
<212> TYPE: PRT
<213> ORGANISM: Mycobacterium tuberculosis

<400> SEQUENCE: 94

Ile Ala Ala Gly Arg Tyr His Lys Val

```
<210> SEQ ID NO 95
<211> LENGTH: 9
<212> TYPE: PRT
<213> ORGANISM: Mycobacterium tuberculosis

<400> SEQUENCE: 95

Ala Gly Arg Tyr His Lys Val Ile Leu
1               5

<210> SEQ ID NO 96
<211> LENGTH: 9
<212> TYPE: PRT
<213> ORGANISM: Mycobacterium tuberculosis

<400> SEQUENCE: 96

Arg Tyr His Lys Val Ile Leu Ser Arg
1               5

<210> SEQ ID NO 97
<211> LENGTH: 9
<212> TYPE: PRT
<213> ORGANISM: Mycobacterium tuberculosis

<400> SEQUENCE: 97

Val Ile Leu Ser Arg Cys Val Glu Val
1               5

<210> SEQ ID NO 98
<211> LENGTH: 9
<212> TYPE: PRT
<213> ORGANISM: Mycobacterium tuberculosis

<400> SEQUENCE: 98

Val Pro Phe Ala Ile Asp Phe Pro Leu
1               5

<210> SEQ ID NO 99
<211> LENGTH: 9
<212> TYPE: PRT
<213> ORGANISM: Mycobacterium tuberculosis

<400> SEQUENCE: 99

Phe Ala Ile Asp Phe Pro Leu Thr Tyr
1               5

<210> SEQ ID NO 100
<211> LENGTH: 9
<212> TYPE: PRT
<213> ORGANISM: Mycobacterium tuberculosis

<400> SEQUENCE: 100

Ile Asp Phe Pro Leu Thr Tyr Arg Leu
1               5

<210> SEQ ID NO 101
<211> LENGTH: 9
<212> TYPE: PRT
<213> ORGANISM: Mycobacterium tuberculosis

<400> SEQUENCE: 101

Leu Gly Arg Arg His Asn Thr Pro Val
1               5
```

```
<210> SEQ ID NO 102
<211> LENGTH: 9
<212> TYPE: PRT
<213> ORGANISM: Mycobacterium tuberculosis

<400> SEQUENCE: 102

Arg Arg His Asn Thr Pro Val Arg Ser
1               5

<210> SEQ ID NO 103
<211> LENGTH: 9
<212> TYPE: PRT
<213> ORGANISM: Mycobacterium tuberculosis

<400> SEQUENCE: 103

Asn Thr Pro Val Arg Ser Phe Leu Leu
1               5

<210> SEQ ID NO 104
<211> LENGTH: 9
<212> TYPE: PRT
<213> ORGANISM: Mycobacterium tuberculosis

<400> SEQUENCE: 104

Pro Val Arg Ser Phe Leu Leu Gln Leu
1               5

<210> SEQ ID NO 105
<211> LENGTH: 9
<212> TYPE: PRT
<213> ORGANISM: Mycobacterium tuberculosis

<400> SEQUENCE: 105

Arg Ala Leu Gly Tyr Ser Pro Glu Leu
1               5

<210> SEQ ID NO 106
<211> LENGTH: 9
<212> TYPE: PRT
<213> ORGANISM: Mycobacterium tuberculosis

<400> SEQUENCE: 106

Ala Leu Gly Tyr Ser Pro Glu Leu Val
1               5

<210> SEQ ID NO 107
<211> LENGTH: 9
<212> TYPE: PRT
<213> ORGANISM: Mycobacterium tuberculosis

<400> SEQUENCE: 107

Tyr Ser Pro Glu Leu Val Thr Ala Val
1               5

<210> SEQ ID NO 108
<211> LENGTH: 9
<212> TYPE: PRT
<213> ORGANISM: Mycobacterium tuberculosis

<400> SEQUENCE: 108

Ser Pro Glu Leu Val Thr Ala Val Arg
1               5

<210> SEQ ID NO 109
```

-continued

```
<211> LENGTH: 9
<212> TYPE: PRT
<213> ORGANISM: Mycobacterium tuberculosis

<400> SEQUENCE: 109

Ala Val Arg Ala Asp Gly Val Val Ile
1               5

<210> SEQ ID NO 110
<211> LENGTH: 9
<212> TYPE: PRT
<213> ORGANISM: Mycobacterium tuberculosis

<400> SEQUENCE: 110

Ile Thr Glu Pro Leu Ala Gly Thr Arg
1               5

<210> SEQ ID NO 111
<211> LENGTH: 9
<212> TYPE: PRT
<213> ORGANISM: Mycobacterium tuberculosis

<400> SEQUENCE: 111

Glu Pro Leu Ala Gly Thr Arg Ala Leu
1               5

<210> SEQ ID NO 112
<211> LENGTH: 9
<212> TYPE: PRT
<213> ORGANISM: Mycobacterium tuberculosis

<400> SEQUENCE: 112

Gly Thr Arg Ala Leu Gly Arg Gly Pro
1               5

<210> SEQ ID NO 113
<211> LENGTH: 9
<212> TYPE: PRT
<213> ORGANISM: Mycobacterium tuberculosis

<400> SEQUENCE: 113

Arg Ala Leu Gly Arg Gly Pro Ala Ile
1               5

<210> SEQ ID NO 114
<211> LENGTH: 9
<212> TYPE: PRT
<213> ORGANISM: Mycobacterium tuberculosis

<400> SEQUENCE: 114

Leu Glu Ser Asn Ser Lys Glu Ile Val
1               5

<210> SEQ ID NO 115
<211> LENGTH: 9
<212> TYPE: PRT
<213> ORGANISM: Mycobacterium tuberculosis

<400> SEQUENCE: 115

Glu Ile Val Glu His Ala Ile Ser Val
1               5

<210> SEQ ID NO 116
<211> LENGTH: 9
<212> TYPE: PRT
```

<213> ORGANISM: Mycobacterium tuberculosis

<400> SEQUENCE: 116

Ile Val Glu His Ala Ile Ser Val Arg
1               5

<210> SEQ ID NO 117
<211> LENGTH: 9
<212> TYPE: PRT
<213> ORGANISM: Mycobacterium tuberculosis

<400> SEQUENCE: 117

His Ala Ile Ser Val Arg Ser Ser Leu
1               5

<210> SEQ ID NO 118
<211> LENGTH: 9
<212> TYPE: PRT
<213> ORGANISM: Mycobacterium tuberculosis

<400> SEQUENCE: 118

Ser Val Arg Ser Ser Leu Glu Glu Ile
1               5

<210> SEQ ID NO 119
<211> LENGTH: 9
<212> TYPE: PRT
<213> ORGANISM: Mycobacterium tuberculosis

<400> SEQUENCE: 119

Ser Leu Glu Glu Ile Thr Asp Ile Ala
1               5

<210> SEQ ID NO 120
<211> LENGTH: 9
<212> TYPE: PRT
<213> ORGANISM: Mycobacterium tuberculosis

<400> SEQUENCE: 120

Asp Ile Ala Glu Pro Gly Ser Ala Ala
1               5

<210> SEQ ID NO 121
<211> LENGTH: 9
<212> TYPE: PRT
<213> ORGANISM: Mycobacterium tuberculosis

<400> SEQUENCE: 121

Ala Glu Pro Gly Ser Ala Ala Val Ile
1               5

<210> SEQ ID NO 122
<211> LENGTH: 9
<212> TYPE: PRT
<213> ORGANISM: Mycobacterium tuberculosis

<400> SEQUENCE: 122

Arg Glu Arg Gly Ser Val Gln His Leu
1               5

<210> SEQ ID NO 123
<211> LENGTH: 9
<212> TYPE: PRT
<213> ORGANISM: Mycobacterium tuberculosis

<400> SEQUENCE: 123

Ser Val Gln His Leu Gly Ser Thr Ile
1               5

<210> SEQ ID NO 124
<211> LENGTH: 9
<212> TYPE: PRT
<213> ORGANISM: Mycobacterium tuberculosis

<400> SEQUENCE: 124

Arg Leu Asp Pro Ser Ser Asp Arg Met
1               5

<210> SEQ ID NO 125
<211> LENGTH: 9
<212> TYPE: PRT
<213> ORGANISM: Mycobacterium tuberculosis

<400> SEQUENCE: 125

Asp Pro Ser Ser Asp Arg Met Ala Ala
1               5

<210> SEQ ID NO 126
<211> LENGTH: 9
<212> TYPE: PRT
<213> ORGANISM: Mycobacterium tuberculosis

<400> SEQUENCE: 126

Ser Ser Asp Arg Met Ala Ala Leu Glu
1               5

<210> SEQ ID NO 127
<211> LENGTH: 9
<212> TYPE: PRT
<213> ORGANISM: Mycobacterium tuberculosis

<400> SEQUENCE: 127

Asp Arg Met Ala Ala Leu Glu Ala Leu
1               5

<210> SEQ ID NO 128
<211> LENGTH: 9
<212> TYPE: PRT
<213> ORGANISM: Mycobacterium tuberculosis

<400> SEQUENCE: 128

Arg Met Ala Ala Leu Glu Ala Leu Phe
1               5

<210> SEQ ID NO 129
<211> LENGTH: 9
<212> TYPE: PRT
<213> ORGANISM: Mycobacterium tuberculosis

<400> SEQUENCE: 129

Ala Ala Leu Glu Ala Leu Phe Pro Ala
1               5

<210> SEQ ID NO 130
<211> LENGTH: 9
<212> TYPE: PRT
<213> ORGANISM: Mycobacterium tuberculosis

<400> SEQUENCE: 130

Ala Leu Glu Ala Leu Phe Pro Ala Val
1               5

<210> SEQ ID NO 131
<211> LENGTH: 9
<212> TYPE: PRT
<213> ORGANISM: Mycobacterium tuberculosis

<400> SEQUENCE: 131

Leu Glu Ala Leu Phe Pro Ala Val Thr
1               5

<210> SEQ ID NO 132
<211> LENGTH: 9
<212> TYPE: PRT
<213> ORGANISM: Mycobacterium tuberculosis

<400> SEQUENCE: 132

Phe Pro Ala Val Thr Ala Ser Gly Ile
1               5

<210> SEQ ID NO 133
<211> LENGTH: 9
<212> TYPE: PRT
<213> ORGANISM: Mycobacterium tuberculosis

<400> SEQUENCE: 133

Ala Val Thr Ala Ser Gly Ile Pro Lys
1               5

<210> SEQ ID NO 134
<211> LENGTH: 9
<212> TYPE: PRT
<213> ORGANISM: Mycobacterium tuberculosis

<400> SEQUENCE: 134

Val Thr Ala Ser Gly Ile Pro Lys Ala
1               5

<210> SEQ ID NO 135
<211> LENGTH: 9
<212> TYPE: PRT
<213> ORGANISM: Mycobacterium tuberculosis

<400> SEQUENCE: 135

Gly Ile Pro Lys Ala Ala Gly Val Glu
1               5

<210> SEQ ID NO 136
<211> LENGTH: 9
<212> TYPE: PRT
<213> ORGANISM: Mycobacterium tuberculosis

<400> SEQUENCE: 136

Ile Pro Lys Ala Ala Gly Val Glu Ala
1               5

<210> SEQ ID NO 137
<211> LENGTH: 9
<212> TYPE: PRT
<213> ORGANISM: Mycobacterium tuberculosis

<400> SEQUENCE: 137

Lys Ala Ala Gly Val Glu Ala Ile Phe
1               5

```
<210> SEQ ID NO 138
<211> LENGTH: 9
<212> TYPE: PRT
<213> ORGANISM: Mycobacterium tuberculosis

<400> SEQUENCE: 138

Ala Gly Val Glu Ala Ile Phe Arg Leu
1               5

<210> SEQ ID NO 139
<211> LENGTH: 9
<212> TYPE: PRT
<213> ORGANISM: Mycobacterium tuberculosis

<400> SEQUENCE: 139

Arg Leu Asp Glu Cys Pro Arg Gly Leu
1               5

<210> SEQ ID NO 140
<211> LENGTH: 9
<212> TYPE: PRT
<213> ORGANISM: Mycobacterium tuberculosis

<400> SEQUENCE: 140

Cys Pro Arg Gly Leu Tyr Ser Gly Ala
1               5

<210> SEQ ID NO 141
<211> LENGTH: 9
<212> TYPE: PRT
<213> ORGANISM: Mycobacterium tuberculosis

<400> SEQUENCE: 141

Gly Leu Tyr Ser Gly Ala Val Val Met
1               5

<210> SEQ ID NO 142
<211> LENGTH: 9
<212> TYPE: PRT
<213> ORGANISM: Mycobacterium tuberculosis

<400> SEQUENCE: 142

Leu Tyr Ser Gly Ala Val Val Met Leu
1               5

<210> SEQ ID NO 143
<211> LENGTH: 9
<212> TYPE: PRT
<213> ORGANISM: Mycobacterium tuberculosis

<400> SEQUENCE: 143

Val Met Leu Ser Ala Asp Gly Gly Leu
1               5

<210> SEQ ID NO 144
<211> LENGTH: 9
<212> TYPE: PRT
<213> ORGANISM: Mycobacterium tuberculosis

<400> SEQUENCE: 144

Gly Leu Asp Ala Ala Leu Thr Leu Arg
1               5
```

<210> SEQ ID NO 145
<211> LENGTH: 9
<212> TYPE: PRT
<213> ORGANISM: Mycobacterium tuberculosis

<400> SEQUENCE: 145

Leu Asp Ala Ala Leu Thr Leu Arg Ala
1               5

<210> SEQ ID NO 146
<211> LENGTH: 9
<212> TYPE: PRT
<213> ORGANISM: Mycobacterium tuberculosis

<400> SEQUENCE: 146

Ala Ala Leu Thr Leu Arg Ala Ala Tyr
1               5

<210> SEQ ID NO 147
<211> LENGTH: 9
<212> TYPE: PRT
<213> ORGANISM: Mycobacterium tuberculosis

<400> SEQUENCE: 147

Leu Thr Leu Arg Ala Ala Tyr Gln Val
1               5

<210> SEQ ID NO 148
<211> LENGTH: 9
<212> TYPE: PRT
<213> ORGANISM: Mycobacterium tuberculosis

<400> SEQUENCE: 148

Ala Tyr Gln Val Gly Gly Arg Thr Trp
1               5

<210> SEQ ID NO 149
<211> LENGTH: 9
<212> TYPE: PRT
<213> ORGANISM: Mycobacterium tuberculosis

<400> SEQUENCE: 149

Thr Trp Leu Arg Ala Gly Ala Gly Ile
1               5

<210> SEQ ID NO 150
<211> LENGTH: 9
<212> TYPE: PRT
<213> ORGANISM: Mycobacterium tuberculosis

<400> SEQUENCE: 150

Glu Glu Ser Glu Pro Glu Arg Glu Phe
1               5

<210> SEQ ID NO 151
<211> LENGTH: 9
<212> TYPE: PRT
<213> ORGANISM: Mycobacterium tuberculosis

<400> SEQUENCE: 151

Arg Glu Phe Glu Glu Thr Cys Glu Lys
1               5

<210> SEQ ID NO 152
<211> LENGTH: 9

```
<212> TYPE: PRT
<213> ORGANISM: Mycobacterium tuberculosis

<400> SEQUENCE: 152

Lys Leu Ser Thr Leu Thr Pro Tyr Leu
1               5

<210> SEQ ID NO 153
<211> LENGTH: 9
<212> TYPE: PRT
<213> ORGANISM: Mycobacterium tuberculosis

<400> SEQUENCE: 153

Ser Thr Leu Thr Pro Tyr Leu Val Ala
1               5

<210> SEQ ID NO 154
<211> LENGTH: 9
<212> TYPE: PRT
<213> ORGANISM: Mycobacterium tuberculosis

<400> SEQUENCE: 154

Thr Leu Thr Pro Tyr Leu Val Ala Arg
1               5

<210> SEQ ID NO 155
<211> LENGTH: 1053
<212> TYPE: PRT
<213> ORGANISM: Mycobacterium tuberculosis

<400> SEQUENCE: 155

Met Asn Phe Ser Val Leu Pro Pro Glu Ile Asn Ser Ala Leu Ile Phe
1               5                   10                  15

Ala Gly Ala Gly Pro Glu Pro Met Ala Ala Ala Ala Thr Ala Trp Asp
            20                  25                  30

Gly Leu Ala Met Glu Leu Ala Ser Ala Ala Ala Ser Phe Gly Ser Val
        35                  40                  45

Thr Ser Gly Leu Val Gly Gly Ala Trp Gln Gly Ala Ser Ser Ser Ala
    50                  55                  60

Met Ala Ala Ala Ala Ala Pro Tyr Ala Ala Trp Leu Ala Ala Ala Ala
65                  70                  75                  80

Val Gln Ala Glu Gln Thr Ala Ala Gln Ala Ala Ala Met Ile Ala Glu
                85                  90                  95

Phe Glu Ala Val Lys Thr Ala Val Val Gln Pro Met Leu Val Ala Ala
            100                 105                 110

Asn Arg Ala Asp Leu Val Ser Leu Val Met Ser Asn Leu Phe Gly Gln
        115                 120                 125

Asn Ala Pro Ala Ile Ala Ala Ile Glu Ala Thr Tyr Glu Gln Met Trp
    130                 135                 140

Ala Ala Asp Val Ser Ala Met Ser Ala Tyr His Ala Gly Ala Ser Ala
145                 150                 155                 160

Ile Ala Ser Ala Leu Ser Pro Phe Ser Lys Pro Leu Gln Asn Leu Ala
                165                 170                 175

Gly Leu Pro Ala Trp Leu Ala Ser Gly Ala Pro Ala Ala Ala Met Thr
            180                 185                 190

Ala Ala Ala Gly Ile Pro Ala Leu Ala Gly Gly Pro Thr Ala Ile Asn
        195                 200                 205

Leu Gly Ile Ala Asn Val Gly Gly Gly Asn Val Gly Asn Ala Asn Asn
    210                 215                 220
```

```
Gly Leu Ala Asn Ile Gly Asn Ala Asn Leu Gly Asn Tyr Asn Phe Gly
225                 230                 235                 240

Ser Gly Asn Phe Gly Asn Ser Asn Ile Gly Ser Ala Ser Leu Gly Asn
            245                 250                 255

Asn Asn Ile Gly Phe Gly Asn Leu Gly Ser Asn Val Gly Val Gly
        260                 265                 270

Asn Leu Gly Asn Leu Asn Thr Gly Phe Ala Asn Thr Gly Leu Gly Asn
            275                 280                 285

Phe Gly Phe Gly Asn Thr Gly Asn Asn Ile Gly Ile Gly Leu Thr
    290                 295                 300

Gly Asn Asn Gln Ile Gly Ile Gly Gly Leu Asn Ser Gly Thr Gly Asn
305                 310                 315                 320

Phe Gly Leu Phe Asn Ser Gly Ser Gly Asn Val Gly Phe Phe Asn Ser
            325                 330                 335

Gly Asn Gly Asn Phe Gly Ile Gly Asn Ser Gly Asn Phe Asn Thr Gly
            340                 345                 350

Gly Trp Asn Ser Gly His Gly Asn Thr Gly Phe Phe Asn Ala Gly Ser
            355                 360                 365

Phe Asn Thr Gly Met Leu Asp Val Gly Asn Ala Asn Thr Gly Ser Leu
    370                 375                 380

Asn Thr Gly Ser Tyr Asn Met Gly Asp Phe Asn Pro Gly Ser Ser Asn
385                 390                 395                 400

Thr Gly Thr Phe Asn Thr Gly Asn Ala Asn Thr Gly Phe Leu Asn Ala
            405                 410                 415

Gly Asn Ile Asn Thr Gly Val Phe Asn Ile Gly His Met Asn Asn Gly
            420                 425                 430

Leu Phe Asn Thr Gly Asp Met Asn Asn Gly Val Phe Tyr Arg Gly Val
            435                 440                 445

Gly Gln Gly Ser Leu Gln Phe Ser Ile Thr Thr Pro Asp Leu Thr Leu
450                 455                 460

Pro Pro Leu Gln Ile Pro Gly Ile Ser Val Pro Ala Phe Ser Leu Pro
465                 470                 475                 480

Ala Ile Thr Leu Pro Ser Leu Asn Ile Pro Ala Ala Thr Thr Pro Ala
            485                 490                 495

Asn Ile Thr Val Gly Ala Phe Ser Leu Pro Gly Leu Thr Leu Pro Ser
            500                 505                 510

Leu Asn Ile Pro Ala Ala Thr Thr Pro Ala Asn Ile Thr Val Gly Ala
    515                 520                 525

Phe Ser Leu Pro Gly Leu Thr Leu Pro Ser Leu Asn Ile Pro Ala Ala
530                 535                 540

Thr Thr Pro Ala Asn Ile Thr Val Gly Ala Phe Ser Leu Pro Gly Leu
545                 550                 555                 560

Thr Leu Pro Ser Leu Asn Ile Pro Ala Ala Thr Thr Pro Ala Asn Ile
            565                 570                 575

Thr Val Gly Ala Phe Ser Leu Pro Gly Leu Thr Leu Pro Ser Leu Asn
            580                 585                 590

Ile Pro Ala Ala Thr Thr Pro Ala Asn Ile Thr Val Gly Ala Phe Ser
    595                 600                 605

Leu Pro Gly Leu Thr Leu Pro Ser Leu Asn Ile Pro Ala Ala Thr Thr
    610                 615                 620

Pro Ala Asn Ile Thr Val Ser Gly Phe Gln Leu Pro Pro Leu Ser Ile
625                 630                 635                 640
```

```
Pro Ser Val Ala Ile Pro Val Thr Val Pro Ile Thr Val Gly
            645                 650                 655

Ala Phe Asn Leu Pro Pro Leu Gln Ile Pro Glu Val Thr Ile Pro Gln
            660                 665                 670

Leu Thr Ile Pro Ala Gly Ile Thr Ile Gly Gly Phe Ser Leu Pro Ala
            675                 680                 685

Ile His Thr Gln Pro Ile Thr Val Gly Gln Ile Gly Val Gly Gln Phe
            690                 695                 700

Gly Leu Pro Ser Ile Gly Trp Asp Val Phe Leu Ser Thr Pro Arg Ile
705                 710                 715                 720

Thr Val Pro Ala Phe Gly Ile Pro Phe Thr Leu Gln Phe Gln Thr Asn
            725                 730                 735

Val Pro Ala Leu Gln Pro Pro Gly Gly Gly Leu Ser Thr Phe Thr Asn
            740                 745                 750

Gly Ala Leu Ile Phe Gly Glu Phe Asp Leu Pro Gln Leu Val Val His
            755                 760                 765

Pro Tyr Thr Leu Thr Gly Pro Ile Val Ile Gly Ser Phe Phe Leu Pro
            770                 775                 780

Ala Phe Asn Ile Pro Gly Ile Asp Val Pro Ala Ile Asn Val Asp Gly
785                 790                 795                 800

Phe Thr Leu Pro Gln Ile Thr Thr Pro Ala Ile Thr Thr Pro Glu Phe
            805                 810                 815

Ala Ile Pro Pro Ile Gly Val Gly Gly Phe Thr Leu Pro Gln Ile Thr
            820                 825                 830

Thr Gln Glu Ile Ile Thr Pro Glu Leu Thr Ile Asn Ser Ile Gly Val
            835                 840                 845

Gly Gly Phe Thr Leu Pro Gln Ile Thr Thr Pro Pro Ile Thr Thr Pro
850                 855                 860

Pro Leu Thr Ile Asp Pro Ile Asn Leu Thr Gly Phe Thr Leu Pro Gln
865                 870                 875                 880

Ile Thr Thr Pro Pro Ile Thr Thr Pro Pro Leu Thr Ile Asp Pro Ile
            885                 890                 895

Asn Leu Thr Gly Phe Thr Leu Pro Gln Ile Thr Thr Pro Pro Ile Thr
            900                 905                 910

Thr Pro Pro Leu Thr Ile Glu Pro Ile Gly Val Gly Gly Phe Thr Thr
            915                 920                 925

Pro Pro Leu Thr Val Pro Gly Ile His Leu Pro Ser Thr Thr Ile Gly
            930                 935                 940

Ala Phe Ala Ile Pro Gly Gly Pro Gly Tyr Phe Asn Ser Ser Thr Ala
945                 950                 955                 960

Pro Ser Ser Gly Phe Phe Asn Ser Gly Ala Gly Gly Asn Ser Gly Phe
            965                 970                 975

Gly Asn Asn Gly Ser Gly Leu Ser Gly Trp Phe Asn Thr Asn Pro Ala
            980                 985                 990

Gly Leu Leu Gly Gly Ser Gly Tyr Gln Asn Phe Gly Gly Leu Ser Ser
            995                 1000                1005

Gly Phe Ser Asn Leu Gly Gly Val Ser Gly Phe Ala Asn Arg
            1010                1015                1020

Gly Ile Leu Pro Phe Ser Val Ala Ser Val Val Ser Gly Phe Ala
            1025                1030                1035

Asn Ile Gly Thr Asn Leu Ala Gly Phe Phe Gln Gly Thr Thr Ser
            1040                1045                1050
```

<210> SEQ ID NO 156
<211> LENGTH: 324
<212> TYPE: PRT
<213> ORGANISM: Mycobacterium tuberculosis

<400> SEQUENCE: 156

```
Met Ser Asp Gln Val Pro Lys Pro His Arg His Ile Trp Arg Ile
1               5                  10                  15
Thr Arg Arg Thr Leu Ser Lys Ser Trp Asp Asp Ser Ile Phe Ser Glu
                20                  25                  30
Ser Ala Gln Ala Ala Phe Trp Ser Ala Leu Ser Leu Pro Pro Leu Leu
                35                  40                  45
Leu Gly Met Leu Gly Ser Leu Ala Tyr Val Ala Pro Leu Phe Gly Pro
    50                  55                  60
Asp Thr Leu Pro Ala Ile Glu Lys Ser Ala Leu Ser Thr Ala His Ser
65                  70                  75                  80
Phe Phe Ser Pro Ser Val Val Asn Glu Ile Ile Glu Pro Thr Ile Gly
                85                  90                  95
Asp Ile Thr Asn Asn Ala Arg Gly Glu Val Ala Ser Leu Gly Phe Leu
                100                 105                 110
Ile Ser Leu Trp Ala Gly Ser Ser Ala Ile Ser Ala Phe Val Asp Ala
            115                 120                 125
Val Val Glu Ala His Asp Gln Thr Pro Leu Arg His Pro Val Arg Gln
130                 135                 140
Arg Phe Phe Ala Leu Phe Leu Tyr Val Val Met Leu Val Phe Leu Val
145                 150                 155                 160
Ala Thr Ala Pro Val Met Val Val Gly Pro Arg Lys Val Ser Glu His
                165                 170                 175
Ile Pro Glu Ser Leu Ala Asn Leu Leu Arg Tyr Gly Tyr Tyr Pro Ala
                180                 185                 190
Leu Ile Leu Gly Leu Thr Val Gly Val Ile Leu Leu Tyr Arg Val Ala
            195                 200                 205
Leu Pro Val Pro Leu Pro Thr His Arg Leu Val Leu Gly Ala Val Leu
210                 215                 220
Ala Ile Ala Val Phe Leu Ile Ala Thr Leu Gly Leu Arg Val Tyr Leu
225                 230                 235                 240
Ala Trp Ile Thr Arg Thr Gly Tyr Thr Tyr Gly Ala Leu Ala Thr Pro
                245                 250                 255
Ile Ala Phe Leu Leu Phe Ala Phe Phe Gly Gly Phe Ala Ile Met Leu
                260                 265                 270
Gly Ala Glu Leu Asn Ala Ala Val Gln Glu Glu Trp Pro Ala Pro Ala
            275                 280                 285
Thr His Ala His Arg Leu Gly Asn Trp Leu Lys Ala Arg Ile Gly Val
    290                 295                 300
Gly Thr Thr Thr Tyr Ser Ser Thr Ala Gln His Ser Ala Val Ala Ala
305                 310                 315                 320
Glu Pro Pro Ser
```